US008173428B2

(12) United States Patent
Rosenbohm et al.

(10) Patent No.: US 8,173,428 B2
(45) Date of Patent: *May 8, 2012

(54) LNA OLIGONUCLEOTIDES AND THE TREATMENT OF CANCER

(75) Inventors: Christoph Rosenbohm, Birkerod (DK); Lene Sonderbye Kjaerulff, Skaevinge (DK); Majken Westergaard, Birkerod (DK); Margit Wissenbach, Fredensborg (DK); Jens Bo Hansen, Vaerlose (DK); Marlene Asklund, Frederiksberg C (DK)

(73) Assignees: Santaris Pharma A/S, Hersholm (DK); Enzon Pharmaceuticals, Inc., Piscataway, NJ (US)

( * ) Notice: Subject to any disclaimer, the term of this patent is extended or adjusted under 35 U.S.C. 154(b) by 66 days.

This patent is subject to a terminal disclaimer.

(21) Appl. No.: 12/249,676

(22) Filed: Oct. 10, 2008

(65) Prior Publication Data

US 2009/0181914 A1 Jul. 16, 2009

Related U.S. Application Data

(62) Division of application No. 11/272,124, filed on Nov. 9, 2005, now abandoned.

(60) Provisional application No. 60/626,561, filed on Nov. 9, 2004.

(51) Int. Cl.
*C12N 15/00* (2006.01)
*C12N 5/00* (2006.01)
*C07H 21/04* (2006.01)

(52) U.S. Cl. .................. 435/455; 536/24.5; 435/375

(58) Field of Classification Search .................. None
See application file for complete search history.

(56) References Cited

U.S. PATENT DOCUMENTS

| | | | |
|---|---|---|---|
| 5,108,921 A | 4/1992 | Low et al. | |
| 5,227,400 A | 7/1993 | Holton et al. | |
| 5,248,796 A | 9/1993 | Chen et al. | |
| 5,250,683 A | 10/1993 | Holton et al. | |
| 5,254,580 A | 10/1993 | Chen et al. | |
| 5,272,171 A | 12/1993 | Ueda et al. | |
| 5,278,324 A | 1/1994 | Kingston et al. | |
| 5,874,416 A | 2/1999 | Sheikhnejad | |
| 6,077,709 A | 6/2000 | Bennett et al. | |
| 6,117,848 A | 9/2000 | Monia et al. | |
| 6,310,044 B1 | 10/2001 | Draper et al. | |
| 6,509,162 B1 | 1/2003 | Altieri | |
| 6,593,091 B2 | 7/2003 | Keys et al. | |
| 7,741,309 B2 * | 6/2010 | Hansen et al. | 514/44 R |
| 2002/0137708 A1 | 9/2002 | Bennett et al. | |
| 2003/0032794 A1 | 2/2003 | Koch et al. | |
| 2004/0005567 A1 | 1/2004 | Dean et al. | |
| 2004/0241717 A1 | 12/2004 | Hansen et al. | |
| 2004/0248840 A1 | 12/2004 | Hansen et al. | |
| 2005/0014712 A1 * | 1/2005 | Hansen et al. | 514/44 |
| 2006/0160095 A1 * | 7/2006 | Hayes et al. | 435/6 |

FOREIGN PATENT DOCUMENTS

| | | |
|---|---|---|
| EP | 0 253 739 B1 | 10/1989 |
| WO | WO 92/09589 A1 | 6/1992 |
| WO | WO 92/22651 | 12/1992 |
| WO | WO 93/18210 A1 | 9/1993 |
| WO | WO 94/08003 | 4/1994 |
| WO | WO 94/28720 | 12/1994 |
| WO | WO 98/22589 | 5/1998 |
| WO | WO 98/49349 | 11/1998 |
| WO | WO 98/50540 | 11/1998 |
| WO | WO 99/02732 | 1/1999 |
| WO | WO 99/14226 A2 | 3/1999 |
| WO | WO 99/22772 | 5/1999 |
| WO | WO 00/18781 | 4/2000 |
| WO | WO 00/56746 A2 | 9/2000 |
| WO | WO 00/56748 A1 | 9/2000 |
| WO | WO 00/66604 A2 | 11/2000 |
| WO | WO 01/25248 A2 | 4/2001 |
| WO | WO 01/46455 A2 | 6/2001 |
| WO | WO 01/48190 A2 | 7/2001 |
| WO | WO 01/57059 A1 | 8/2001 |
| WO | WO 01/64741 A2 | 9/2001 |
| WO | WO 02/28875 A2 | 4/2002 |
| WO | WO 02/094250 A2 | 11/2002 |
| WO | WO 03/006475 A2 | 1/2003 |
| WO | WO 03/027244 A2 | 4/2003 |
| WO | WO03191384 | * 4/2003 |
| WO | WO 03/091384 A3 | 11/2003 |

(Continued)

OTHER PUBLICATIONS

Kurreck et al. Nucl. Acids Res. (2002), vol. 30 (9): 1911-1918.*

(Continued)

*Primary Examiner* — Janet Epps-Smith
(74) *Attorney, Agent, or Firm* — Stoel Rives LLP

(57) ABSTRACT

The present disclosure concerns LNA oligonucleotides having a (sub)sequence of the general formula $5'-(^{Me}C_x)(T_x)^{Me}C_xA_st_sc_sc_sa_st_sg_sg_s{}^{Me}C_xA_x(G_x)(c)-3'$, and preferably of the general formula $5'-{}^{Me}C_xT_x{}^{Me}C_xA_sa_st_sc_sc_sa_st_sg_sg_s{}^{Me}C_xA_xG_xc-3'$, wherein capital letters designate an LNA nucleotide analogue selected from β-D-oxy-LNA, β-D-thio-LNA, β-D-amino-LNA and α-L-oxy-LNA, small letters designate a deoxynucleotide, and underline designates either an LNA nucleotide analogue as defined above or a deoxynucleotide. Such LNA oligonucleotides exhibit surprisingly good properties with respect to inhibition of the expression of Survivin by means of an antisense mechanism, and thereby lead to reduction or inhibition of tumor development in vivo. The LNA oligonucleotides are superior to other LNA oligonucleotides targeting Surviving mRNA measured by functional read outs such as apoptosis induction and proliferation inhibition, and is potent in down-regulating Survivin mRNA and protein in transfected cancer cell lines, and induce apoptosis in combination with Taxol superior compared to other LNA oligonucleotides.

2 Claims, 19 Drawing Sheets

FOREIGN PATENT DOCUMENTS

| WO | WO 03/095467 A1 | 11/2003 |
| --- | --- | --- |
| WO | WO 03/102019 A2 | 12/2003 |
| WO | WO 2004/069991 A2 | 8/2004 |
| WO | WO2004/069991 A2 | 8/2004 |
| WO | WO2006006991 * | 8/2004 |

OTHER PUBLICATIONS

Wang et al., 2003, "Survivin Antisense RNA Enhances Taxol-Induced Apoptosis in Leukemia Cell Line HL-60," Zhonghua Xue Ye Xue Za Zhi. 24(7):351-54, (abstract only).*

Adida, et al., "Anti-apoptosis gene, surviving, and prognosis of neuroblastoma," Lancet, vol. 351, pp. 882-883 (1998).

Altieri, "Survivn, versatile modulation of cell division and apoptosis in cancer," Oncogene, vol. 22, pp. 8581-8589 (2003).

Altmann, et al., "Novel Chemistry," 1998, Applied Antisense Oligonucleotide Technology, Chapter 4, pp. 73-107.

Ambrosini, et al., "A novel anti-apoptosis gene, surviving, expressed in cancer and lymphoma," Nat. Med., vol. 3, No. 8, pp. 917-921 (1997).

Ambrosini, et al., "Induction of Apoptosis and Inhibition of Cell Proliferation by surviving Gene Targeting," J. Biol. Chem., vol. 273, No. 18, pp. 11177-11182 (1998).

Ansell, et al., "Inhibition of surviving expression suppresses the growth of aggressive non-Hodgkin's lymphoma," Leukemia, vol. 18, pp. 616-623 (2004).

Asanuma, et al., Jpn. J. Cancer Res., vol. 93, pp. 1057-1062 (2002).

Ashkenazi, et al., "Death Receptors: Signaling and Modulation," Science, vol. 281, pp. 1305-1308 (1998).

Beaucage et al., "Advances in the Synthesis of Oligonucleotides by the Phosphoramidite Approach," Tetrahedron, 48(12):2223-2311 (1992).

Beaucage et al., "The Synthesis of Modified Oligonucleotides by the Phosphoramidite Approach and Their Applications," Tetrahedron, 49(28):6123-6194 (1993).

Beltrami, et al., "Acute Ablation of Survivin Uncovers p53-Dependent Mitotic Checkpoint Functions and Control of Mitochondrial Apoptosis," J. Biol. Chem., vol. 279, pp. 2077-2084 (2003).

Bennett, et al., "ras Oncogenes," Antisense Therapeutics, pp. 16-27 (1996).

Blanc-Brude, et al., "Therapeutic Targeting of the Survivin Pathway in Cancer: Initiation of Mitochondrial Apoptosis and Suppression of Tumor-associated Angiogenesis," Clin. Cancer Res., vol. 9, p. 2683-2692 (2003).

Brown et al., "In Oligonucleotides and Analogues. A Practical Approach," Oxford: IRL 13-14 (1991).

Cao et al., "XIAP and Survivin as Therapeutic Targets for Radiation Sensitization in Preclinical Models of Lung Cancer," Oncogene, 23:1-6 (2004).

Carvalho, et al., "Survivin is required for stable checkpoint activation in taxol-treated HeLa cells," J. Cell. Sci., vol. 116(14), pp. 2987-2998 (2003).

Chen, et al., "Down-regulation of Survivin by Antisense Oligonucleotides Increases Apoptosis, Inhibits Cytokinesis and Anchorage-Independent Growth," Neoplasia, vol. 2, No. 3, pp. 235-241 (2000).

Chen, et al., "Survivin Enhances Aurora-B Kinase Activity and Localizes Aurora-B in Human Cells," J. Biol. Chem., vol. 278, pp. 486-490 (2003).

Chin, et al., "Essential role for oncogenic Ras in tumour maintenance," Nature, vol. 400, pp. 468-472 (1999).

Chin, On the Preparation and Utilization of Isolated and Purified Oligonucleotides, Public Collection of the Kathrine R. Everett Law Library of the University of North Carolina, Mar. 9, 2002 (2002).

Cohen, "Caspases: the executioners of apoptosis," Biochem. J., vol. 326, pp. 1-16 (1997).

Conway, et al., "Deficiency of Survivin in Transgenic Mice Exacerbates Fas-Induced Apoptosis Via Mitochondrial Pathways," Gastroenterology, vol. 123, pp. 619-631 (2002).

Cowsert, "In vitro and in vivo activity of antisense inhibitors of ras: potential for clinical development," Anti-Cancer Drug Design, vol. 12, pp. 359-371 (1997).

Crooke, R.M., "In Vitro Cellular Uptake, Distribution and Metabolism of Oligonucleotides," Antisense Res. and Application 131:103-140 (1997).

Cunningham, et al., "A Phase I Trial of H-ras Antisense Oligonucleotide ISIS 2503 Administered as a Continuous Intravenous Infusion in Patients with Advanced Carcinoma," Amer. Cancer Soc., vol. 92, pp. 1265-1271 (2001).

Dean, et al., "Inhibition of Protein Kinase C-α Expression in Human A549 Cells by Antisense Oligonucleotides Inhibits Induction of Intercellular Adhesion Molecule 1 (ICAM-1) MRNA by Phorbol Esters," J. Biol. Chem., 269(23):16416-16424 (1994).

Evan, et al., "Proliferation, cell cycle and apoptosis in cancer," Nature, vol. 411, pp. 342-348 (2001).

Freier, "The ups and downs of nucleic acid duplex stability: structure-stability studies on chemically-modified DNA:RNA duplexes," et al., Nucl. Acid Res., vol. 25, pp. 4429-4443 (1997).

Gray, et al., "Antisense DNA Inhibition of Tumor Growth Induced by c-Ha-ras Oncogene in Nude Mice," Cancer Research, vol. 53, pp. 577-580 (1993).

Green, et al., "Mitochondria and Apoptosis," Science, vol. 281, pp. 1309-1312 (1998).

Grossman, et al., "Expression and Targeting of the Apoptosis Inhibitor, Survivin, in Human Melanoma," J. Invest. Dermatol., 113(6):1076-1081 (1999).

Grossman, et al., "Inhibition of melanoma tumor growth in vivo by surviving targeting," Proc. Nat'l. Sci.., vol. 98, pp. 635-640 (2001).

Grossman, et al., "Transgenic expression of surviving in keratinocytes counteracts UVB-induced apoptosis and cooperates with loss of p53," J. Clin. Invest., vol. 108, No. 7, pp. 991-999 (2001).

Hanahan, et al., "The Hallmarks of Cancer," Cell, vol. 100, pp. 57-70 (2000).

Hengartner, "The biochemistry of apoptosis," Nature, vol. 407, pp. 770-776 (2000).

Holmes, et al., "Phase II Trial of Taxol, an Active Drug in the Treatment of Metastatic Breast Cancer," J. Nat'l Cancer Inst., 83(24)1797-1805 (1991).

Holton et al., "First Total Synthesis of Taxol. 1. Functionalization of the B Ring," J. Am. Chem. Soc., 116(4):1597-1598 (1994).

Jiang, et al., "Participation of Survivin in Mitotic and Apoptotic Activities of Normal and Tumor-Derived Cells," J. Cell. Biochem., vol. 83, pp. 342-354 (2001).

Kawasaki, et al., "Inhibition of Apoptosis by Survivin Predicts Shorter Survival Rates in Colorectal Cancer," Cancer Res., vol. 58, pp. 5071-5074 (1998).

Kohn, et al., "Dose-Intense Taxol: High Response Rate in Patients with Platinum-Resistant Recurrent Ovarian Cancer," J. Nat'l Cancer Inst., 86(1)18-24 (1994).

Kurreck, et al., Design of antisense oligonucleotides stabilized by locked nucleic acids, Nucleic Acids Research, 30(9):1911-1918 (2002).

Leamon et al., "Delivery of Macromolecules into Living Cells: A Method that Exploits Folate Receptor Endocytosis," Proc. Nat. Acad. Sci., 88:5572-5576 (1991).

Lens, et al., "Survivin is required for a sustained spindle checkpoint arrest in response to lack of tension," EMBO J., vol. 22, pp. 2934-2947 (2003).

Li, et al., "Control of apoptosis and mitotic spindle checkpoint by surviving," Nature, vol. 396, pp. 580-584 (1998).

Li, et al., "Pleiotropic cell-division defects and apoptosis induced by interference with surviving function," Nature Cell Biology, vol. 1, pp. 461-466 (1999).

Ling, et al., Induction of surviving expression by taxol (paclitaxel) is an early event which is independent of taxol-mediated G2/M arrest, J. Biol. Chem. (2004).

Lu et al., "Survivin as a Therapeutic Target for Radiation Sensitization in Lung Cancer," Cancer Research, 64:2840-2845 (2004).

Mahotka, et al., "Survivin-ΔEx3 and Survivin-2B: Two Novel Splice Variants of the Apoptosis Inhibitor Survivin with Different Antiapoptotic Properties," Cancer Res., vol. 59, pp. 6097-6102 (1999).

Marusawa, et al., "HBXIP functions as a cofactor of surviving in apoptosis suppression," EMBO Journal, vol. 22, No. 11, pp. 2729-2740 (2003).

McGuire et al., "Taxol: A Unique Antineoplastic Agent with Significant Activity in Advanced Ovarian Epithelial Neoplasms." *Ann. Intern. Med.* 111:273-279 (1989).

Mesri, et al., "Suppression of Vascular Endothelial Growth Factor-Mediated Endothelial Cell Protection by Survivin Targeting," *Am. J. Pathol.*, vol. 158, pp. 1757-1765 (2001).

Mesri, et al., "Cancer gene therapy using a surviving mutant adenovirus," *J. Clin. Invest.*, vol. 108, pp. 981-990 (2001).

Morita, et al., 2'-O,4'-C-Ethylene-Bridged Nucleic Acids (ENA): Highly Nuclease-Resistant and Thermodynamically Stable Oligonucleotides for Antisense Drug, 2002, *Biorganic & Medicinal Chemistry Letters*, vol. 12:73-76.

Nicholson, "From Bench to clinic with apoptosis-based therapeutic agents," *Nature*, vol. 407, pp. 810-816 (2000).

Nocolaou, et al., "Total Synthesis of Taxol," *Nature* 367:630-634 (1994).

O'Connor, et al., "Control of Apoptosis during Angiogenesis by Survivin Expression in Endothelial Cells," *Am. J. Pathol.*, vol. 156, pp. 393-398 (2000).

Olie, et al., "A Novel Antisense Oligonucleotide Targeting Survivin Expression Induces Apoptosis and Sensitizes Lung Cancer Cells to Chemotherapy," *Cancer Res.*, vol. 60, pp. 2805-2809 (2000).

Pedersen, et al., *Synthesis*, No. 6, pp. 802-808 (2002).

Pennati, et al., "Ribozyme-mediated inhibition of surviving expression increases spontaneous and drug-induced apoptosis and decreases the tumorigenic potential of human prostate cancer cells," *J. Invest. Dermatol.*, vol. 120, pp. 648-654 (2003).

Pennati, et al., *Oncogene*, vol. 23, pp. 386-394 (2004).

Rait, et al., Inhibitory effects of the combination of HER-2 antisense oligonucleotide and chemotherapeutic agents used for the treatment of human breast cancer, 2001, *Cancer Gene Therapy*, 8(10):728-739.

Rodel, et al., Int. *J. Radiat. Oncol. Biol. Phys.*, vol. 55, No. 5, pp. 1341-1347 (2003).

Rosenbohm, et al., *Org. Biomol. Chem.*, vol. 1, pp. 655-663 (2003).

Schwab, et al., "Antisense oligonucleotides adsorbed to polyalkylcyanoacrylate nanoparticles specifically inhibit mutated Ha-ras-mediated cell proliferation and tumorigenicity in nude mice," *Proc. Nat'l. Acad. Sci. USA*, vol. 91, pp. 10460-10464 (1994).

Singh, et al., *J. Org. Chem.*, vol. 63, No. 18, pp. 6078-6079 (1998).

Shankar, et al., "Survivin inhibition induces human neural tumor cell death through caspase-independent and -dependent pathways," 2001, *Journal of Neurochemistry*, vol. 79:426-436.

Schwartz, et al., "Phase I Study of the Cyclin-Dependent Kinase Inhibitor Flavopiridol in Combination with Paclitaxel in Patients with Advanced Solid Tumors," *J. Clin. Oncol.*, vol. 20, No. 8, pp. 2157-2170 (2002).

Shin, et al., "An Anti-apoptotic Protein Human Survivin is a Direct Inhibitor of Caspase-3 and -7," *BioChem.*, vol. 40, pp. 1117-1123 (2001).

Sorensen, et al., *Journal American Chem. Soc.*, pp. 2164-2176 (2002).

Tamm, et al., "IAP-Family Protein Survivin Inhibits Caspase Activity and Apoptosis Induced by Fas (CD95), Bax, Caspases, and Anticancer Drugs," *Cancer Res.*, vol. 58, pp. 5315-5320 (1998).

Tran, et al., "Marked Induction of the IAP Family Antiapoptotic Proteins Survivin and XIAP by VEGF in Vascular Endothelial Cells," *Biochem. Biophys. Res. Commun.*, vol. 264, pp. 781-788 (1999).

Tran, et al., "A role for surviving in chemoresistance of endothelial cells mediated by VEGF," *Proc. Nat'l. Acad. Sci.*, vol. 99, No. 7, pp. 4349-4354 (2002).

Uhlmann, et al., "Recent advances in the medicinal chemistry of antisense oligonucleotides," *Curr. Opinion in Drug Discovery & Development*, vol. 3, No. 2, pp. 203-213(2000).

Uren, et al., "Survivin and the inner centromere protein INCENP show similar cell-cycle localization and gene knockout phenotype," *Curr. Biol.*, vol. 10, No. 21, pp. 1319-1328 (2000).

Wagner, et al., "Transferrin-Polycation Conjugates as Carriers for DNA Uptake into Cells," *Proc. Nat. Acad. Sci.*, 87:3410-3414 (1990).

Wang, et al., "Survivin Antisense RNA Enhances Taxol-Induced Apoptosis in Leukemia Cell Line HL-60," *Zhonghua Xue Ye Xue Za Zhi.* 24(7):351-54 (2003).

Watts, et al., "Antisense Effects of ISIS 114926 on the Novel IAP Family Member, Survivin in CCL4-induced Mouse Liver Regeneration Model," *Molecular Biology*, 42(17):459, #2468 (2001).

Xia, et al., "Induction of Apoptosis in Mesothelioma Cells by Antisurvivin Oligonucleotides," *Molecular Cancer Therapeutics*, vol. 1, pp. 687-694 (2002).

Zaffaroni, et al., "Expression of the anti-apoptotic gene surviving correlates with taxol resistance in human ovarian cancer," *Cell. Mol. Life Sci.*, vol. 59, pp. 1406-1412 (2002).

Zangemeister-Wittke, "Antisense to Apoptosis Inhibitors Facilitates Chemotherapy and TRIAL-Induced Death Signaling," *Ann. N.Y. Acad. Sci.* 1002:90-94 (2003).

Zhao, et al., "The ubiquitin-proteasome pathway regulates surviving degradation in a cell cycle-dependent manner," *Jr. Cell Sci.*, vol. 113, pp. 4363-4371 (2000).

Zhou, et al., "DNA Damage Induces a Novel p53-Survivin Signaling Pathway Regulating Cell Cycle and Apoptosis in Acute Lymphoblastic Leukemia Cells," *J. Pharmacol. Exp. Ther.*, vol. 303, pp. 124-131 (2002).

Office Action from U.S. Appl. No. 10/776,934, dated Jul. 20, 2005.
Office Action from U.S. Appl. No. 10/776,934, dated Apr. 17, 2007.
Office Action from U.S. Appl. No. 10/776,934, dated Jan. 8, 2008.
Office Action from U.S. Appl. No. 10/776,934, dated Jan. 9, 2009.
Office Action from parent application, U.S. Appl. No. 10/776,934, dated May 16, 2008.
Office Action from parent application, U.S. Appl. No. 10/776,934, dated Aug. 11, 2008.

Pedersen, et al., "Analogues of LNA (Locked Nucleic Acid): Synthesis of the 2'-Thio-LNA Ribothymidine and 5-Methylcytidine Phosphoramidites," *Synthesis*, No. 4, pp. 0578-0582 (2004).

Notice of Opposition to a European Patent dated Apr. 15, 2010 corresponding to European Patent No. 1,592,793.

Frieden et al., "Expanding the design horizon of antisense oligonucleotides with alpha-L-LNA", Nucleic Acids Research, 2003, vol. 31, No. 21, 6365-6372.

Hansen et al,, "SPC3042: a proapoptotic surviving inhibitor", Mol. Cancer Ther., 2008, 7(9), Sep. 2008, 2736-2745.

Chinese Patent Office Official Action dated Aug. 4, 2010 for Chinese Application No. 2005800409084.

Philippine Patent Office Official Action dated Oct. 4, 2010 for Philippine Application No. 1-2007-500984.

Mexican Patent Office Action dated Nov. 12, 2010 for Mexican Application No. 2007/005557.

Israeli Patent Office Action dated Dec. 5, 2010 for Israeli Patent Application No. 169957.

Zangemeister-Wittke, U., "Antisense to apoptosis inhibitors facilitates chemotherapy and TRAIL-induced death signaling," Ann. N.Y. Acad. Sci., vol. 1002, pp. 90-94 (2003).

Japanese Patent Office Official Action dated Oct. 24, 2011 for Japanese Application No. 2007-539462.

\* cited by examiner

Fig. 7B

24 HOURS

| Fig. 7B1 | Fig. 7B2 |
| Fig. 7B3 | Fig. 7B4 |
| Fig. 7B5 | Fig. 7B6 |

Fig. 7B1
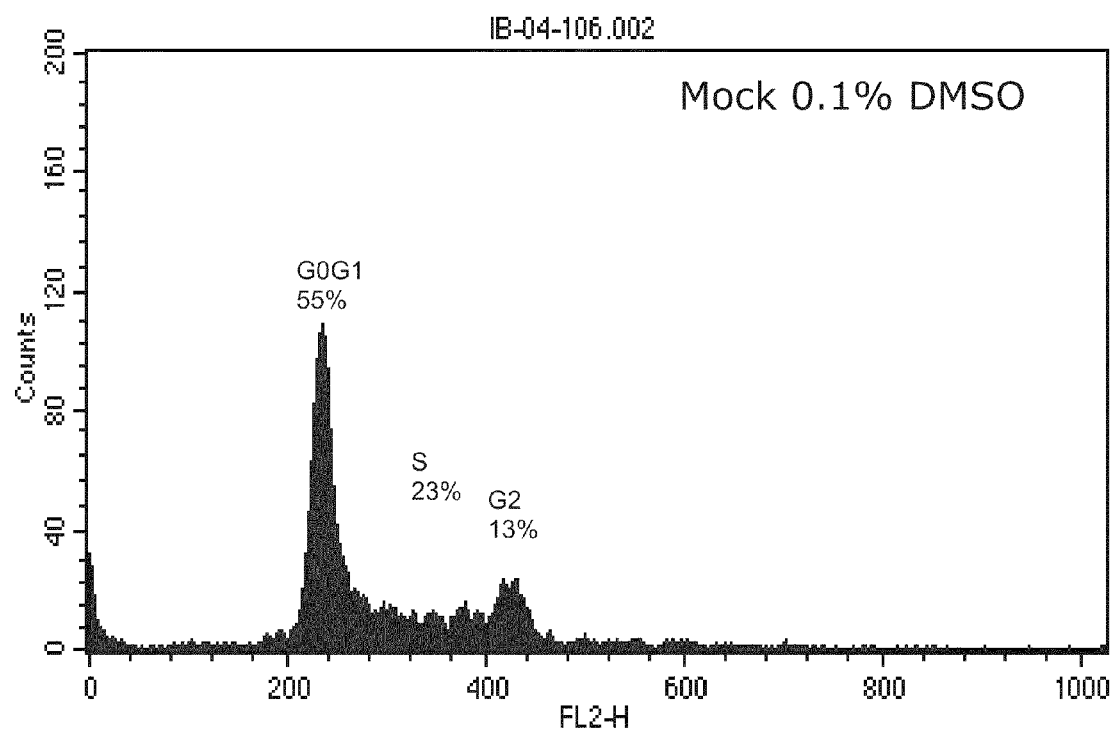

Fig. 7B2
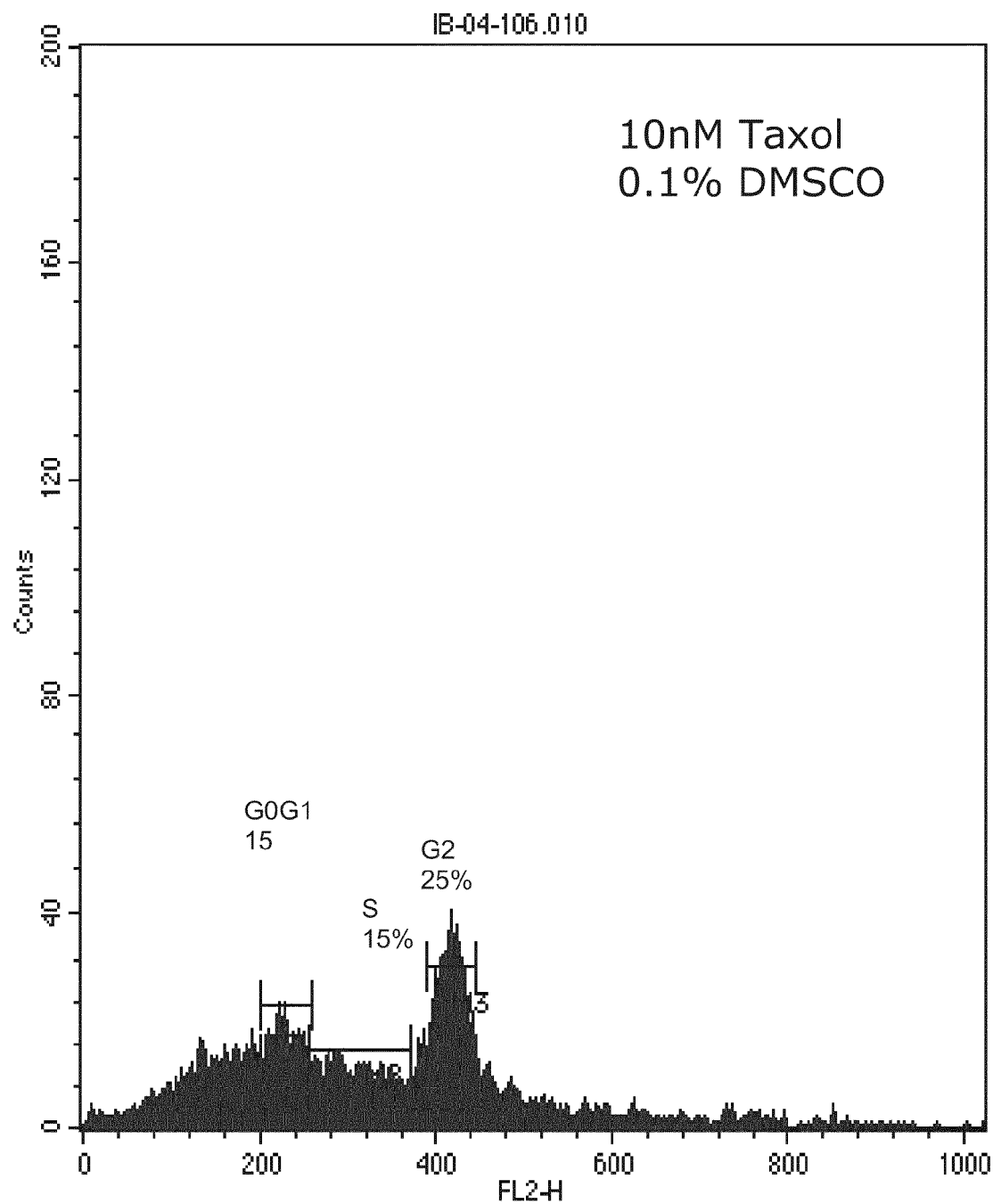

Fig. 7B3
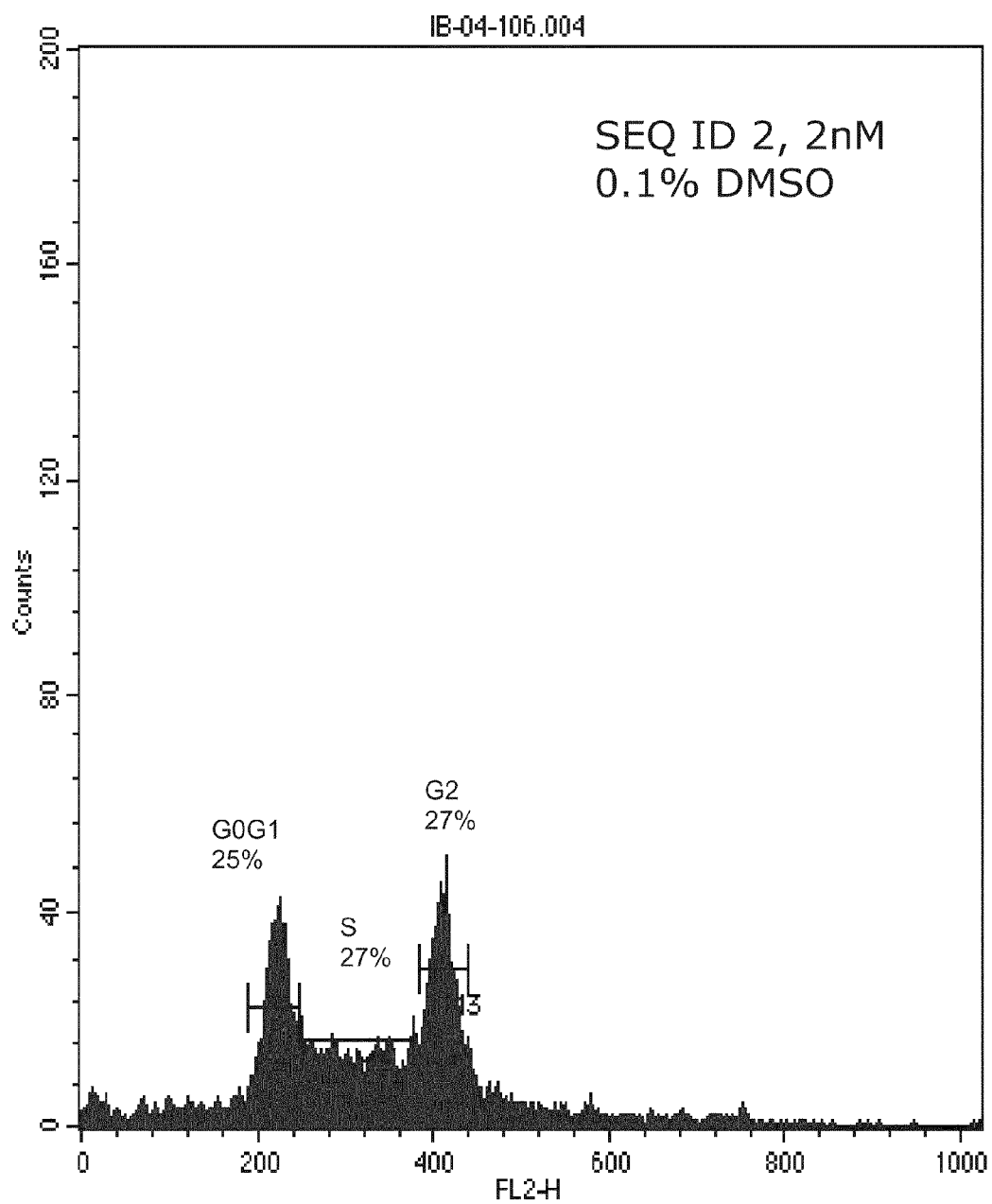

Fig. 7B4
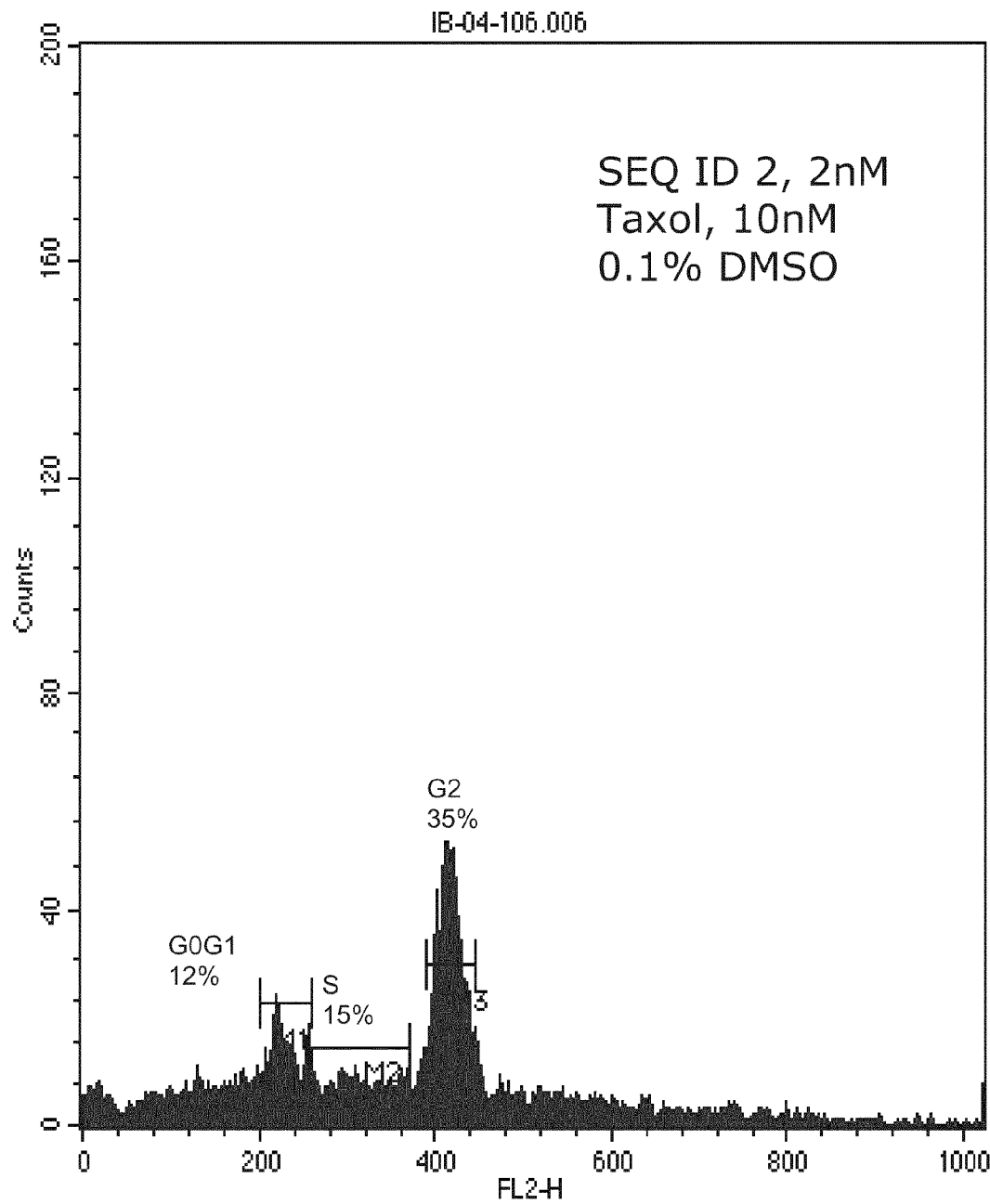

Fig. 7B5
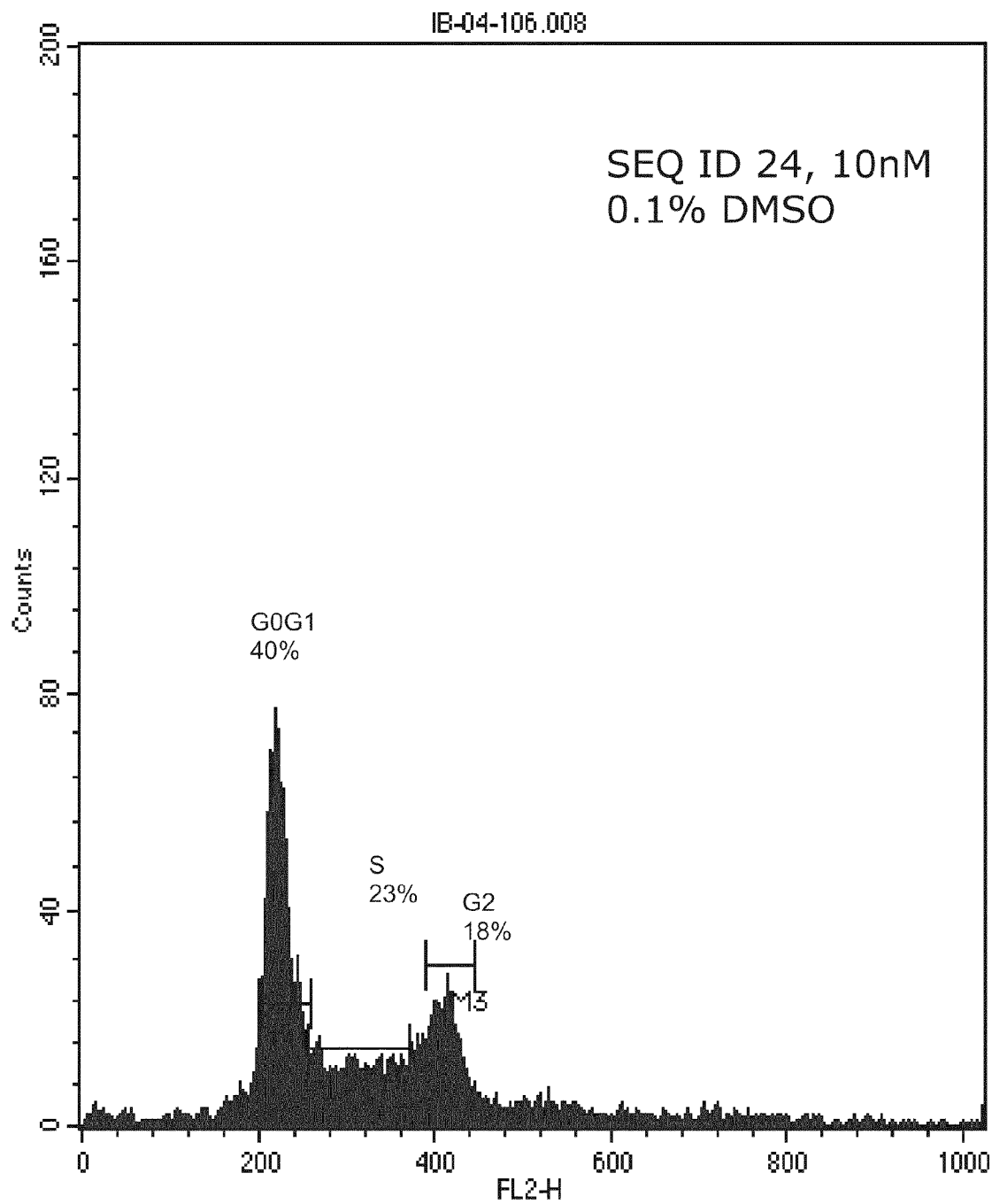

Fig. 7B6
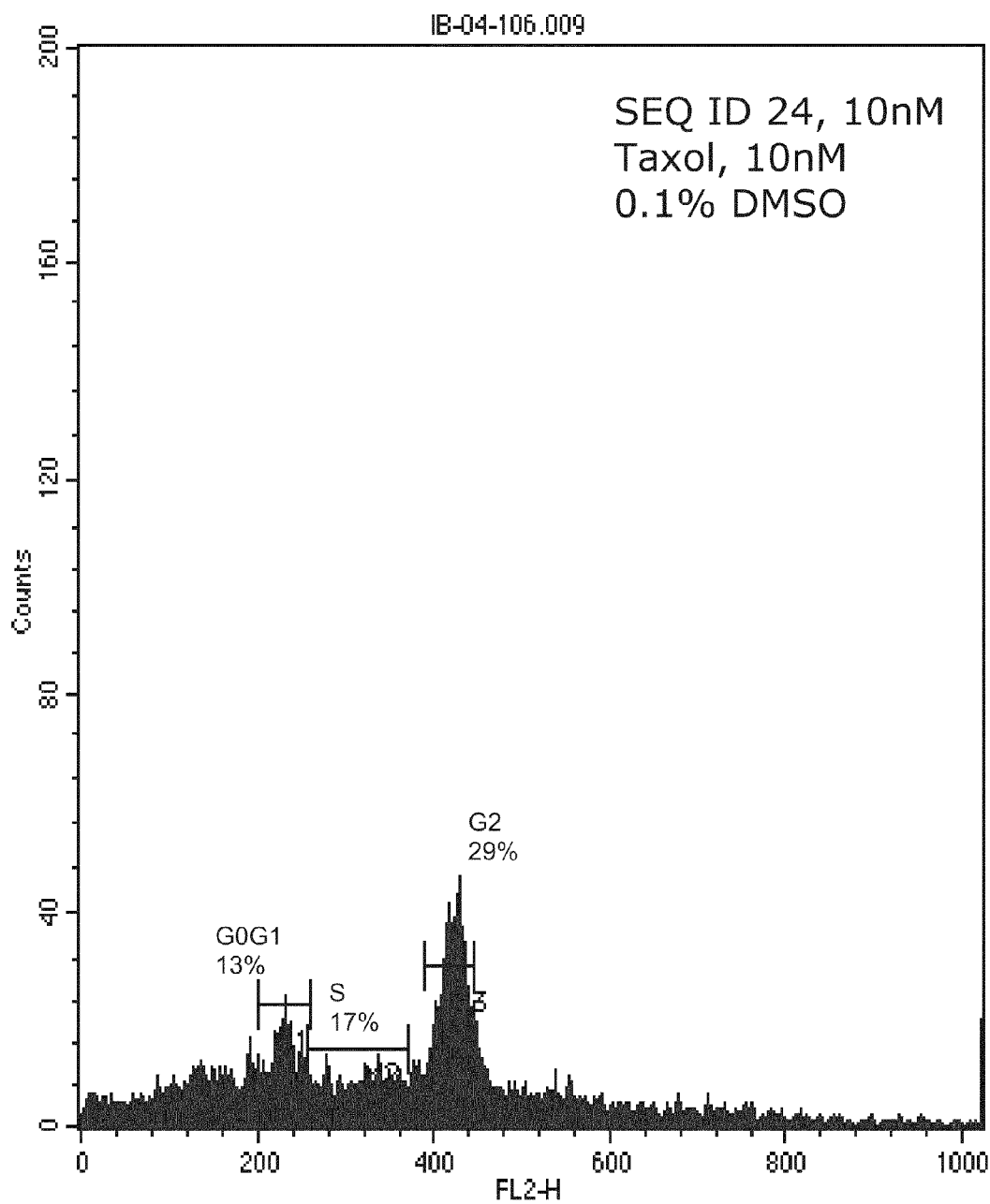

Survivin protein levels in tumour

SEQUENCE LISTING

<160> NUMBER OF SEQ ID NOS: 34

<210> SEQ ID NO 1
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(14)
<223> OTHER INFORMATION: LNA modified nucleotide
<220> FEATURE:
<221> NAME/KEY: misc_feature
<222> LOCATION: (15)..(15)
<223> OTHER INFORMATION: LNA modified nucleotide

<400> SEQUENCE: 1
ctcaatccat ggcagc                                               16

<210> SEQ ID NO 2
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature

```
<222> LOCATION: (13)..(13)
<223> OTHER INFORMATION: 5-methyl modified LNA cytosine
<220> FEATURE:
<221> NAME/KEY: misc_feature
<222> LOCATION: (14)..(14)
<223> OTHER INFORMATION: LNA modified nucleotide
<220> FEATURE:
<221> NAME/KEY: misc_feature
<222> LOCATION: (15)..(15)
<223> OTHER INFORMATION: LNA modified nucleotide

<400> SEQUENCE: 2
ctcaatccat ggcagc                                                    16

<210> SEQ ID NO 3
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(14)
<223> OTHER INFORMATION: LNA modified nucleotide
<220> FEATURE:
<221> NAME/KEY: misc_feature
<222> LOCATION: (15)..(15)
<223> OTHER INFORMATION: LNA modified nucleotide
<220> FEATURE:
<221> NAME/KEY: misc_feature
<222> LOCATION: (15)..(15)
<223> OTHER INFORMATION: Phosphorothioate linkage

<400> SEQUENCE: 3
ctcaatccat ggcagc                                                    16

<210> SEQ ID NO 4
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
```

```
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(14)
<223> OTHER INFORMATION: LNA modified nucleotide
<220> FEATURE:
<221> NAME/KEY: misc_feature
<222> LOCATION: (15)..(15)
<223> OTHER INFORMATION: LNA modified nucleotide

<400> SEQUENCE: 4
ctcaatccat ggcagc                                                    16

<210> SEQ ID NO 5
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (13)..(14)
<223> OTHER INFORMATION: LNA modified nucleotide

<400> SEQUENCE: 5
ctcaatccat ggcagc                                                    16

<210> SEQ ID NO 6
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: misc_feature
```

```
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide

<400> SEQUENCE: 6
ctcaatccat ggcagc                                                     16

<210> SEQ ID NO 7
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(14)
<223> OTHER INFORMATION: LNA modified nucleotide
<220> FEATURE:
<221> NAME/KEY: misc_feature
<222> LOCATION: (15)..(15)
<223> OTHER INFORMATION: Phosphorothioate linkage

<400> SEQUENCE: 7
ctcaatccat ggcagc                                                     16

<210> SEQ ID NO 8
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Phosphorothioate linkage
<220> FEATURE:
<221> NAME/KEY: misc_feature
```

```
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide
<220> FEATURE:
<221> NAME/KEY: misc_feature
<222> LOCATION: (15)..(15)
<223> OTHER INFORMATION: Phosphorothioate linkage

<400> SEQUENCE: 8
ctcaatccat ggcagc                                                    16

<210> SEQ ID NO 9
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(14)
<223> OTHER INFORMATION: LNA modified nucleotide

<400> SEQUENCE: 9
ctcaatccat ggcagc                                                    16

<210> SEQ ID NO 10
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
```

```
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide

<400> SEQUENCE: 10
ctcaatccat ggcagc                                                     16

<210> SEQ ID NO 11
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide

<400> SEQUENCE: 11
ctcaatccat ggcagc                                                     16

<210> SEQ ID NO 12
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
```

```
<222> LOCATION: (1)..(15)
<223> OTHER INFORMATION: Phosphorothioate linkage
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide

<400> SEQUENCE: 12
ctcaatccat ggcagc                                                 16

<210> SEQ ID NO 13
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide

<400> SEQUENCE: 13
ctcaatccat ggcagc                                                 16

<210> SEQ ID NO 14
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
```

```
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide

<400> SEQUENCE: 14
ctcaatccat ggcagc                                                    16

<210> SEQ ID NO 15
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (13)..(14)
<223> OTHER INFORMATION: LNA modified nucleotide

<400> SEQUENCE: 15
ctcaatccat ggcagc                                                    16

<210> SEQ ID NO 16
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
```

```
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide

<400> SEQUENCE: 16
ctcaatccat ggcagc                                                        16

<210> SEQ ID NO 17
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(14)
<223> OTHER INFORMATION: LNA modified nucleotide
<220> FEATURE:
<221> NAME/KEY: misc_feature
<222> LOCATION: (15)..(15)
<223> OTHER INFORMATION: Phosphorothioate linkage

<400> SEQUENCE: 17
ctcaatccat ggcagc                                                        16

<210> SEQ ID NO 18
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Phosphorothioate linkage
<220> FEATURE:
<221> NAME/KEY: misc_feature
```

```
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide
<220> FEATURE:
<221> NAME/KEY: misc_feature
<222> LOCATION: (15)..(15)
<223> OTHER INFORMATION: Phosphorothioate linkage

<400> SEQUENCE: 18
ctcaatccat ggcagc                                                     16

<210> SEQ ID NO 19
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(14)
<223> OTHER INFORMATION: LNA modified nucleotide

<400> SEQUENCE: 19
ctcaatccat ggcagc                                                     16

<210> SEQ ID NO 20
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
```

```
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide

<400> SEQUENCE: 20
ctcaatccat ggcagc                                               16

<210> SEQ ID NO 21
<211> LENGTH: 18
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: LNA modified nucleotide
<220> FEATURE:
<221> NAME/KEY: misc_feature
<222> LOCATION: (1)..(17)
<223> OTHER INFORMATION: Phosphorothioate linkage
<220> FEATURE:
<221> NAME/KEY: misc_feature
<222> LOCATION: (15)..(18)
<223> OTHER INFORMATION: LNA modified nucleotide

<400> SEQUENCE: 21
tgtgctattc tgtgaatt                                             18

<210> SEQ ID NO 22
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (2)..(2)
<223> OTHER INFORMATION: 5-methyl modified LNA cytosine
<220> FEATURE:
<221> NAME/KEY: misc_feature
<222> LOCATION: (3)..(3)
<223> OTHER INFORMATION: LNA modified nucleotide
<220> FEATURE:
<221> NAME/KEY: misc_feature
<222> LOCATION: (4)..(4)
<223> OTHER INFORMATION: 5-methyl modified LNA cytosine
<220> FEATURE:
<221> NAME/KEY: misc_feature
```

```
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide

<400> SEQUENCE: 22
gcacagttga aacatc                                                 16

<210> SEQ ID NO 23
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (2)..(2)
<223> OTHER INFORMATION: 5-methyl modified LNA cytosine
<220> FEATURE:
<221> NAME/KEY: misc_feature
<222> LOCATION: (3)..(4)
<223> OTHER INFORMATION: LNA modified nucleotide
<220> FEATURE:
<221> NAME/KEY: misc_feature
<222> LOCATION: (13)..(13)
<223> OTHER INFORMATION: LNA modified nucleotide
<220> FEATURE:
<221> NAME/KEY: misc_feature
<222> LOCATION: (14)..(15)
<223> OTHER INFORMATION: 5-methyl modified LNA cytosine
<220> FEATURE:
<221> NAME/KEY: misc_feature
<222> LOCATION: (16)..(16)
<223> OTHER INFORMATION: LNA modified nucleotide

<400> SEQUENCE: 23
gcagtggatg aagcca                                                 16

<210> SEQ ID NO 24
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(4)
<223> OTHER INFORMATION: LNA modified nucleotide
<220> FEATURE:
<221> NAME/KEY: misc_feature
```

```
<222> LOCATION: (13)..(13)
<223> OTHER INFORMATION: LNA modified nucleotide
<220> FEATURE:
<221> NAME/KEY: misc_feature
<222> LOCATION: (14)..(15)
<223> OTHER INFORMATION: 5-methyl modified LNA cytosine

<400> SEQUENCE: 24
cgcagattag aaacct                                                     16

<210> SEQ ID NO 25
<211> LENGTH: 18
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(17)
<223> OTHER INFORMATION: Phosphorothioate linkage

<400> SEQUENCE: 25
tgtgctattc tgtgaatt                                                   18

<210> SEQ ID NO 26
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (14)..(15)
<223> OTHER INFORMATION: 5-methyl modified LNA cytosine

<400> SEQUENCE: 26
ctcccagcgt gcgcca                                                     16

<210> SEQ ID NO 27
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: LNA modified nucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: (2)..(2)
<223> OTHER INFORMATION: 5-methyl modified LNA cytosine
<220> FEATURE:
<221> NAME/KEY: misc_feature
<222> LOCATION: (14)..(14)
<223> OTHER INFORMATION: 5-methyl modified LNA cytosine
<220> FEATURE:
<221> NAME/KEY: misc_feature
```

```
<222> LOCATION: (15)..(15)
<223> OTHER INFORMATION: LNA modified nucleotide

<400> SEQUENCE: 27
accgcgtgcg accctc                                                   16

<210> SEQ ID NO 28
<211> LENGTH: 16
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-methyl modified LNA cytosine
<220> FEATURE:
<221> NAME/KEY: misc_feature
<222> LOCATION: (2)..(2)
<223> OTHER INFORMATION: LNA modified nucleotide
<220> FEATURE:
<221> NAME/KEY: misc_feature
<222> LOCATION: (3)..(3)
<223> OTHER INFORMATION: 5-methyl modified LNA cytosine
<220> FEATURE:
<221> NAME/KEY: misc_feature
<222> LOCATION: (4)..(5)
<223> OTHER INFORMATION: LNA modified nucleotide
<220> FEATURE:
<221> NAME/KEY: misc_feature
<222> LOCATION: (4)..(12)
<223> OTHER INFORMATION: Phosphorothioate linkage
<220> FEATURE:
<221> NAME/KEY: misc_feature
<222> LOCATION: (13)..(13)
<223> OTHER INFORMATION: 5-methyl modified LNA cytosine
<220> FEATURE:
<221> NAME/KEY: misc_feature
<222> LOCATION: (14)..(15)
<223> OTHER INFORMATION: LNA modified nucleotide

<400> SEQUENCE: 28
ctcaatccat ggcagc                                                   16

<210> SEQ ID NO 29
<211> LENGTH: 21
<212> TYPE: DNA
<213> ORGANISM: Artificial
<220> FEATURE:
<223> OTHER INFORMATION: Synthetic oligonucleotide sequence

<400> SEQUENCE: 29
aaggaccacc gcatctctac a                                             21

<210> SEQ ID NO 30
<211> LENGTH: 22
<212> TYPE: DNA
<213> ORGANISM: Artificial
<220> FEATURE:
<223> OTHER INFORMATION: Synthetic oligonucleotide sequence

<400> SEQUENCE: 30
ccaagtctgg ctcgttctca gt                                            22

<210> SEQ ID NO 31
<211> LENGTH: 23
<212> TYPE: DNA
<213> ORGANISM: Artificial
<220> FEATURE:
<223> OTHER INFORMATION: Synthetic oligonucleotide sequence

<400> SEQUENCE: 31
```

```
cgaggctggc ttcatccact gcc                                              23

<210> SEQ ID NO 32
<211> LENGTH: 21
<212> TYPE: DNA
<213> ORGANISM: Artificial
<220> FEATURE:
<223> OTHER INFORMATION: Synthetic oligonucleotide sequence

<400> SEQUENCE: 32
catgtgtgtg gagagcgtca a                                                21

<210> SEQ ID NO 33
<211> LENGTH: 21
<212> TYPE: DNA
<213> ORGANISM: Artificial
<220> FEATURE:
<223> OTHER INFORMATION: Synthetic oligonucleotide sequence

<400> SEQUENCE: 33
gccggttcag gtactcagtc a                                                21

<210> SEQ ID NO 34
<211> LENGTH: 23
<212> TYPE: DNA
<213> ORGANISM: Artificial
<220> FEATURE:
<223> OTHER INFORMATION: Synthetic oligonucleotide sequence

<400> SEQUENCE: 34
cctggtggac aacatcgccc tgt                                              23
```

LNA OLIGONUCLEOTIDES AND THE TREATMENT OF CANCER

CROSS-REFERENCE TO RELATED APPLICATIONS

This application is a divisional application of U.S. patent application Ser. No. 11/272,124 filed on Nov. 9, 2005, which claims priority to U.S. Provisional Patent Application Ser. No. 60/626,561 filed on Nov. 9, 2004 and Patent Application No. PA 2004-01728 filed in the country of Denmark on Nov. 9, 2004, each of which is incorporated herein, by reference, in its entirety.

FIELD OF THE INVENTION

The present invention provides pharmaceutical compositions useful for the treatment of cancer. The compositions comprise a particular LNA oligonucleotide having excellent properties with respect to the inhibition of the expression of Survivin. The present invention also provides a method for treating cancer, and various kits.

BACKGROUND OF THE INVENTION

Survivin is one of the most attractive novel cancer targets. The clinical role of Survivin in cancer has been emphasised by detection of high levels of this protein in almost all tumour types. Elevated expression of Survivin in tumours is generally associated with poor prognosis, increased cancer recurrence and resistance to therapy, both radiation and chemotherapy. The fact that expression of Survivin is, with a few exceptions, not found in normal adult tissues makes Survivin a pivotal cancer gene.

The inhibitor of apoptosis protein (IAP) Survivin is implicated in two key biological events: (i) control of cell proliferation (mitosis), and (ii) regulation of programmed cell death (apoptosis). Additionally, Survivin plays an important role in tumour angiogenesis.

A combination of siRNA targeting Survivin and Taxol results in increased apoptosis induction in SHEP cells compared to siRNA and Taxol alone (Zangemeister-Wittke 2003; Ann. N.Y. Acad. Sci. 1002: 90-94).

Wang et al., 2003; Zhonghua Xue Ye Za Zhi 24, 351-54. "Survivin antisense RNA enhances Taxol-induced apoptosis in leukemia cell line HL-60".

A wide range of possible antisense LNA oligonucleotides were described in the applicants' earlier international patent application publication No. WO 2004/069991 A2. However, the surprisingly good properties of the LNA oligonucleotides disclosed herein have not yet been described in the prior art.

BRIEF DESCRIPTION OF THE INVENTION

A first main aspect of the present invention relates to a liquid pharmaceutical composition comprising an LNA oligonucleotide in an aqueous carrier, said LNA oligonucleotide having a total of 12-20 nucleotides/LNA nucleotide analogues and comprising the following (sub)sequence:

(SEQ ID NO. 28)
5'-($^{Me}\underline{C}_x$)($T_x$)$^{Me}C_x A_s \underline{A}_s t_s c_s c_s a_s t_s g_s g_s{}^{Me}C_x A_x (\underline{G}_x)$(c)-3', preferably having a total of 16-20 nucleotides/LNA nucleotide analogues and comprising the following (sub)sequence:

(SEQ ID NO. 1)
5'-$^{Me}\underline{C}_x T_x{}^{Me}C_x A_s a_s t_s c_s c_s a_s t_s g_s g_s{}^{Me}C_x A_x \underline{G}_x c$-3', wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues; and
said aqueous carrier comprising a buffer for keeping the pH in the range of 4.0-8.5, and having an ionic strength of 20-2000 mM.

A second main aspect of the present invention relates to a liquid pharmaceutical composition comprising a conjugate in an aqueous carrier, said conjugate consisting of an LNA oligonucleotide and at least one non-nucleotide/non-polynucleotide moiety covalently attached to said oligonucleotide, said LNA oligonucleotide having a total of 12-20 nucleotides/LNA nucleotide analogues and comprising the following (sub)sequence:

(SEQ ID NO. 28)
5'-($^{Me}\underline{C}_x$)($T_x$)$^{Me}C_x A_s \underline{A}_s t_s c_s c_s a_s t_s g_s g_s{}^{Me}C_x A_x (\underline{G}_x)$(c)-3', preferably having a total of 16-20 nucleotides/LNA nucleotide analogues and comprising the following (sub)sequence:

(SEQ ID NO. 1)
5'-$^{Me}\underline{C}_x T_x{}^{Me}C_x A_s a_s t_s c_s c_s a_s t_s g_s g_s{}^{Me}C_x A_x \underline{G}_x c$-3', wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues; and
said aqueous carrier comprising a buffer for keeping the pH in the range of 4.0-8.5, and having an ionic strength of 20-2000 mM.

A third aspect of the present invention relates to a pharmaceutical composition comprising at least one taxane compound and an LNA oligonucleotide in a pharmaceutically acceptable carrier, said LNA oligonucleotide having a total of 12-20 nucleotides/LNA nucleotide analogues and comprising the following (sub)sequence:

(SEQ ID NO. 1)
5'-$^{Me}\underline{C}_x T_x{}^{Me}C_x A_s a_s t_s c_s c_s a_s t_s g_s g_s{}^{Me}C_x A_x \underline{G}_x c$-3', wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s"

designates a phosphorothioate link between neighbouring nucleotides/LNA nucleotide analogues, and subscript "x" designates either a phosphorothioate link or a phosphorodiester link between neighbouring nucleotides/LNA nucleotide analogues; and wherein the weight ratio between the taxane compound(s) and the LNA oligonucleotide in said composition is in the range of 50:1 to 1:25.

A fourth main aspect of the present invention relates to a pharmaceutical composition comprising at least one taxane compound and a conjugate in a pharmaceutically acceptable carrier, said conjugate consisting of an LNA oligonucleotide and at least one non-nucleotide/non-polynucleotide moiety covalently attached to said oligonucleotide, said LNA oligonucleotide having a total of 12-20 nucleotides/LNA nucleotide analogues and comprising the following (sub)sequence:

$$5'-(^{Me}\underline{C}_x)(T_x)^{Me}C_xA\underline{A}_xt_sc_sc_sa_st_sg_sg_s^{Me}C_xA_x(\underline{G}_x)(c)-3',$$
(SEQ ID NO. 28)

preferably having a total of 16-20 nucleotides/LNA nucleotide analogues and comprising the following (sub)sequence:

$$5'-^{Me}\underline{C}_xT_x^{Me}C_xA_sa_st_sc_sc_sa_st_sg_sg_s^{Me}C_xA_x\underline{G}_xc-3'$$
(SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues; and wherein the weight ratio between the taxane compound(s) and the LNA oligonucleotide part of the conjugate in said composition is in the range of 50:1 to 1:25.

A fifth main aspect of the present invention relates to the use of an LNA oligonucleotide for the preparation of a pharmaceutical composition for the treatment a mammal, in particular a human, suffering from or susceptible to a cancer disease, said LNA oligonucleotide having a total of 12-20 nucleotides/LNA nucleotide analogues and comprising the following (sub)sequence:

$$5'-(^{Me}\underline{C}_x)(T_x^{Me}C_xA\underline{A}_xt_sc_sc_sa_st_sg_sg_s^{Me}C_xA_x(\underline{G}_x)(c)-3',$$
(SEQ ID NO. 28)

preferably having a total of 16-20 nucleotides/LNA nucleotide analogues and comprising the following (sub)sequence:

$$5'-^{Me}\underline{C}_xT_x^{Me}C_xA_sa_st_sc_sc_sa_st_sg_sg_s^{Me}C_xA_x\underline{G}_xc-3'$$
(SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues.

A sixth main aspect of the present invention relates to the use of a conjugate, said conjugate consisting of an LNA oligonucleotide and at least one non-nucleotide/non-polynucleotide moiety covalently attached to said oligonucleotide, for the preparation of a pharmaceutical composition for the treatment a mammal, in particular a human, suffering from or susceptible to a cancer disease, said LNA oligonucleotide having a total of 12-20 nucleotides/LNA nucleotide analogues and comprising the following (sub)sequence:

$$5'-(^{Me}\underline{C}_x)(T_x)^{Me}C_xA\underline{A}_xt_sc_sc_sa_st_sg_sg_s^{Me}C_xA_x(\underline{G}_x)(c)-3',$$
(SEQ ID NO. 28)

preferably having a total of 16-20 nucleotides/LNA nucleotide analogues and comprising the following (sub)sequence:

$$5'-^{Me}\underline{C}_xT_x^{Me}C_xA_sa_st_sc_sc_sa_st_sg_sg_s^{Me}C_xA_x\underline{G}_xc-3'$$
(SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues.

A seventh main aspect of the present invention relates to a method of treating a mammal, in particular a human, suffering from or susceptible to a cancer disease, the method comprising the step of administering to the mammal one or more therapeutically effective doses of a first pharmaceutical composition comprising an LNA oligonucleotide, said LNA oligonucleotide having a total of 12-20 nucleotides/LNA nucleotide analogues and comprising the following (sub)sequence:

$$5'-(^{Me}\underline{C}_x)(T_x)^{Me}C_xA\underline{A}_xt_sc_sc_sa_st_sg_sg_s^{Me}C_xA_x(\underline{G}_x)(c)-3',$$
(SEQ ID NO. 28)

preferably having a total of 16-20 nucleotides/LNA nucleotide analogues and comprising the following (sub)sequence:

$$5'-^{Me}\underline{C}_xT_x^{Me}C_xA_sa_st_sc_sc_sa_st_sg_sg_s^{Me}C_xA_x\underline{G}_xc-3'$$
(SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues.

An eighth main aspect of the present invention relates to a method of treating a mammal, in particular a human, suffering from or susceptible to a cancer disease, the method comprising the step of administering to the mammal one or more therapeutically effective doses of a first pharmaceutical composition comprising a conjugate, said conjugate consisting of an LNA oligonucleotide and at least one non-nucleotide/non-polynucleotide moiety covalently attached to said oligonucleotide, said LNA oligonucleotide having a total of 12-20 nucleotides/LNA nucleotide analogues and comprising the following (sub)sequence:

(SEQ ID NO. 28)
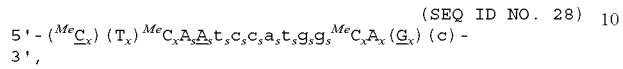

preferably having a total of 16-20 nucleotides/LNA nucleotide analogues and comprising the following (sub)sequence:

(SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues.

A ninth main aspect of the present invention relates to a kit comprising (a) a first component containing one or more injectable solution doses of an LNA oligonucleotide, and (b) a second component containing one or more injectable solutions of one or more taxane compounds;

wherein said LNA oligonucleotide having a total of 12-20 nucleotides/LNA nucleotide analogues and comprising the following (sub)sequence:

(SEQ ID NO. 28)

preferably having a total of 16-20 nucleotides/LNA nucleotide analogues and comprising the following (sub)sequence:

(SEQ ID NO. 1)
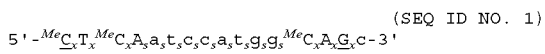

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues; and wherein the weight ratio between the at least one taxane compound in one solution of the second component and the at least one LNA oligonucleotide in one solution does of the first component is in the range of 50:1 to 1:25.

A tenth main aspect of the invention relates to a kit comprising (a) a first component containing an LNA oligonucleotide in solid form, and (b) a second component containing a buffer solution adapted for reconstitution (e.g. dissolution or suspension) of said LNA oligonucleotide;

wherein said LNA oligonucleotide having a total of 12-20 nucleotides/LNA nucleotide analogues and comprising the following (sub)sequence:

(SEQ ID NO. 28)
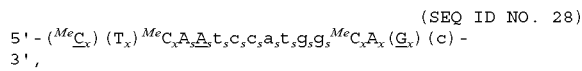

preferably having a total of 16-20 nucleotides/LNA nucleotide analogues and comprising the following (sub)sequence:

(SEQ ID NO. 1)
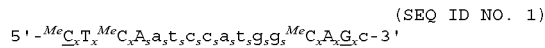

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues.

BRIEF DESCRIPTION OF THE FIGURES

FIGS. 7A and 7B shows cell cycle analysis in 15 PC3 cells treated with SEQ ID NO. 2 and Taxol. 15PC3 cells were transfected with 2 nM of SEQ ID NO. 2 and exposed to either 10 nM of Taxol (in 0.1% DMSO) or vehicle (0.1% DMSO). Cells were stained with Propidium Iodide and analysed by FACS after 24 hours and 48 hours (FIG. 7a), or (FIG. 7b) 24 hours compared 15PC3 cells treated likewise with to 10 nM the negative control SEQ ID NO. 24. This assay shows the specific effect of SEQ ID NO. 2 alone and in combination with Taxol. Cell fractions are increasing in the G2 or even G4 phase when the cell cycle is arrested. Cells treated with SEQ ID NO. 2 are arrested in the cell cycle leading to G1:G2 ratios of 1:1 versus 1:0.25 in mock treated, whereas the negative control SEQ ID. NO 24 has no effect on the cell cycle. Taxol combined with SEQ ID NO. 2 leads to further arrest seen as G1:G2 ratio of 1:3.

DETAILED DESCRIPTION OF THE INVENTION

Figure 1:
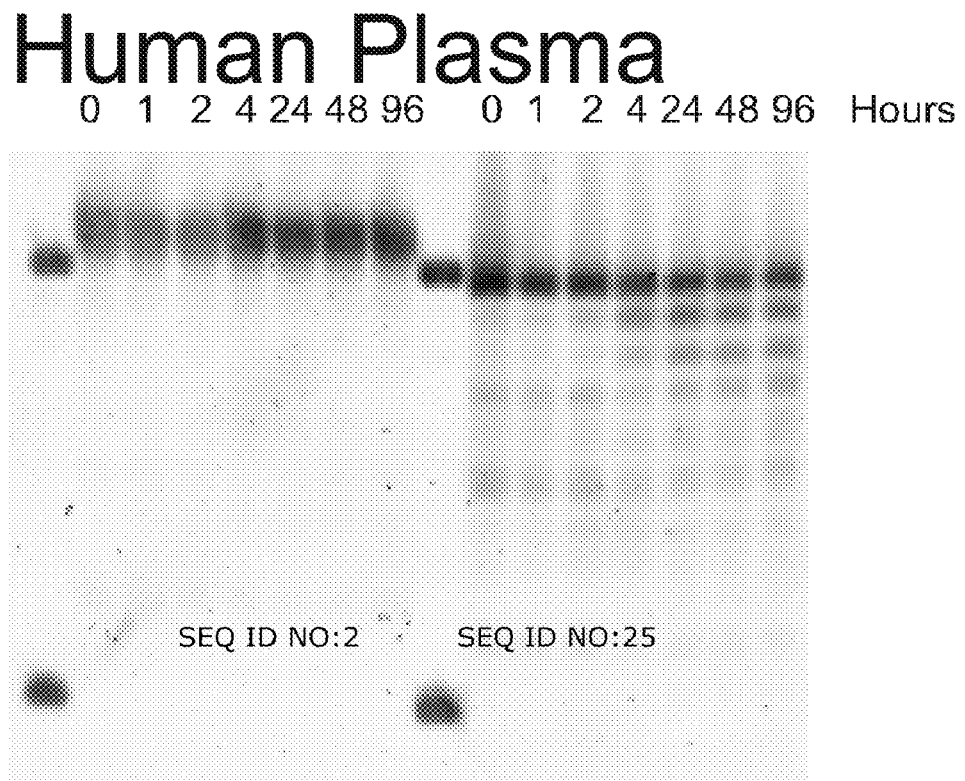
FIG. 1 shows stability of SEQ ID NO. 2 in human and mouse plasma compared to control SEQ ID NO. 25. The oligonucleotides were incubated at 20 μM concentrations at 37° C. for 0-, 1-, 2-, 4-, 24-, 48- or 96-hours. No degradation products of SEQ ID NO. 2 can be detected even after 96 hours digestion in either serum.
Figure 1:
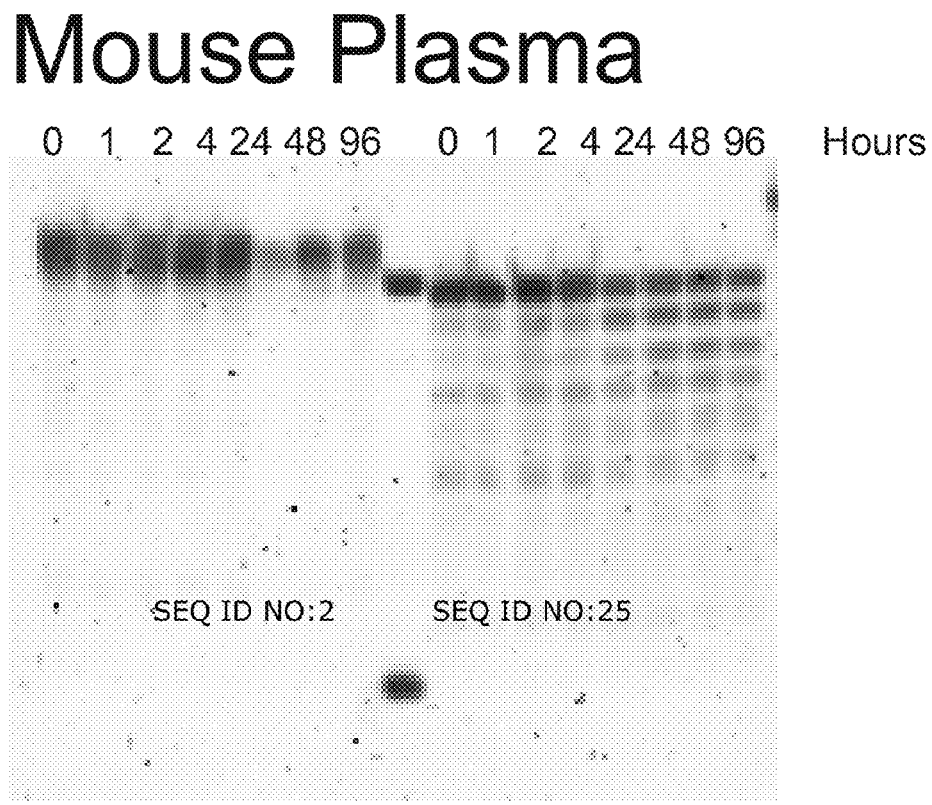

The present inventors have realised that LNA oligonucleotides of a specific class exhibit surprisingly good properties with respect to inhibition of the expression of Survivin by means of an anti-sense mechanism. As it will be clear from the examples, LNA oligonucleotides of this specific class (either alone or in combination with taxane compounds) inhibit the expression of Survivin thereby leading to reduction or inhibition of tumour development in vivo.

The LNA oligonucleotides described herein are represented by the powerful LNA oligonucleotide SEQ ID NO. 2 targeting Survivin. This compound is superior to other LNA oligonucleotides targeting Surviving mRNA measured by functional read outs such as apoptosis induction and proliferation inhibition. Also, the SEQ ID NO. 2 lead candidate is potent in down-regulating Survivin mRNA and protein in transfected cancer cell lines. In addition, the lead candidate SEQ ID NO. 2 induces apoptosis in combination with Taxol superior compared to other LNA oligonucleotides in such combination. An overview of the in vitro data obtained for SEQ ID NO. 2 as well as SEQ ID NO. 23, SEQ ID NO. 22, and SEQ ID NO. 21 is shown in Example 21.

The in vivo xenograft studies in nude mice show Survivin reduction in tumours of single agent treated mice leading to tumour growth inhibition when used in combination with chemotherapeutic drugs. It is the first time an antisense oligonucleotide targeting Survivin shows an effect in combination with Taxol in vivo. The In vivo efficacy testing was conducted using the human mouse prostate cancer xenograft model PC3. Moreover, SEQ ID NO. 2 has a good toxicology profile, and no notable clinical signs were found in an i.v. MTD study in cynomolgus monkeys.

LNA Oligonucleotides

The useful LNA oligonucleotides have a total of 12-20 nucleotides/LNA nucleotide analogues and comprise the (sub)sequence:

(SEQ ID NO. 28)
5'-($^{Me}\underline{C}_x$)($T_x$)$^{Me}C_xA_s\underline{A}_st_sc_sc_sa_st_sg_sg_s{}^{Me}C_xA_x(\underline{G}_x)$(c)-3', preferably having a total of 16-20 nucleotides/LNA nucleotide analogues and comprising the following (sub)sequence:

(SEQ ID NO. 1)
5'-$^{Me}\underline{C}_xT_x{}^{Me}C_xA_sa_st_sc_sc_sa_st_sg_sg_s{}^{Me}C_xA_x\underline{G}_xc$-3' wherein capital letters designate an LNA nucleotide analogue selected from β-D-oxy-LNA, β-D-thio-LNA, β-D-amino-LNA and α-L-oxy-LNA, small letters designate a deoxynucleotide, underline (i.e. $^{Me}\underline{C}$ and $\underline{G}$) designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues, and where the nucleotide units in bracket (i.e. ($^{Me}\underline{C}_x$), ($T_x$), ($\underline{G}_x$) and (c)) each represent an optional unit.

The terms "LNA oligonucleotide defined herein", "LNA oligonucleotide according to the invention", and the like, refer to the "LNA oligonucleotide" defined above, cf. SEQ ID NOS. 1 and 28, as well as the embodiments, variants, salts, prodrugs, etc. described in the following.

The LNA nucleotide analogues are selected from β-D-oxy-LNA, β-D-thio-LNA, β-D-amino-LNA and α-L-oxy-LNA. Those modified nucleotide analogues are Illustrated in the following figure:

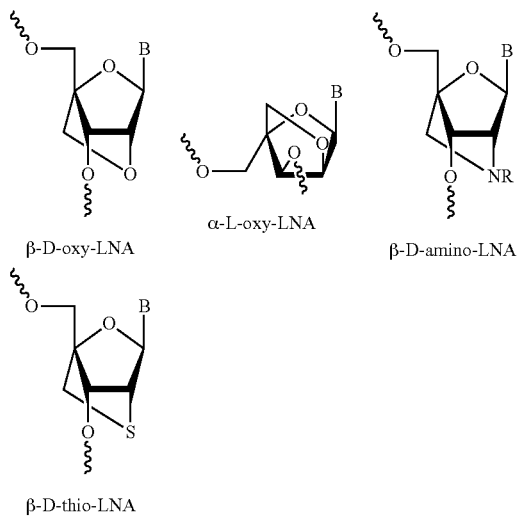

β-D-oxy-LNA    α-L-oxy-LNA    β-D-amino-LNA

β-D-thio-LNA wherein B designates a nucleobase, i.e. either adenine (A), cytosine (C), thymine (T), guanine (G), or methyl-cytosine ($^{Me}$C). For the β-D-amino-LNA, R is a substituent or hydrogen on the ring nitrogen atom. R may, e.g., be hydrogen, methyl, ethyl, propyl, benzyl, etc., or may represent a link to a functional group.

In one embodiment, the LNA nucleotide analogues are selected from β-D-oxy-LNA, β-D-thio-LNA and β-D-amino-LNA. In another embodiment, the LNA nucleotide analogues are selected from β-D-oxy-LNA and α-L-oxy-LNA. In a currently most preferred embodiment, all LNA nucleotide analogues are β-D-oxy-LNA.

When used herein, the term "nucleotide" means a 2-deoxyribose (or ribose) unit which is bonded through its number one carbon atom to one of the nitrogenous bases adenine (A), cytosine (C), thymine (T), uracil (U) or guanine (G), and which is bonded through its number three and/or five carbon atom(s) to an internucleoside phosphorodiester or phosphorothioate group.

The (sub)sequence SEQ ID NO. 28 has at least 12 nucleotides/LNA nucleotide analogues, but is it preferred that the (sub)sequence is represented by at least 13 nucleotides/LNA nucleotide analogues, in particular at least 14 nucleotides/LNA nucleotide analogues. The LNA oligonucleotides defined above may—in addition to the (sub)sequence SEQ ID NO. 28-comprise 1-4 additional nucleotides and/or LNA nucleotide analogues, in particular additional nucleotides, such as 1, 2, 3, or 4 additional 2-deoxynucleotides. Thus typically, the LNA oligonucleotide has a total of 12-20, or 13-20, or 14-20 nucleotides/LNA nucleotide analogues. Preferably, the LNA oligonucleotide has a total of 14-19, such as 14-18, or 15-18, or 16-18, or 14-17, or 15-17, or 16-17, nucleotides/LNA nucleotide analogues. Most preferably, the LNA oligonucleotide is a compound of the sequence SEQ ID NO. 28, i.e. the LNA oligonucleotide has a total of 14-16 nucleotides/LNA nucleotide analogues, e.g. 14 nucleotides/LNA nucleotide analogues, 15 nucleotides/LNA nucleotide analogues, or 16 nucleotides/LNA nucleotide analogues.

Hence, when not all nucleotide units in bracket are present, one preferred variant is the one where ($^{Me}\underline{C}_x$)($T_x$) in the 5'-end are present and (i) where ($\underline{G}_x$)(c) in the 3'-end are absent (providing a 14-mer) or (ii) where ($\underline{G}_x$) is present and where (c) is absent (providing a 15-mer), or (iii) wherein both of ($\underline{G}_x$)(c) are present (providing a 16-mer). Another more preferred variant is the one where ($\underline{G}_x$)(c) in the 3'-end are present and (i) where ($\underline{C}_x$)($T_x$) in the 5'-end are absent (providing a 14-mer) or (ii) where ($T_x$) is present and where ($^{Me}\underline{C}_x$) is absent (providing a 15-mer). An even more preferred embodiment is the one where ($T_x$) in the 5'-end is present and where ($\underline{G}_x$) in the 3'-end is present (providing a 14-mer).

With respect to the underlined units, it is preferred that $^{Me}\underline{C}_x$ designates an LNA nucleotide analogue. Thus, all of $^{Me}\underline{C}_x$, $\underline{A}$ and $\underline{G}$ may represent an LNA nucleotide analogue, or $^{Me}\underline{C}_x$ may represent a deoxynucleotide and $\underline{A}$ and $\underline{G}$ may represent an LNA nucleotide analogue, etc.

The preferred (sub)sequence SEQ ID NO. 1 has 16 nucleotides/LNA nucleotide analogues. The LNA oligonucleotides defined above may—in addition to the (sub)sequence SEQ ID NO. 1-comprise 1-4 additional nucleotides and/or LNA nucleotide analogues, in particular additional nucleotides, such as 1, 2, 3, or 4 additional 2-deoxynucleotides. Thus typically, the LNA oligonucleotide has a total of 16-20 nucleotides/LNA nucleotide analogues. Preferably, the LNA oligonucleotide has a total of 16-19, such as 16-18, or 16-17, nucleotides/LNA nucleotide analogues. Most preferably, the LNA oligonucleotide is a compound of the sequence SEQ ID NO. 1, i.e. the LNA oligonucleotide has a total of 16 nucleotides/LNA nucleotide analogues.

It is noted that subsequence $A_sA_st_sc_sc_sa_st_sg_sg_s{}^{Me}C$ of SEQ ID NO. 28 and subsequence $A_sa_st_sc_sc_sa_st_sg_sg_s{}^{Me}C$ of SEQ ID NO. 1 are indicated as fully phosphorothiolated, cf. subscript "s". Although is it is not currently preferred, it is believed that one, and possibly also two, of the phosphorothioate links may be replaced by other links, in particular phosphorodiester links, without severely compromising the stability of the LNA oligonucleotide. Thus, such variants where one or two of the phosphorothioate links are replaced by, e.g., phosphorodiester links also fall within the intended scope of the present invention.

Illustrative examples of particular (sub)sequences of SEQ ID NOS. 28 and 1 are SEQ ID NOS. 2-20 listed in Table 1.

TABLE 1

LNA oligonucleotides

| SEQ ID NO. | Sequence and design | Design |
|---|---|---|
| 2 | 5'-$^{Me}C_sT_s^{Me}C_sA_sa_st_sc_sc_sa_st_sg_sg_s^{Me}C_sA_sG_sc$-3' | 4-8-3-1 |
| 3 | 5'-$^{Me}CT^{Me}CA_sa_st_sc_sc_sa_st_sg_sg_s^{Me}CAG_sc$-3' | 4-8-3-1 |
| 4 | 5'-$^{Me}CT^{Me}CA_sa_st_sc_sc_sa_st_sg_sg_s^{Me}CAGc$-3' | 4-8-3-1 |
| 5 | 5'-$^{Me}C_sT_s^{Me}C_sA_sa_st_sc_sc_sa_st_sg_sg_s^{Me}C_sA_sg_sc$-3' | 4-8-2-2 |
| 6 | 5'-$c_sT_s^{Me}C_sA_sa_st_sc_sc_sa_st_sg_sg_s^{Me}C_sA_sG_sc$-3' | 1-3-8-3-1 |
| 7 | 5'-$^{Me}CT^{Me}CA_sa_st_sc_sc_sa_st_sg_sg_s^{Me}CAg_sc$-3' | 4-8-2-2 |
| 8 | 5'-$c_sT^{Me}CA_sa_st_sc_sc_sa_st_sg_sg_s^{Me}CAG_sc$-3' | 1-3-8-3-1 |
| 9 | 5'-$^{Me}CT^{Me}CA_sa_st_sc_sc_sa_st_sg_sg_s^{Me}CAgc$-3' | 4-8-2-2 |
| 10 | 5'-$cT^{Me}CA_sa_st_sc_sc_sa_st_sg_sg_s^{Me}CAGc$-3' | 1-3-8-3-1 |
| 11 | 5'-$^{Me}C^{\alpha}_sT^{\alpha}_s^{Me}C^{\alpha}_sA^{\alpha}_sa_st_sc_sc_sa_st_sg_sg_s^{Me}C^{\alpha}_sA^{\alpha}_sG^{\alpha}_sc$-3' | 4-8-3-1 |
| 12 | 5'-$^{Me}C_sT_s^{Me}C_sA^{\alpha}_sa_st_sc_sc_sa_st_sg_sg_s^{Me}C^{\alpha}_sA_sG_sc$-3' | 4-8-3-1 |
| 13 | 5'-$^{Me}C^{\alpha}T^{\alpha Me}C^{\alpha}A^{\alpha}_sa_st_sc_sc_sa_st_sg_sg_s^{Me}C^{\alpha}A^{\alpha}G^{\alpha}_sc$-3' | 4-8-3-1 |
| 14 | 5'-$^{Me}C^{\alpha}T^{\alpha Me}C^{\alpha}A^{\alpha}_sa_st_sc_sc_sa_st_sg_sg_s^{Me}C^{\alpha}A^{\alpha}G^{\alpha}c$-3' | 4-8-3-1 |
| 15 | 5'-$^{Me}C^{\alpha}_sT^{\alpha}_s^{Me}C^{\alpha}_sA^{\alpha}_sa_st_sc_sc_sa_st_sg_sg_s^{Me}C^{\alpha}_sA^{\alpha}_sg_sc$-3' | 4-8-2-2 |
| 16 | 5'-$c_sT^{\alpha}_s^{Me}C^{\alpha}_sA^{\alpha}_sa_st_sc_sc_sa_st_sg_sg_s^{Me}C^{\alpha}_sA^{\alpha}_sG^{\alpha}_sc$-3' | 1-3-8-3-1 |
| 17 | 5'-$^{Me}C^{\alpha}T^{\alpha Me}C^{\alpha}A^{\alpha}_sa_st_sc_sc_sa_st_sg_sg_s^{Me}C^{\alpha}A^{\alpha}g_sc$-3' | 4-8-2-2 |
| 18 | 5'-$c_st^{\alpha Me}C^{\alpha}A^{\alpha}_sa_st_sc_sc_sa_st_sg_sg_s^{Me}C^{\alpha}A^{\alpha}G^{\alpha}_sc$-3' | 1-3-8-3-1 |
| 19 | 5'-$^{Me}C^{\alpha}T^{\alpha Me}C^{\alpha}A^{\alpha}_sa_st_sc_sc_sa_st_sg_sg_s^{Me}C^{\alpha}A^{\alpha}gc$-3' | 4-8-2-2 |
| 20 | 5'-$cT^{\alpha Me}C^{\alpha}A^{\alpha}_sa_st_sc_sc_sa_st_sg_sg_s^{Me}C^{\alpha}A^{\alpha}G^{\alpha}c$-3' | 1-3-8-3-1 |

In Table 1, capital letters (without superscript) designate an β-D-oxy-LNA nucleotide analogue (β-D-oxy-LNA); superscript "α" after a capital letter (e.g. G$^{\alpha}$), however, denote that the LNA nucleotide analogue is an α-L-LNA nucleotide analogue (α-L-oxy-LNA), small letters designate a deoxynucleotide, subscript "s" designates a phosphorothioate link between neighbouring nucleotides/LNA nucleotide analogues, and no subscript between neighbouring nucleotides/LNA nucleotide analogues designates a phosphorodiester link. All LNA-C monomers are 5-methyl-C ($^{Me}C$).

In attractive embodiments, the LNA oligonucleotide comprises a (sub)sequence selected from the group consisting of SEQ ID NOS.: 2, 3, 4, 5, 6, 7, 8, 9, 10, 11, 12, 13, 14, 15, 16, 17, 18, 19, and 20, in particular from the group consisting of SEQ ID NOS. 2, 3, 4, 5, 6, 7, 8, 9, and 10. More particularly, the LNA oligonucleotide is a compound selected from the group consisting of SEQ ID NOS.: 2, 3, 4, 5, 6, 7, 8, 9, 10, 11, 12, 13, 14, 15, 16, 17, 18, 19, and 20, in particular from the group consisting of SEQ ID NOS. 2, 3, 4, 5, 6, 7, 8, 9, and 10.

In a currently most preferred embodiment, the LNA oligonucleotide comprises the (sub)sequence SEQ ID NO. 2. Even more preferably, the LNA oligonucleotide is the compound with SEQ ID NO. 2.

Preparation of the LNA Oligonucleotides

The LNA nucleotide analogue building blocks (β-D-oxy-LNA, β-D-thio-LNA, β-D-amino-LNA and α-L-oxy-LNA) can be prepared following published procedures and references cited therein, see, e.g., WO 03/095467 A1; D. S. Pedersen, C. Rosenbohm, T. Koch (2002) Preparation of LNA Phosphoramidites, Synthesis 6, 802-808; M. D. Sørensen, L. Kværnø, T. Bryld, A. E. Håkansson, B. Verbeure, G. Gaubert, P. Herdewijn, 3. Wengel (2002) α-L-ribo-configured Locked Nucleic Acid (α-l-LNA): Synthesis and Properties, 3. Am. Chem. Soc., 124, 2164-2176; S. K. Singh, R. Kumar, J. Wengel (1998) Synthesis of Novel Bicyclo[2.2.1] Ribonucleosides: 2'-Amino- and 2'-Thio-LNA Monomeric Nucleosides, 3. Org. Chem. 1998, 63, 6078-6079; C. Rosenbohm, S. M. Christensen, M. D. Sørensen, D. S. Pedersen, L. E. Larsen, J. Wengel, T. Koch (2003) Synthesis of 2'-amino-LNA: a new strategy, Org. Biomol. Chem. 1, 655-663; and WO 2004/069991 A2.

The LNA oligonucleotides can be prepared as described in the Examples and in WO 99/14226, WO 00/56746, WO 00/56748, WO 00/66604, WO 00/125248, WO 02/28875, WO 2002/094250 and WO 03/006475. Thus, the LNA oligonucleotides may be produced using the oligomerisation techniques of nucleic acid chemistry well-known to a person of ordinary skill in the art of organic chemistry. Generally, standard oligomerisation cycles of the phosphoramidite approach (S. L. Beaucage and R. P. Iyer, *Tetrahedron,* 1993, 49, 6123; S. L. Beaucage and R. P. Iyer, *Tetrahedron,* 1992, 48, 2223) are used, but e.g. H-phosphonate chemistry, phosphotriester chemistry can also be used.

For some monomers, longer coupling time, and/or repeated couplings and/or use of more concentrated coupling reagents may be necessary or beneficial.

The phosphoramidites employed couple typically with satisfactory >95% step-wise yields. Oxidation of the Phosphorous(III) to Phosphorous(V) is normally done with e.g. iodine/pyridine/H$_2$O. This yields after deprotection the native phosphorodiester internucleoside linkage. In the case that a phosphorothioate internucleoside linkage is prepared a thiolation step is performed by exchanging the normal, e.g. iodine/pyridine/H$_2$O, oxidation used for synthesis of phosphorodiester internucleoside linkages with an oxidation using the ADTT reagent (xanthane hydride (0.01 M in acetonitrile:pyridine 9:1; v/v)). Other thiolation reagents are also possible to use, such as Beaucage and PADS. The phosphorothioate LNA oligonucleotides were efficiently synthesized with stepwise coupling yields >=98%.

LNA oligonucleotides comprising β-D-amino-LNA, β-D-thio-LNA, and/or α-L-LNA can also efficiently be synthesized with step-wise coupling yields ≧98% using the phosphoramidite procedures.

Purification of LNA oligonucleotides was can be accomplished using disposable reversed phase purification cartridges and/or reversed phase HPLC and/or precipitation from ethanol or butanol. Capillary gel electrophoresis, reversed phase HPLC, MALDI-MS, and ESI-MS were used to verify the purity of the synthesized LNA oligonucleotides.

Salts

The LNA oligonucleotides can be employed in a variety of pharmaceutically acceptable salts. As used herein, the term refers to salts that retain the desired biological activity of the LNA oligonucleotide and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine; or combinations, e.g., a zinc tannate salt or the like.

Such salts are formed, from the LNA oligonucleotides which possess phosphorodiester group and/or phosphorothioate groups, and are, for example, salts with suitable bases. These salts include, for example, nontoxic metal salts which are derived from metals of groups Ia, Ib, IIa and IIb of the Periodic System of the elements, in particular suitable alkali metal salts, for example lithium, sodium or potassium salts, or alkaline earth metal salts, for example magnesium or calcium salts. They furthermore include zinc and ammonium salts and also salts which are formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)-amine or tri-(2-hydroxyethyl)amine, or N-methyl-D-glucamine, or quaternary ammonium compounds such as tetrabutylammonium salts. Lithium salts, sodium salts, magnesium salts, zinc salts or potassium salts are preferred, with sodium salts being particularly preferred.

Prodrugs

In one embodiment, the LNA oligonucleotide may be in the form of a pro-drug. Oligonucleotides are by virtue negatively charged ions. Due to the lipophilic nature of cell membranes, the cellular uptake of oligonucleotides is reduced compared to neutral or lipophilic equivalents. This polarity "hindrance" can be avoided by using the pro-drug approach (see e.g. Crooke, R. M. (1998) in Crooke, S. T. *Antisense research and Application*. Springer-Verlag, Berlin, Germany, vol. 131, pp. 103-140). In this approach, the LNA oligonucleotides are prepared in a protected manner so that the LNA oligonucleotides are neutral when it is administered. These protection groups are designed in such a way that they can be removed when the LNA oligonucleotide is taken up by the cells. Examples of such protection groups are S-acetylthioethyl (SATE) or S-pivaloylthioethyl (t-butyl-SATE). These protection groups are nuclease resistant and are selectively removed intracellulary.

Conjugates

In the present context, the term "conjugate" is intended to indicate a heterogenous molecule formed by the covalent attachment of an LNA oligonucleotide as described herein (i.e. a compound comprising a sequence of nucleosides and LNA nucleoside analogues) to one or more non-nucleotide or non-polynucleotide moieties.

Thus, the LNA oligonucleotides may, e.g., be conjugated or form chimera with non-nucleotide or non-polynucleotide moieties including Peptide Nucleic Acids (PNA), proteins (e.g. antibodies for a target protein), macromolecules, low molecular weight drug substances, fatty acid chains, sugar residues, glycoproteins, polymers (e.g. polyethylene glycol), micelle-forming groups, antibodies, carbohydrates, receptor-binding groups, steroids such as cholesterol, polypeptides, intercalating agents such as an acridine derivative, a long-chain alcohol, a dendrimer, a phospholipid and other lipophilic groups or combinations thereof, etc., just as the LNA oligonucleotides may be arranged in dimeric or dendritic structures. The LNA oligonucleotides or conjugates may also be conjugated or further conjugated to active drug substances, for example, aspirin, ibuprofen, a sulfa drug, an antidiabetic, an antibacterial agent, a chemotherapeutic compound or an antibiotic.

Conjugating in this way confers advantageous properties with regard to the pharmacokinetic characteristics of the LNA oligonucleotides. In particular, conjugating in this way achieves increased cellular uptake.

In one embodiment, an LNA oligonucleotide is linked to ligands so as to form a conjugate, said ligands intended to increase the cellular uptake of the conjugate relative to the antisense LNA oligonucleotides. This conjugation can take place at the terminal positions 5'/3'-OH but the ligands may also take place at the sugars and/or the bases. In particular, the growth factor to which the antisense LNA oligonucleotide may be conjugated, may comprise transferrin or folate. Transferrin-polylysine-oligonucleotide complexes or folate-polylysine-oligonucleotide complexes may be prepared for uptake by cells expressing high levels of transferrin or folate receptor. Other examples of conjugates/ligands are cholesterol moieties, duplex intercalators such as acridine, poly-L-lysine, "end-capping" with one or more nuclease-resistant linkage groups such as phosphoromonothioate, and the like.

The preparation of transferrin complexes as carriers of oligonucleotide uptake into cells is described by Wagner et al., *Proc. Natl. Acad. Sci. USA* 87, 3410-3414 (1990). Cellular delivery of folate-macromolecule conjugates via folate receptor endocytosis, including delivery of an antisense oligonucleotide, is described by Low et al., U.S. Pat. No. 5,108, 921. Also see, Leamon et al., *Proc. Natl. Acad. Sci.* 88, 5572 (1991).

Pharmaceutical Composition

It should be understood that the invention relates to pharmaceutical compositions comprising an LNA oligonucleotide or a conjugate as defined above, and a pharmaceutically acceptable carrier, e.g. an aqueous carrier. The pharmaceutical composition is preferably suitable for injection.

Directions for the preparation of pharmaceutical compositions can be found in "Remington: The Science and Practice of Pharmacy" by Alfonso R. Gennaro, and in the following.

Pharmaceutically acceptable carriers, such as binding agents and adjuvants, are part of the pharmaceutical composition. Capsules, tablets and pills etc. may contain for example the following compounds: microcrystalline cellulose, gum or gelatin as binders; starch or lactose as excipients; stearates as lubricants; various sweetening or flavouring agents. For capsules the dosage unit may contain a liquid carrier like fatty oils, Likewise coatings of sugar or enteric agents may be part of the dosage unit. The pharmaceutical composition may also be emulsions of the active pharmaceutical ingredients (including the LNA oligonucleotide) and a lipid forming a micellular emulsion.

An LNA oligonucleotide may be mixed with any material that does not impair the desired action, or with materials that supplement the desired action. These could include other drugs including other nucleoside compounds.

For parenteral, subcutaneous, intradermal or topical administration the formulation may include a sterile diluent (e.g. water), buffer(s), regulators of tonicity and ionic strength and antibacterials. The active compound may be prepared with carriers that facilitates uptake, protect against degradation or protect against immediate elimination from the body, including implants or microcapsules with controlled release properties. For intravenous administration, the preferred carriers are physiological saline (0.9%) or phosphate buffered saline.

Preferably, an LNA oligonucleotide is included in a unit formulation such as in a pharmaceutically acceptable carrier or diluent in an amount sufficient to deliver to a patient a therapeutically effective amount without causing serious side effects in the treated patient.

In preferred embodiments of the pharmaceutical compositions, the LNA oligonucleotide is formulated in an aqueous carrier, in particular an aqueous carrier comprising a buffer for keeping the pH in the range of 4.0-8.5, and having an ionic strength of 20-2000 mM.

The term "aqueous carrier" means that the pharmaceutical composition in question is in liquid form, and that the liquid carrier predominantly is composed of water, i.e. that at least 80% (w/w), or at least 90% (w/w), or even at least 95% (w/w), of the carrier consists of water. Other liquid ingredients may also be used, e.g. ethanol, DMSO, ethylene glycol, etc.

The aqueous carrier preferably comprises a buffer for keeping the pH in the range of 4.0-8.5. Preferably, the buffer will keep the pH in the range of 5.0-8.0, such as in the range of 6.0-7.5.

The ionic strength/tonicity of the pharmaceutical composition is also of importance. Thus, typically, the liquid pharmaceutical composition has an ionic strength of in the range of 20-2000 mM, such as in the range of 50-1500 mM, or in the range of 100-1000 mM.

A first main aspect of the present invention relates to a liquid pharmaceutical composition comprising an LNA oligonucleotide in an aqueous carrier, said LNA oligonucleotide having a total of 12-20 nucleotides/LNA nucleotide analogues and comprising the following (sub)sequence:

$$5'-(^{Me}\underline{C}_x)(T_x)^{Me}C_xA_s\underline{A}_st_sc_sc_sa_st_sg_sg_s{}^{Me}C_xA_x(\underline{G}_x)(c)-3',$$ (SEQ ID NO. 28)

preferably having a total of 16-20 nucleotides/LNA nucleotide analogues and comprising the following (sub)sequence:

$$5'-{}^{Me}\underline{C}_xT_x{}^{Me}C_xA_sa_st_sc_sc_sa_st_sg_sg_s{}^{Me}C_xA_s\underline{G}_xc-3'$$ (SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues; and said aqueous carrier comprising a buffer for keeping the pH in the range of 4.0-8.5, and having an ionic strength of 20-2000 mM.

A second main aspect of the present invention relates to a liquid pharmaceutical composition comprising a conjugate in an aqueous carrier, said conjugate consisting of an LNA oligonucleotide and at least one non-nucleotide/non-polynucleotide moiety covalently attached to said oligonucleotide, said LNA oligonucleotide having a total of 12-20 nucleotides/LNA nucleotide analogues and comprising the following (sub)sequence:

$$5'-(^{Me}\underline{C}_x)(T_x)^{Me}C_xA_s\underline{A}_st_sc_sc_sa_st_sg_sg_s{}^{Me}C_xA_x(\underline{G}_x)(c)-3',$$ (SEQ ID NO. 28)

preferably having a total of 16-20 nucleotides/LNA nucleotide analogues and comprising the following (sub)sequence:

$$5'-{}^{Me}\underline{C}_xT_x{}^{Me}C_xA_sa_st_sc_sc_sa_st_sg_sg_s{}^{Me}C_xA_s\underline{G}_xc-3'$$ (SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues; and said aqueous carrier comprising a buffer for keeping the pH in the range of 4.0-8.5, and having an ionic strength of 20-2000 mM.

The first and second main aspects are advantageously combined with the specification and preferences with respect to the LNA oligonucleotide, the conjugate and the pharmaceutical composition given further above. The following embodiments are believed to fully represent the benefits of the invention.

In one embodiment, the LNA nucleotide analogues are selected from β-D-oxy-LNA, β-D-thio-LNA and β-D-amino-LNA, or from β-D-oxy-LNA and α-L-oxy-LNA, in particular all LNA nucleotide analogues are β-D-oxy-LNA.

In a further embodiment, which may be combined with the foregoing, the LNA oligonucleotide has a total of 16-19, such as 16-18, or 16-17, in particular 16, nucleotides/LNA nucleotide analogues. Alternatively, the LNA oligonucleotide has a total of 12-18, such 13-18, or 14-17, in particular 14 or 15, nucleotides/LNA nucleotide analogues.

In a still further embodiment, which may be combined with the foregoing, the LNA oligonucleotide comprises a (sub) sequence selected from the group consisting of SEQ ID NOS.: 2, 3, 4, 5, 6, 7, 8, 9, 10, 11, 12, 13, 14, 15, 16, 17, 18, 19, and 20, in particular from the group consisting of SEQ ID NOS. 2, 3, 4, 5, 6, 7, 8, 9, and 10. More particular, the LNA oligonucleotide is a compound selected from the group consisting of SEQ ID NOS.: 2, 3, 4, 5, 6, 7, 8, 9, 10, 11, 12, 13, 14, 15, 16, 17, 18, 19, and 20, in particular from the group consisting of SEQ ID NOS. 2, 3, 4, 5, 6, 7, 8, 9, and 10. Even more preferable, the LNA oligonucleotide comprises the (sub)sequence SEQ ID NO. 2, and most preferable, the LNA oligonucleotide is the compound with SEQ ID NO. 2.

In an even still further embodiment, which may be combined with the foregoing, the composition further comprises at least one taxane compound (see further below under "Combination drug" for further details). In particular, the weight ratio between the taxane compound(s) and the LNA oligonucleotide (LNA oligonucleotide part of the conjugate) in said composition is in the range of 50:1 to 1:25. For the second aspect, it may be preferred if the at least one non-nucleotide/non-polynucleotide moiety comprises a taxane compound.

Combination Drug

The pharmaceutical composition may also comprise a further agent selected from the groups consisting of chemotherapeutic compounds, anti-inflammatory compounds, antiviral compounds, cytostatic compounds, anti-angiogenetic compounds, anti-proliferative compounds, pro-apoptotic compounds, signal transduction modulators, and kinase inhibitors.

In an interesting variant, the further agent is at least one chemotherapeutic compound. Suitable examples of such chemotherapeutic compound are those selected from the group consisting of adrenocorticosteroids, such as prednisone, dexamethasone or decadron; altretamine (hexylen, hexamethylmelamine (HMM)); amifostine (ethyol); aminoglutethimide (cytadren); amsacrine (M-AMSA); anastrozole (arimidex); androgens, such as testosterone; asparaginase (elspar); bacillus calmette-gurin; bicalutamide (casodex); bleomycin (blenoxane); busulfan (myleran); carboplatin (paraplatin); carmustine (BCNU, BiCNU); chlorambucil (leukeran); chlorodeoxyadenosine (2-CDA, cladribine, leustatin); cisplatin (platinol); cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etopside (VP-16, VePesid, etopophos); fludarabine (fludara); flutamide (eulexin); 5-FUDR (floxuridine); 5-fluorouracil (5-FU); gemcitabine (gemzar); goserelin (zodalex); herceptin (trastuzumab); hydroxyurea (hydrea); idarubicin (idamycin); ifosfamide; IL-2 (proleukin, aldesleukin); interferon alpha (intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); mitomycin-C (mutamucin); mitoxantrone (novantrone); octreotide (sandostatin); pentostatin (2-deoxycoformycin, nipent); plicamycin (mithramycin, mithracin); prorocarbazine (matulane); streptozocin; tamoxifin (nolvadex); Taxol (paclitaxel); teniposide (vumon, VM-26); thiotepa; topotecan (hycamtin); tretinoin (vesanoid, all-trans retinoic acid); vinblastine (valban); vincristine (oncovin) and vinorelbine (navelbine).

In one variant, the present invention provides pharmaceutical compositions containing (a) one or more LNA oligonucleotides and (b) one or more other chemotherapeutic compounds which function by a non-antisense mechanism. When used with the LNA oligonucleotides, such chemotherapeutic compounds may be used individually (e.g. mithramycin and oligonucleotide), sequentially (e.g. mithramycin and oligonucleotide for a period of time followed by another agent and oligonucleotide), or in combination with one or more other such chemotherapeutic compounds or in combination with radiotherapy. All chemotherapeutic compounds known to a person skilled in the art including those explicitly mentioned above are here incorporated as combination treatments with compound according to the invention.

In one preferred embodiment, the pharmaceutical composition is administered in combination with a taxane compound.

The term "taxane compound" is intended to encompass paclitaxel (Taxol®), paclitaxel derivatives, docetaxel, taxotere, modified taxanes, and taxoid analogues. Paclitaxel (Taxol®) is a diterpene isolated from the bark of the Western (Pacific) yew, *Taxus brevifolia* and is representative of a class of therapeutic agents having a taxane ring system. Paclitaxel and its analogs have been produced by partial synthesis from 10-deacetylbaccatin III, a precursor obtained from yew needles and twigs, and by total synthesis. See Holton, et al., J. Am. Chem. Soc. 116:1597-1601 (1994) and Nicolaou, et al., Nature 367:630 (1994). Paclitaxel has demonstrated efficacy in several human tumours in clinical trials. See McGuire, et al., Ann. Int. Med. 111:237-279 (1989); Holmes, et al., J. Natl. Cancer Inst. 83:1797-1805 (1991); Kohn et al., J. Natl. Cancer Inst. 86:18-24 (1994); and Kohn, et al., American Society for Clinical Oncology 12 (1993). The modified taxane or taxoid analogs are those compounds having a taxane ring bearing modified side chains. A number of these analogs have improved properties, such as greater water solubility and stability than that of naturally occurring paclitaxel. These analogs are known to those skilled in the art and are disclosed, for example, in U.S. Pat. Nos. 5,278,324; 5,272,171; 5,254,580; 5,250,683; 5,248,796; and 5,227,400, the disclosures of which are incorporated herein by reference. Paclitaxel and taxotere can be prepared by the methods in WO 93/18210, EP 0 253 739, EP 0 253 739, and WO 92/09589, the disclosures of which are incorporated herein by reference. In particular embodiments, the taxane compound is paclitaxel or taxotere.

The weight ratio between the taxane compound(s) and the LNA oligonucleotide in said composition is typically in the range of 50:1 to 1:25, such as in the range of 25:1 to 1:25, or in the range of 10:1 to 1:25, or in the range of 1:1 to 1:25, or in the range of 50:1 to 1:10, or in the range of 1:1 to 1:50, or in the range of 25:1 to 1:10.

Hence, a third aspect of the present invention relates to a pharmaceutical composition comprising at least one taxane compound and an LNA oligonucleotide in a pharmaceutically acceptable carrier, said LNA oligonucleotide having a total of 12-20 nucleotides/LNA nucleotide analogues and comprising the following (sub)sequence:

(SEQ ID NO. 28)
5'-($^{Me}\underline{C}_x$)($T_x$)$^{Me}C_xA_s\underline{A}_st_sc_sc_sa_st_sg_sg_s^{Me}C_xA_x(\underline{G}_x)$(c)-3', preferably having a total of 16-20 nucleotides/LNA nucleotide analogues and comprising the following (sub)sequence:

(SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues; and
wherein the weight ratio between the taxane compound(s) and the LNA oligonucleotide in said composition is in the range of 50:1 to 1:25.

A fourth main aspect of the present invention relates to a pharmaceutical composition comprising at least one taxane compound and a conjugate in a pharmaceutically acceptable carrier, said conjugate consisting of an LNA oligonucleotide and at least one non-nucleotide/non-polynucleotide moiety covalently attached to said oligonucleotide, said LNA oligonucleotide having a total of 12-20 nucleotides/LNA nucleotide analogues and comprising the following (sub)sequence:

(SEQ ID NO. 28)

preferably having a total of 16-20 nucleotides/LNA nucleotide analogues and comprising the following (sub)sequence:

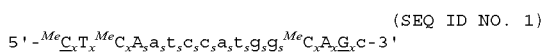
(SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues; and
wherein the weight ratio between the taxane compound(s) and the LNA oligonucleotide part of the conjugate in said composition is in the range of 50:1 to 1:25.

The third and fourth main aspects are advantageously combined with the specification and preferences with respect to the LNA oligonucleotide, the conjugate and the pharmaceutical composition given further above. The following embodiments are believed to fully represent the benefits of the invention.

In one embodiment, the LNA nucleotide analogues are selected from β-D-oxy-LNA, β-D-thio-LNA and β-D-amino-LNA, or from β-D-oxy-LNA and α-L-oxy-LNA, in particular all LNA nucleotide analogues are β-D-oxy-LNA.

In a further embodiment, which may be combined with the foregoing, the LNA oligonucleotide has a total of 16-19, such as 16-18, or 16-17, in particular 16, nucleotides/LNA nucleotide analogues. Alternatively, the LNA oligonucleotide has a total of 12-18, such 13-18, or 14-17, in particular 14 or 15, nucleotides/LNA nucleotide analogues.

In a still further embodiment, which may be combined with the foregoing, the LNA oligonucleotide comprises a (sub) sequence selected from the group consisting of SEQ ID NOS.: 2, 3, 4, 5, 6, 7, 8, 9, 10, 11, 12, 13, 14, 15, 16, 17, 18, 19, and 20, in particular from the group consisting of SEQ ID NOS. 2, 3, 4, 5, 6, 7, 8, 9, and 10. More particular, the LNA oligonucleotide is a compound selected from the group consisting of SEQ ID NOS.: 2, 3, 4, 5, 6, 7, 8, 9, 10, 11, 12, 13, 14, 15, 16, 17, 18, 19, and 20, in particular from the group consisting of SEQ ID NOS. 2, 3, 4, 5, 6, 7, 8, 9, and 10. Even more preferable, the LNA oligonucleotide comprises the (sub)sequence SEQ ID NO. 2, and most preferable, the LNA oligonucleotide is the compound with SEQ ID NO. 2.

In an even still further embodiment, which may be combined with the foregoing, the LNA oligonucleotide (or conjugate) and taxane compound(s) are present in an aqueous carrier. Preferably, the aqueous carrier comprises a buffer for keeping the pH in the range of 4.0-8.5, and has an ionic strength of 20-2000 mM (see also above for further details about the buffer).

For the fourth aspect, it may be preferred if the at least one non-nucleotide/non-polynucleotide moiety comprises a taxane compound.

In a further embodiment, pharmaceutical compositions of the invention may contain one or more LNA oligonucleotides and one or more additional antisense compounds targeted to a second nucleic acid target. Two or more combined compounds may be used together or sequentially.

Furthermore, the medicaments comprising the LNA oligonucleotides may be used in combination with radiotherapy, etc., see also the Experimentals section.

Method of Treatment

The pharmaceutical compositions are particularly relevant for the treatment of cancer.

The pharmaceutical compositions and methods of the invention are preferably employed for treatment or prophylaxis against diseases caused by cancer, particularly for treatment of cancer which may occur in tissue such as lung, breast, colon, prostate, pancreas, lung, liver, thyroid, kidney, brain, testes, stomach, intestine, bowel, spinal cord, sinuses, bladder, urinary tract, ovaries, head and neck, hematologic, skin, gastric, or bone cancer.

The invention described herein encompasses a method of preventing or treating cancer comprising a therapeutically effective amount of a Survivin modulating LNA oligonucleotide, including but not limited to high doses of the LNA oligonucleotide, to a human in need of such therapy. The invention further encompasses the use of a short period of administration of a Survivin modulating LNA oligonucleotide. Normal, non-cancerous cells divide at a frequency characteristic for the particular cell type. When a cell has been transformed into a cancerous state, uncontrolled cell proliferation and reduced cell death results, and therefore, promiscuous cell division or cell growth is a hallmark of a cancerous cell type. Examples of types of cancer, include, but are not limited to, non-Hodgkin's lymphoma, Hodgkin's lymphoma, leukemia (e.g., acute leukemia such as acute lymphocytic leukemia, acute myelocytic leukemia, chronic myeloid leukemia, chronic lymphocytic leukemia, multiple myeloma), colon carcinoma, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system, tumours (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumour, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma), heavy chain disease, metastases, or any disease or disorder characterized by uncontrolled or abnormal cell growth.

Particularly relevant cancer diseases are those selected from acute myelocytic leukemia, diffuse B-cell lymphoma, acute lymphocytic leukemia, hepatic cancer, renal cancer, urinary tract cancer, and colorectal cancer.

The term "carcinoma" is intended to indicate a malignant tumour of epithelial origin. Epithelial tissue covers or lines the body surfaces inside and outside the body. Examples of epithelial tissue are the skin and the mucosa and serosa that line the body cavities and internal organs, such as intestines, urinary bladder, uterus, etc. Epithelial tissue may also extend into deeper tissue layers to form glands, such as mucus-secreting glands. The term "sarcoma" is intended to indicate a malignant tumour growing from connective tissue, such as cartilage, fat, muscles, tendons and bones. The term "giloma", when used herein, is intended to cover a malignant tumour originating from glial cells.

The compositions of the present invention are believed to be particularly relevant for the treatment of tumour-related cancer forms. Such treatment may be combined with radiotherapy.

A fifth main aspect of the present invention relates to the use of an LNA oligonucleotide for the preparation of a pharmaceutical composition for the treatment a mammal, in particular a human, suffering from or susceptible to a cancer disease, said LNA oligonucleotide having a total of 12-20 nucleotides/LNA nucleotide analogues and comprising the following (sub)sequence:

(SEQ ID NO. 28)
5'-($^{Me}\underline{C}_x$)($T_x$)$^{Me}C_xA_x\underline{A}_xt_sc_sc_sa_st_sg_sg_s^{Me}C_xA_x(\underline{G}_x)$(c)-3', preferably having a total of 16-20 nucleotides/LNA nucleotide analogues and comprising the following (sub)sequence:

(SEQ ID NO. 1)
5'-$^{Me}\underline{C}_xT_x^{Me}C_xA_sa_st_sc_sc_sa_st_sg_sg_s^{Me}C_xA_s\underline{G}_xc$-3' wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues.

A sixth main aspect of the present invention relates to the use of a conjugate, said conjugate consisting of an LNA oligonucleotide and at least one non-nucleotide/non-polynucleotide moiety covalently attached to said oligonucleotide, for the preparation of a pharmaceutical composition for the treatment a mammal, in particular a human, suffering from or susceptible to a cancer disease, said LNA oligonucleotide having a total of 12-20 nucleotides/LNA nucleotide analogues and comprising the following (sub)sequence:

(SEQ ID NO. 28)
5'-($^{Me}\underline{C}_x$)($T_x$)$^{Me}C_xA_x\underline{A}_xt_sc_sc_sa_st_sg_sg_s^{Me}C_xA_x(\underline{G}_x)$(c)-3', preferably having a total of 16-20 nucleotides/LNA nucleotide analogues and comprising the following (sub)sequence:

(SEQ ID NO. 1)
5'-$^{Me}\underline{C}_xT_x^{Me}C_xA_sa_st_sc_sc_sa_st_sg_sg_s^{Me}C_xA_s\underline{G}_xc$-3' wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues.

A seventh main aspect of the present invention relates to a method of treating a mammal, in particular a human, suffering from or susceptible to a cancer disease, the method comprising the step of administering to the mammal one or more therapeutically effective doses of a first pharmaceutical composition comprising an LNA oligonucleotide, said LNA oligonucleotide having a total of 12-20 nucleotides/LNA nucleotide analogues and comprising the following (sub)sequence:

(SEQ ID NO. 28)
5'-($^{Me}\underline{C}_x$)($T_x$)$^{Me}C_xA_x\underline{A}_xt_sc_sc_sa_st_sg_sg_s^{Me}C_xA_x(\underline{G}_x)$(c)-3', preferably having a total of 16-20 nucleotides/LNA nucleotide analogues and comprising the following (sub)sequence:

(SEQ ID NO. 1)
5'-$^{Me}\underline{C}_xT_x^{Me}C_xA_sa_st_sc_sc_sa_st_sg_sg_s^{Me}C_xA_s\underline{G}_xc$-3' wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues.

An eighth seventh main aspect of the present invention relates to a method of treating a mammal, in particular a human, suffering from or susceptible to a cancer disease, the method comprising the step of administering to the mammal one or more therapeutically effective doses of a first pharmaceutical composition comprising a conjugate, said conjugate consisting of an LNA oligonucleotide and at least one non-nucleotide/non-polynucleotide moiety covalently attached to said LNA oligonucleotide, said LNA oligonucleotide having a total of 12-20 nucleotides/LNA nucleotide analogues and comprising the following (sub)sequence:

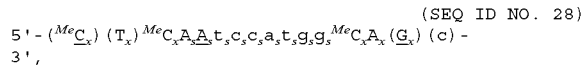
(SEQ ID NO. 28)

preferably having a total of 16-20 nucleotides/LNA nucleotide analogues and comprising the following (sub)sequence:

(SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues.

The fifth, sixth, seventh and eight main aspects are advantageously combined with the specification and preferences with respect to the LNA oligonucleotide, the conjugate and the pharmaceutical composition given further above. Hence, the compositions referred to in the fifth, sixth, seventh and eight main aspect are preferably as defined for the pharmaceutical compositions defined further above under "Pharmaceutical composition" and "Combination drug". The following embodiments are further believed to fully represent the benefits of the invention.

The disease referred to may be any of the ones defined further above, however preferably selected from the group consisting of acute myelocytic leukemia, diffuse B-cell lymphoma, acute lymphocytic leukemia, hepatic cancer, renal cancer, urinary tract cancer, and colorectal cancer.

In one embodiment, the LNA nucleotide analogues are selected from β-D-oxy-LNA, β-D-thio-LNA and β-D-amino-LNA, or from β-D-oxy-LNA and α-L-oxy-LNA, in particular all LNA nucleotide analogues are β-D-oxy-LNA.

In a further embodiment, which may be combined with the foregoing, the LNA oligonucleotide has a total of 16-19, such as 16-18, or 16-17, in particular 16, nucleotides/LNA nucleotide analogues. Alternatively, the LNA oligonucleotide has a total of 12-18, such 13-18, or 14-17, in particular 14 or 15, nucleotides/LNA nucleotide analogues.

In a still further embodiment, which may be combined with the foregoing, the LNA oligonucleotide comprises a (sub)sequence selected from the group consisting of SEQ ID NOS.: 2, 3, 4, 5, 6, 7, 8, 9, 10, 11, 12, 13, 14, 15, 16, 17, 18, 19, and 20, in particular from the group consisting of SEQ ID NOS. 2, 3, 4, 5, 6, 7, 8, 9, and 10. More particular, the LNA oligonucleotide is a compound selected from the group consisting of SEQ ID NOS.: 2, 3, 4, 5, 6, 7, 8, 9, 10, 11, 12, 13, 14, 15, 16, 17, 18, 19, and 20, in particular from the group consisting of SEQ ID NOS. 2, 3, 4, 5, 6, 7, 8, 9, and 10. Even more preferable, the LNA oligonucleotide comprises the (sub)sequence SEQ ID NO. 2, and most preferable, the LNA oligonucleotide is the compound with SEQ ID NO. 2.

In an even still further embodiment of the fifth and sixth main aspects, which may be combined with the foregoing, the composition further comprises at least one taxane compound (see further above under "Combination drug" for further details). In particular, the weight ratio between the taxane compound(s) and the LNA oligonucleotide (LNA oligonucleotide part of the conjugate) in said composition is in the range of 50:1 to 1:25. For the second aspect, it may be preferred if the at least one non-nucleotide/non-polynucleotide moiety comprises a taxane compound.

In an even still further embodiment of the seventh and eighth, which may be combined with the foregoing, the at least one taxane compound (see further above under "Combination drug" for further details) is administered in combination with the LNA oligonucleotide or conjugate. In particular, the weight ratio between the taxane compound(s) and the LNA oligonucleotide (LNA oligonucleotide part of the conjugate) administered is in the range of 50:1 to 1:25. For the eighth aspect, it may be preferred if the at least one non-nucleotide/non-polynucleotide moiety comprises a taxane compound.

Referring to the before-mentioned embodiment, the taxane compound(s) may be present in the first pharmaceutical composition comprising the LNA oligonucleotide (or the conjugate). In this instance, the weight ratio between the taxane compound(s) and the LNA oligonucleotide (or the LNA oligonucleotide part of the conjugate) in said composition is preferably in the range of 50:1 to 1:25. Alternatively, the taxane compound(s) may be present in a second pharmaceutical composition not comprising the LNA oligonucleotide (or the conjugate). In this instance, the first pharmaceutical composition and the second pharmaceutical composition may be administered concomitantly, or alternatively, the first pharmaceutical composition and the second pharmaceutical composition are administered sequentially.

In an even still further embodiment, which may be combined with the foregoing, the LNA oligonucleotide (or the conjugate) and any taxane compound(s) are present in an aqueous carrier. Preferably, the aqueous carrier comprises a buffer for keeping the pH in the range of 4.0-8.5, and has an ionic strength of 20-2000 mM (see also above for further details about the buffer).

For the sixth and eight main aspect, it may be preferred if the at least one non-nucleotide/non-polynucleotide moiety comprises a taxane compound.

Kits

The present invention also provides various kits useful in the medical treatment of a patient in need thereof.

In one variant, the kit comprises a set useful for combination treatment, i.e. treatment with an LNA oligonucleotide (or conjugate thereof) and one or more taxane compounds.

Hence, a ninth main aspect of the present invention relates to a kit comprising (a) a first component containing one or more injectable solution doses of an LNA oligonucleotide, and (b) a second component containing one or more injectable solutions of one or more taxane compounds;

wherein said LNA oligonucleotide having a total of 12-20 nucleotides/LNA nucleotide analogues and comprising the following (sub)sequence:

(SEQ ID NO. 28)

preferably having a total of 16-20 nucleotides/LNA nucleotide analogues and comprising the following (sub)sequence:

(SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues; and wherein the weight ratio between the at least one taxane compound in one solution of the second component and the at least one LNA oligonucleotide in one dose of the first component is in the range of 50:1 to 1:25, and/or wherein the injectable solution doses of the LNA oligonucleotide comprise a buffer for keeping the pH in the range of 4.0-8.5, and having an ionic strength of 20-2000 mM. In a preferred embodiment, the buffer, e.g. saline or buffered saline, has a pH of 6.0-8.0 and an ionic strength of 100-500 mM. In a most preferred embodiment, the saline or buffered saline has a pH of 7.0-8.0 and an ionic strength of 120-250 mM.

A similar kit comprising a conjugate of an LNA oligonucleotide and a non-nucleotide/non-polynucleotide moiety also constitutes an aspect of the invention, mutatis mutandis.

It should be understood, that the injectable solution doses of the LNA oligonucleotide (or conjugate of an LNA oligonucleotide and a non-nucleotide/non-polynucleotide moiety) and the taxane compounds preferably are as defined further above under "Pharmaceutical composition" and "Combination drug", respectively.

If the pharmaceutical composition in liquid form is under risk of being subjected to conditions which will compromise the stability of the LNA oligonucleotide, it may be preferred to produce the finished product containing the LNA oligonucleotide in a solid form, e.g. as a freeze dried material, and store the product is such solid form. The product may then be reconstituted (e.g. dissolved or suspended) prior to administration.

Hence, a tenth main aspect of the invention relates to a kit comprising (a) a first component containing an LNA oligonucleotide is solid form, and (b) a second component containing saline or a buffer solution (e.g. buffered saline) adapted for reconstitution (e.g. dissolution or suspension) of said LNA oligonucleotide, preferably said buffer solution has a pH in the range of 4.0-8.5, and an ionic strength of 20-2000 mM;

wherein said LNA oligonucleotide having a total of 12-20 nucleotides/LNA nucleotide analogues and comprising the following (sub)sequence:

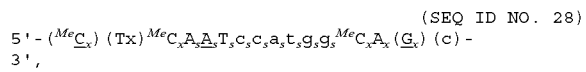

(SEQ ID NO. 28)

preferably having a total of 16-20 nucleotides/LNA nucleotide analogues and comprising the following (sub)sequence:

(SEQ ID NO. 1)

wherein capital letters designate an LNA nucleotide analogue selected from β-D-oxy-LNA, β-D-thio-LNA, β-D-amino-LNA and α-L-oxy-LNA, small letters designate a deoxynucleotide, underline designates either an LNA nucleotide analogue as defined above or a deoxynucleotide, subscript "s" designates a phosphorothioate link between neighbouring nucleotides/LNA nucleotide analogues, and subscript "x" designates either a phosphorothioate link or a phosphorodiester link between neighbouring nucleotides/LNA nucleotide analogues.

The above-mentioned kits preferably also include a written guideline for combining the first and second components.

Administration

The pharmaceutical compositions of the present invention may be administered in a number of ways depending upon whether local or systemic treatment is desired and upon the area to be treated. Administration may be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal or intraventricular, administration. In one embodiment, the LNA oligonucleotide is administered intravenous, intraperitoneal, orally, topically or as a bolus injection or administered directly in to the target organ.

It is currently believed that the most appropriate administration form is by intravenous infusions or oral.

Dosage

Dosing is dependent on severity and responsiveness of the disease state to be treated, and the course of treatment lasting from several days to several months, or until a cure is effected or a diminution of the disease state is achieved. Optimal dosing schedules can also be assessed by measurements of drug in the body of the patient or by surrogate markers.

Optimum dosages may vary depending on the relative potency of individual oligonucleotides. Generally, it can be estimated based on $EC_{50}$s found to be effective in in vitro and in vivo animal models. In general, dosage is from 0.01 μg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state. It is currently believed that the most relevant doses are 0.01 mg to 100 mg, such as 0.1 mg to 40 mg, or 0.5 mg to 10 mg, per kg of body weight. Such doses may be given once daily, but more preferably less frequent, e.g. 1-3 times per week, for a period of 1-4 weeks. Maintenance therapy may be continued, e.g. 1-4 times per month or even less frequent such 1-10 times per year.

Without being bound to any particular theory, it is envisaged that the combined effect (and potentially synergistic effect) of a chemotherapeutic compound and an LNA oligonucleotide according to the invention will render it possible to reduce the dosage of the chemotherapeutic compound or the LNA oligonucleotide, or both.

Further Uses

The LNA oligonucleotides of the present invention can also be utilized for as research reagents for diagnostics, therapeutics and prophylaxis. In research, the antisense LNA oligonucleotides may be used to specifically inhibit the synthesis of Survivin protein in cells and experimental animals thereby facilitating functional analysis of the target or an appraisal of its usefulness as a target for therapeutic intervention. In diagnostics, the antisense oligonucleotides may be used to detect and quantitate Survivin expression in cell and tissues by Northern blotting, in-situ hybridisation or similar techniques. For therapeutics, an animal or a human, suspected of having a disease or disorder, which can be treated by modulating the expression of Survivin is treated by administering antisense LNA oligonucleotides in accordance with this invention.

Further provided are methods of treating an animal particular mouse and rat and treating a human, suspected of having or being prone to a disease or condition, associated with expression of Survivin by administering a therapeutically or prophylactically effective amount of one or more of the antisense LNA oligonucleotides or conjugates.

The invention further provides a method of modulating the expression of Survivin in cells or tissue, the method comprising contacting said cells or tissue with an LNA oligonucleotide or a conjugate as defined herein, in particular a pharmaceutical composition as defined herein, so that expression of Survivin is modulated.

Still further, the invention provides a method of modulating expression of a gene involved in a cancer disease comprising contacting the gene or RNA from the gene with an LNA oligonucleotide or a conjugate as defined herein, in particular a pharmaceutical composition as defined herein, whereby gene expression is modulated. The gene is preferably the Survivin gene.

A further aspect of the present invention relates to a method of inducing cell apoptosis comprising contacting the cell or RNA from the cell with a pharmaceutical composition as defined herein, whereby cell apoptosis is induced. The induction of apoptosis may be in vitro or in vivo. The induction may be provoked in a cellular assay or within a tissue sample or within the living mammal.

A further aspect of the present invention relates to a method of preventing or reducing cellular proliferation comprising contacting the cell or RNA from the cell with a pharmaceutical composition as defined herein, whereby cellular proliferation is prevented or reduced. The prevention or reduction of proliferation may be in vitro or in vivo. The prevention may be done on a cellular assay or within a tissue sample or within the living mammal.

EXPERIMENTALS

A currently preferred example of the LNA oligonucleotides defined herein is the LNA oligonucleotide SEQ ID NO. 2. The following examples illustrate the surprisingly good properties of this LNA oligonucleotide, but it is believed that other LNA oligonucleotides comprising (or having) the sequence SEQ ID NO. 1 or SEQ ID NO. 28 have similarly interesting properties.

Example 1

Monomer Synthesis

The LNA monomer building blocks and derivatives thereof were prepared following published procedures and references cited therein, see:

WO 03/095467 A1

D. S. Pedersen, C. Rosenbohm, T. Koch (2002) Preparation of LNA Phosphoramidites, Synthesis 6, 802-808.

M. D. Sørensen, L. Kværnø, T. Bryld, A. E. Håkansson, B. Verbeure, G. Gaubert, P. Herdewijn, J. Wengel (2002) α-L-ribo-configured Locked Nucleic Acid (α-l-LNA): Synthesis and Properties, J. Am. Chem. Soc., 124, 2164-2176.

S. K. Singh, R. Kumar, J. Wengel (1998) Synthesis of Novel Bicyclo[2.2.1] Ribonucleosides: 2'-Amino- and 2'-Thio-LNA Monomeric Nucleosides, J. Org. Chem. 1998, 63, 6078-6079.

C. Rosenbohm, S. M. Christensen, M. D. Sørensen, D. S. Pedersen, L. E. Larsen, J. Wengel, T. Koch (2003) Synthesis of 2'-amino-LNA: a new strategy, Org. Biomol. Chem. 1, 655-663. D. S. Pedersen, T. Koch (2003) Analogues of LNA (Locked Nucleic Acid). Synthesis of the 2'-Thio-LNA Thymine and 5-Methyl Cytosine Phosphoramidites, Synthesis 4, 578-582.

Example 2

Oligonucleotide Synthesis

Oligonucleotides were synthesized using the phosphoramidite approach on an Expedite 8900/MOSS synthesizer (Multiple Oligonucleotide Synthesis System) at 1 µmol or 15 µmol scale. For larger scale synthesis an Äkta Oligo Pilot was used. At the end of the synthesis (DMT-on), the oligonucleotides were cleaved from the solid support using aqueous ammonia for 1-2 hours at room temperature, and further deprotected for 4 hours at 65° C. The oligonucleotides were purified by reverse phase HPLC (RP-HPLC). After the removal of the DMT-group, the oligonucleotides were characterized by AE-HPLC, RP-HPLC, and CGE and the molecular mass was further confirmed by ESI-MS. See below for more details.

Preparation of the LNA-Solid Support:
Preparation of the LNA Succinyl Hemiester

5'-O-DMT-3'-hydroxy-LNA monomer (500 mg), succinic anhydride (1.2 eq.) and DMAP (1.2 eq.) were dissolved in DCM (35 mL). The reaction was stirred at room temperature overnight. After extractions with $NaH_2PO_4$ 0.1 M pH 5.5 (2×) and brine (1×), the organic layer was further dried with anhydrous $Na_2SO_4$ filtered and evaporated. The hemiester derivative was obtained in 95% yield and was used without any further purification.

Preparation of the LNA-Support

The above prepared hemiester derivative (90 µmol) was dissolved in a minimum amount of DMF, DIEA and pyBOP (90 µmol) were added and mixed together for 1 min. This pre-activated mixture was combined with LCAA-CPG (500 Å, 80-120 mesh size, 300 mg) in a manual synthesizer and stirred. After 1.5 hours at room temperature, the support was filtered off and washed with DMF, DCM and MeOH. After drying, the loading was determined to be 57 µmol/g (see Tom Brown, Dorcas J. S. Brown. Modern machine-aided methods of oligodeoxyribonucleotide synthesis. In: F. Eckstein, editor. Oligonucleotides and Analogues A Practical Approach. Oxford: IRL Press, 1991: 13-14).

Elongation of the Oligonucleotide

The coupling of phosphoramidites (A(bz), G(ibu), 5-methyl-C(bz)) or T-β-cyanoethyl-phosphoramidite) is performed by using a solution of 0.1 M of the 5'-O-DMT-protected amidite in acetonitrile and DCI (4,5-dicyanoimidazole) in acetonitrile (0.25 M) as activator. The thiolation is carried out by using xanthane chloride (0.01 M in acetonitrile:pyridine 10%). The rest of the reagents are the ones typically used for oligonucleotide synthesis. The protocol provided by the supplier was conveniently optimised. Purification by RP-HPLC:

| | |
|---|---|
| Column: | Xterra $RP_{18}$ |
| Flow rate: | 3 mL/min |
| Buffers: | 0.1 M ammonium acetate pH 8 and acetonitrile |

| Abbreviations | |
|---|---|
| DMT: | Dimethoxytrityl |
| DCI: | 4,5-Dicyanoimidazole |

| Abbreviations | |
|---|---|
| DMAP: | 4-Dimethylaminopyridine |
| DCM: | Dichloromethane |
| DMF: | Dimethylformamide |
| THF: | Tetrahydrofurane |
| DIEA: | N,N-diisopropylethylamine |
| PyBOP: | Benzotriazole-1-yl-oxy-tris-pyrrolidino-phosphonium hexafluorophosphate |
| Bz: | Benzoyl |
| Ibu: | Isobutyryl |

Example 3

Design of the LNA Oligonucleotide

TABLE 2

LNA Oligonucleotides

| SEQ ID NO. | Sequence and design | designs |
|---|---|---|
| 1 | 5'-$^{Me}C_xT_x^{Me}C_xA_sa_sc_sc_sa_st_sg_sg_s^{Me}C_sA_sG_xc$-3' | |
| 2 | 5'-$^{Me}C_sT_s^{Me}C_sA_sa_st_sc_sc_sa_st_sg_sg_s^{Me}C_sA_sG_sc$-3' | 4-8-3-1 |
| Reducing the amount of phosphorothioate links | | |
| 3 | 5'-$^{Me}CT^{Me}CA_sa_st_sc_sc_sa_st_sg_sg_s^{Me}CAG_sc$-3' | 4-8-3-1 |
| 4 | 5'-$^{Me}CT^{Me}CA_sa_st_sc_sc_sa_st_sg_sg_s^{Me}CAGc$-3' | 4-8-3-1 |
| Reducing the amount of LNA monomers units | | |
| 5 | 5'-$^{Me}C_sT_s^{Me}C_sA_sa_st_sc_sc_sa_st_sg_sg_s^{Me}C_sA_sg_sc$-3' | 4-8-2-2 |
| 6 | 5'-$c_sT_s^{Me}C_sA_sa_st_sc_sc_sa_st_sg_sg_s^{Me}C_sA_sG_sc$-3' | 1-3-8-3-1 |
| Reducing the amount of phosphorothioate links and LNA monomers units | | |
| 7 | 5'-$^{Me}CT^{Me}CA_sa_st_sc_sc_sa_st_sg_sg_s^{Me}CAg_sc$-3' | 4-8-2-2 |
| 8 | 5'-$c_sT^{Me}CA_sa_st_sc_sc_sa_st_sg_sg_s^{Me}CAG_sc$-3' | 1-3-8-3-1 |
| 9 | 5'-$^{Me}CT^{Me}CA_sa_st_sc_sc_sa_st_sg_sg_s^{Me}CAgc$-3' | 4-8-2-2 |
| 10 | 5'-$cT^{Me}CA_sa_st_sc_sc_sa_st_sg_sg_s^{Me}CAGc$-3' | 1-3-8-3-1 |
| LNA oligonucleotides containing α-L-LNA monomer units | | |
| 11 | 5'-$^{Me}C^\alpha_sT^\alpha_s{}^{Me}C^\alpha_sA^\alpha_sa_st_sc_sc_sa_st_sg_sg_s^{Me}C^\alpha_sA^\alpha_sG^\alpha_sc$-3' | 4-8-3-1 |
| 12 | 5'-$^{Me}C_sT_s^{Me}C_sA^\alpha_sa_st_sc_sc_sa_st_sg_sg_s^{Me}C^\alpha_sA_sG_sc$-3' | 4-8-3-1 |
| 13 | 5'-$^{Me}C^\alpha T^\alpha{}^{Me}C^\alpha A^\alpha_sa_st_sc_sc_sa_st_sg_sg_s^{Me}C^\alpha A^\alpha G^\alpha_sc$-3' | 4-8-3-1 |
| 14 | 5'-$^{Me}C^\alpha T^\alpha{}^{Me}C^\alpha A^\alpha_sa_st_sc_sc_sa_st_sg_sg_s^{Me}C^\alpha A^\alpha G^\alpha c$-3' | 4-8-3-1 |
| 15 | 5'-$^{Me}C^\alpha_sT^\alpha_s{}^{Me}C^\alpha_sA^\alpha_sa_st_sc_sc_sa_st_sg_sg_s^{Me}C^\alpha_sA^\alpha_sg_sc$-3' | 4-8-2-2 |
| 16 | 5'-$c_sT^\alpha_s{}^{Me}C^\alpha_sA^\alpha_sa_st_sc_sc_sa_st_sg_sg_s^{Me}C^\alpha_sA^\alpha_sG^\alpha_sc$-3' | 1-3-8-3-1 |
| 17 | 5'-$^{Me}C^\alpha T^\alpha{}^{Me}C^\alpha A^\alpha_sa_st_sc_sc_sa_st_sg_sg_s^{Me}C^\alpha A^\alpha g_sc$-3' | 4-8-2-2 |
| 18 | 5'-$c_sT^\alpha{}^{Me}C^\alpha A^\alpha_sa_st_sc_sc_sa_st_sg_sg_s^{Me}C^\alpha A^\alpha G^\alpha_sc$-3' | 1-3-8-3-1 |
| 19 | 5'-$^{Me}C^\alpha T^\alpha{}^{Me}C^\alpha A^\alpha_sa_st_sc_sc_sa_st_sg_sg_s^{Me}C^\alpha A^\alpha gc$-3' | 4-8-2-2 |
| 20 | 5'-$cT^\alpha{}^{Me}C^\alpha A^\alpha_sa_st_sc_sc_sa_st_sg_sg_s^{Me}C^\alpha A^\alpha G^\alpha c$-3' | 1-3-8-3-1 |
| References oligonucleotides | | |
| 21 | $T_sG_sT_sG_sc_st_sa_st_st_sc_st_sg_st_sg_sA_sA_sT_sT$ | 4-10-4 |
| 22 | 5'-$G_s^{Me}C_sA_s^{Me}C_sa_sg_st_st_sg_sa_sa_sa_s^{Me}C_sA_sT_sc$-3' | 4-8-3-1 |
| 23 | 5'-$G_s^{Me}C_sA_sG_st_sg_sg_sa_st_sg_sa_sa_sG_s^{Me}C_s^{Me}C_sA$-3' | 4-8-4 |

TABLE 2-continued

LNA Oligonucleotides

| SEQ ID NO. | Sequence and design | designs |
|---|---|---|
| 24 | $^{Me}C_sG_s{}^{Me}C_sA_sg_sa_st_st_sa_sg_sa_sa_sA_s{}^{Me}C_s{}^{Me}C_st$ | 4-8-3-1 |
| 25 | $t_sg_st_sg_sc_st_sa_st_st_sc_st_sg_st_sg_sa_sa_st_st$ | |
| 26 | $^{Me}C_sT_sc_sc_sc_sa_sg_sc_sg_st_sg_sc_sg_s{}^{Me}C_s{}^{Me}C_sa$ | |
| 27 | $A_s{}^{Me}C_sc_sg_sc_sg_st_sg_sc_sg_sa_sc_sc_s{}^{Me}C_sT_sc$ | |
| 28 | 5'-$(^{Me}\underline{C}_x)(T_x)^{Me}C_xA\underline{A}_ts_sc_sa_st_sg_sg_s{}^{Me}C_xA_x(\underline{G}_x)(c)$-3' | |

In Table 2, capital letters (without superscript) designate a β-D-oxy-LNA nucleotide analogue (β-D-oxy-LNA); superscript "α" after a capital letter (e.g. $G^\alpha$), however, denote that the LNA nucleotide analogue is an α-L-LNA nucleotide analogue (α-L-oxy-LNA), small letters designate a deoxynucleotide, subscript "s" designates a phosphorothioate link between neighbouring nucleotides/LNA nucleotide analogues, and no subscript between neighbouring nucleotides/LNA nucleotide analogues designates a phosphorodiester link. All LNA-C monomers are 5-methyl-C ($^{Me}C$). The compounds were designed to target different regions of the human Survivin RNA, using the published sequences (Genbank accession number NM_001168).

Example 4

Measurement of $T_m$

Measurement of melting temperature ($T_m$) of the compounds: A 3 μM solution of SEQ ID NO. 2 in 10 mM sodium phosphate/100 mM NaCl/0.1 nM EDTA, pH 7.0 was mixed with its complement DNA/RNA 3 μM in 10 mM sodium phosphate/100 mM NaCl/0.1 nM EDTA, pH 7.0 at 90° C. for a minute and allowed to cool to room temperature. The $T_m$ of the duplex was then determined by increasing the temperature 1° C./min. from 25 to 95° C. The $T_m$ of SEQ ID NO. 2 is shown in the Table 7 in example 21:

Example 5

Stability of SEQ 10 NO. 2 in Human and Mouse Plasma

Stability of 20 μM SEQ ID NO. 2 and SEQ ID NO. 24 in human and mouse plasma (Li-Heparine (Taconic, M&B)) at 37° C. at different time aliquots: 0, 1, 2, 4, 24, 48 and 96 hours. A commercially available ladder was also included (10 and 20 mer are visible on the PAGE). (see FIG. 1)

Example 6

In Vitro Model: Cell Culture

The effect of antisense compounds on target nucleic acid expression can be tested in any of a variety of cell types provided that the target nucleic acid is present at measurable levels. Target can be expressed endogenously or by transient or stable transfection of a nucleic acid encoding said nucleic acid.

The expression level of target nucleic acid can be routinely determined using, for example, Northern blot analysis, Quantitative PCR, Ribonuclease protection assays. The following cell types are provided for illustrative purposes, but other cell types can be routinely used, provided that the target is expressed in the cell type chosen.

Cells were cultured in the appropriate medium as described below and maintained at 37° C. at 95-98% humidity and 5% $CO_2$. Cells were routinely passaged 2-3 times weekly.

15PC3: The human prostate cancer cell line 15PC3 was kindly donated by Dr. F. Baas, Neurozintuigen Laboratory, AMC, The Netherlands and was cultured in DMEM (Sigma)+10% fetal bovine serum (FBS)+Glutamax I+gentamicin.

PC3: The human prostate cancer cell line PC3 was purchased from ATCC and was cultured in F12 Coon's with glutamine (Gibco)+10% FBS+gentamicin.

518A2: The human melanoma cancer cell line 518A2 was kindly donated by Dr. B. Jansen, Section of experimental Oncology, Molecular Pharmacology, Department of Clinical Pharmacology, University of Vienna and was cultured in DMEM (Sigma)+10% fetal bovine serum (FBS)+Glutamax I+gentamicin.

Example 7

In Vitro Model: Treatment with Antisense Oligonucleotide

Cell culturing and transfections: 15PC3 cells were seeded in 12-well plates and grown for two days at 37° C. (5% $CO_2$) in DMEM supplemented with 10% FBS, Glutamax I and Gentamicin. When the cells were 60-70% confluent, they were transfected in duplicates with different concentrations of oligonucleotides (0.2-25 nM) using Lipofectamine 2000 (10 μg/ml). Transfections were carried out essentially as described by Dean et al. (1994, JBC 269:16416-16424). In short, cells were incubated for 10 min. with Lipofectamine in OptiMEM followed by addition of oligonucleotide to a total volume of 0.5 ml transfection mix per well. After 4 hours, the transfection mix was removed, cells were washed and grown at 37° C. for approximately 20 hours (mRNA analysis) or 12-72 hours (protein analysis) in the appropriate growth medium. Cells were then harvested for protein and RNA analysis.

Example 8

In vitro model: Extraction of RNA and cDNA Synthesis

Total RNA Isolation

Total RNA was isolated using RNeasy mini kit (Qiagen). Cells were washed with PBS, and Cell Lysis Buffer (RTL, Qiagen) supplemented with 1% mercaptoethanol was added directly to the wells. After a few minutes, the samples were processed according to manufacturer's instructions.

First Strand Synthesis

First strand synthesis was performed using OmniScript Reverse Transcriptase kit according to the manufacturer's instructions (Qiagen). For each sample, 0.5 µg total RNA was adjusted to 12 µl and mixed with 0.2 µl poly $(dT)_{12-18}$ (0.5 µg/µl) (Life Technologies), 2 µl dNTP mix (5 mM each), 2 µl 10× RT buffer, 0.5 µl RNAguard™ RNase Inhibitor (33 units/ml, Amersham) and 1 µl OmniScript Reverse Transcriptase followed by incubation at 37° C. for 60 min. and heat inactivation at 93° C. for 5 min.

Example 9

In Vitro Model: Analysis of Oligonucleotide Inhibition of Survivin, Bcl-2 or Survivin Splice Variant Expression by Real-Time PCR To determine the relative Survivin mRNA level in oligonucleotide treated and untreated cells, the generated cDNA was used in quantitative PCR analysis using an iCycler from BioRad. The cDNA was diluted 5-fold and 8 µl was mixed with 52 µl Taqman probe master mix containing 30 µl Platinum Quantitative PCR SuperMix UDG 2×PCR master mix (Invitrogen), 3 µl 20× Taqman probe and primer mix (forward primer: 5'AAGGACCACCGCATCTCTACA (SEQ ID NO:29), final 0.9 µM. Reverse primer: 5'CCAAGTCTGGCTCTTTCTCAGT (SEQ ID NO:30), final 0.6 µM and taqman probe: FAM-CGAGGCTGGCTTCATCCACTGCC-TAMRA (SEQ ID NO:31), final 0.1 µM) and 19 µl H$_2$O. The 60 µl were dispersed in two wells (96 well plates) with 25 µl in each well. For human Bcl-2 the PCR primers were: forward primer: 5' CATGTGTGTGGAGAGCGTCAA 3' (final concentration in the assay; 0.6 µM) (SEQ ID NO: 32) reverse primer: 5' GCCGGTTCAGGTACTCAGRCA 3' (final concentration in the assay; 0.6 µM) (SEQ ID NO: 33) and the PCR probe was: 5' FAM-CCTGGTGGACAACATCGC-CCTGT-TAMRA 3' (final concentration in the assay; 0.1 µM) (SEQ ID NO: 34). For Survivin splice variant PCR the following primers and concentrations were used. Splice variant 1 (Full) Forward primer 5'-GGCCGAGGCTGGCTTCAT-3' (SEQ ID NO:35) (Final concentration in the assay 0.6 µM) Reverse primer 5'-TGCTTTTTATGTTCCTCTATGGG-3' (SEQ ID NO:36) (Final concentration in the assay 0.6 µM). Splice variant 2 (2B) Forward primer 5'-GGCCGAGGCTGGCTTCAT-3' (SEQ ID NO:35) (Final concentration in the assay 0.3 µM) Reverse primer 5'-AAGTGCTGGTATTACAGGCGT-3' (SEQ ID NO:37) (Final concentration in the assay 0.3 µM). Splice variant 3 (ΔEx3) Forward primer 5'-GGCCGAGGCTGGCTTCAT-3' (SEQ ID NO:35) (Final concentration in the assay 0.3 µM) Reverse primer 5'-ATTGTTGGTTTCCTTTGCATG-3' (SEQ ID NO:38) (Final concentration in the assay 0.3 µM). taqman Probe 5'-FAM-CACTGCCCCACTGAGAACGAGCCAGACT-TAMRA-3' (SEQ ID NO:39) (Final concentration in the assay 0.1 µM).

The primers and probe were obtained from Proligonucleotide (France). To normalize any variance in sample preparation, the endogenous GAPDH mRNA was quantified using a pre-developed Taqman assay reagent from Applied Biosystems (4310884E) according to manufacturer's Instructions. Two-fold dilutions of cDNA, synthesised from untreated 15PC3 cells (expressing both Survivin and GAPDH), was used to prepare standard curves for the assays. The PCR program was as follows: 50° C. for 2 min., 95° C. for 10 min. followed by 40 cycles of 95° C. 15 sec., 60° C. 1 min. Relative quantities of Survivin mRNA were determined from the calculated threshold cycle using the iCycler IQ Real Time Detection System software. See FIGS. 6B, 6C, 9 and 2C.

Example 10

In Vitro Analysis: Western Blot Analysis of Survivin Protein Levels

Western Blotting:

The in vitro effect of Survivin oligoes on Survivin protein levels in transfected cells was determined by Western Blotting.

Figure 2A:
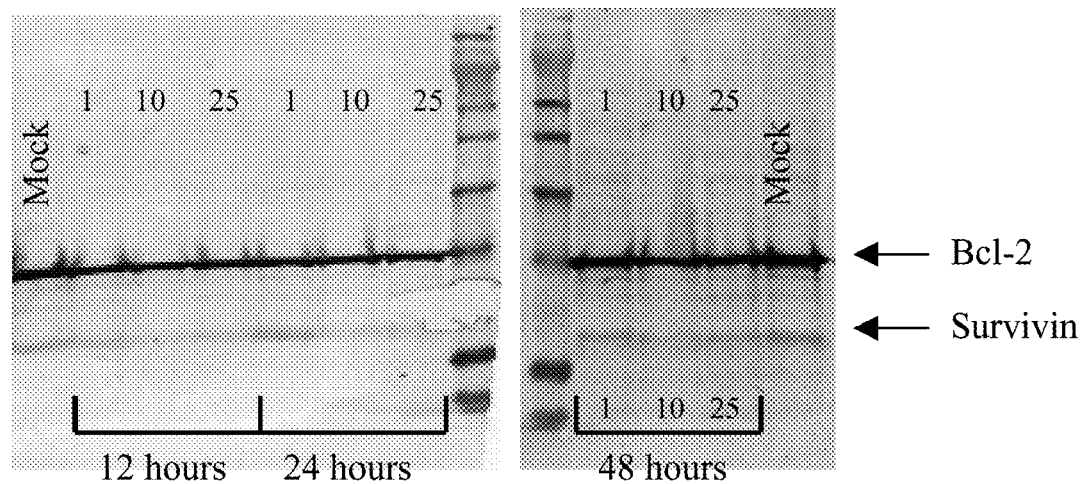
FIG. 2A shows Survivin protein down-regulation in SEQ ID NO. 2 transfected 15PC3 prostate cancer cells. 15PC3 cells were transfected with 1, 10, and 25 nM SEQ ID NO. 2 and analysed at timepoints 12, 24 and 48 hours for Survivin protein down-regulation by Western blotting. SEQ ID NO. 2 or mock transfected cells were harvested and compared for Survivin protein expression. Bcl-2 protein was co-monitored.

Cells were harvested and lysed in 50 mM Tris-HCl pH 6.8, 10% glycerol, 2.5% SDS, 5 mM DTT and 6 M urea supplemented with protease inhibitor cocktail (Roche). Total protein concentrations were measured using a BCA protein assay kit (Pierce). 50 µg total protein was run on a 12% Bis-Tris gels in MOPS buffer and blotted onto a PVDF membranes according to manufacture's instructions (Invitrogen). After overnight incubation in blocking buffer (PBS-T supplemented with 5% low fat milk powder), the membranes were incubated overnight with 1:500 dilution of polyclonal anti-Survivin antibody Novus 500-201 followed by one hour incubation with 1:1000 dilution of anti-Bcl (DAKO). Membranes were then incubated with secondary antibodies (either 1:1000 diluted HRP conjugated secondary antibodies from DAKO or AP conjugated antibodies from Invitrogen) and Survivin and Bcl2 were visualized using a chromogenic immunodetection kit (Invitrogen) or a chemiluminescens ECL$^+$ detection kit (Amersham). See FIG. 2A.

Example 11

In Vitro Analysis: ELISA Analysis of Survivin Protein Levels

Figure 2B:
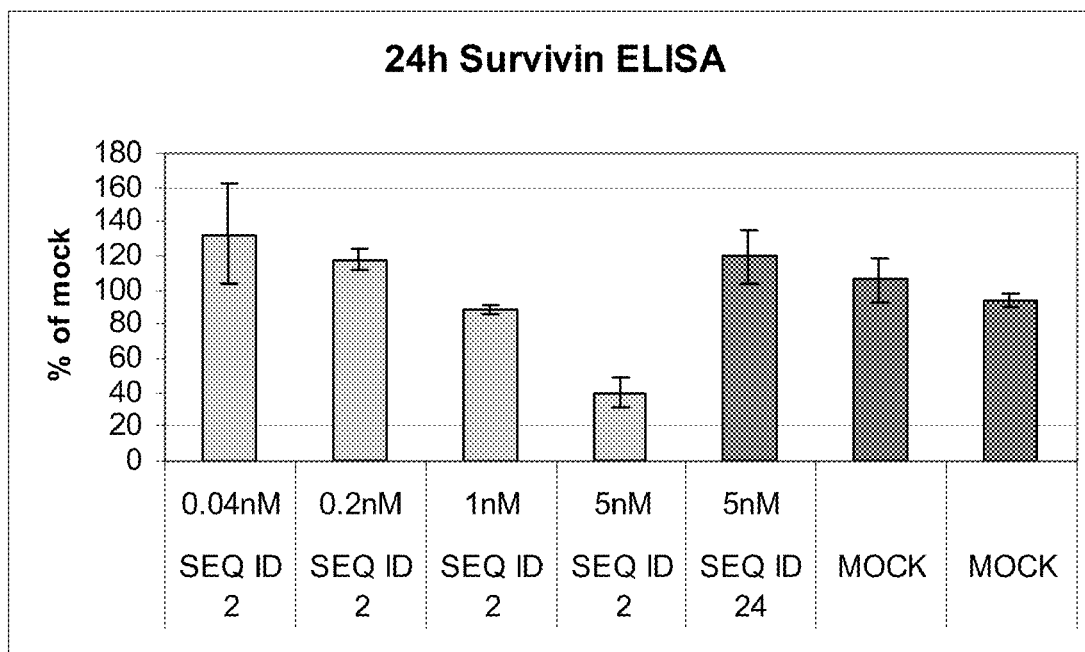
FIG. 2B shows quantification of Survivin protein using ELISA after treatment of 15 PC3 cells with SEQ ID NO. 2 compared to the negative control SEQ ID NO. 24 and mock treated for 24 hours. 15PC3 cells were transfected with SEQ ID NO. 2 at four concentrations ranging from 0.04-5 nM or the negative control SEQ ID NO. 24 at 5 nM.
Figure 2C:
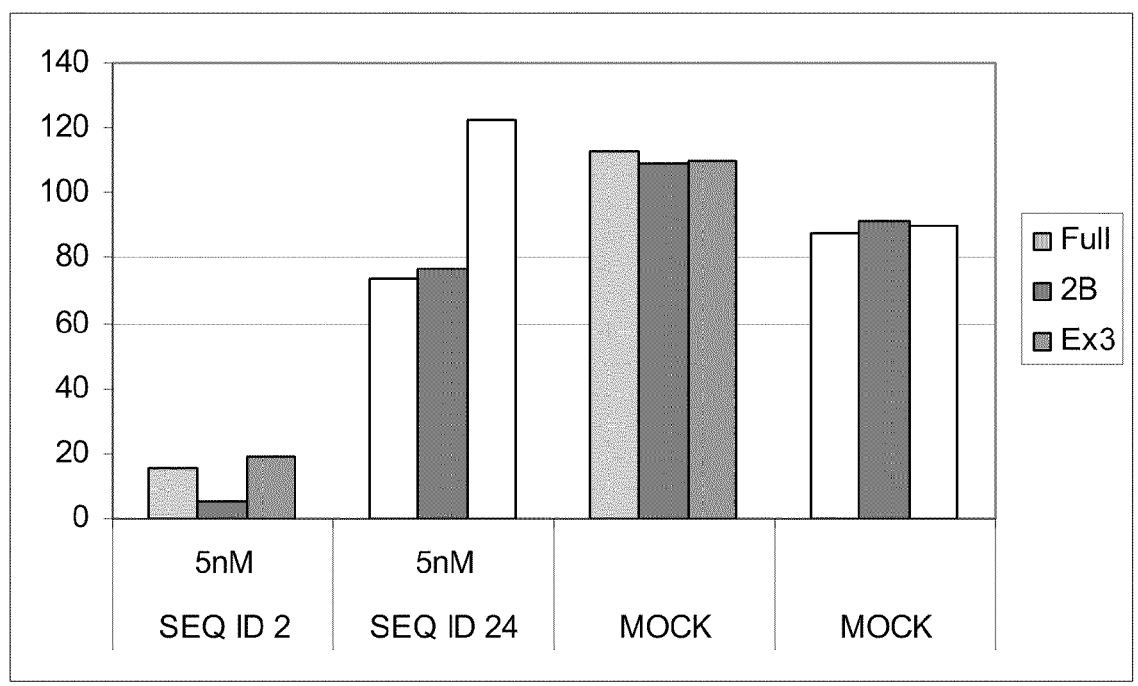
FIG. 2C shows the expression of the 3 different isoforms of Survivin mRNA (Survivin full length, Survivin2B and SurvivinΔex3) in 15PC3 cells after treatment with 5 nM SEQ ID NO. 2, compared to 5 nM SEQ ID NO. 24 or mock. Expression is normalised to the expression of GAPDH and related to average of the expression in the mock treated cells. It is evident that SEQ ID NO. 2 is able to down-regulate all expressed isoforms of human Survivin, whereas the negative control SEQ ID NO. 24 is not.

Harvested cells were lysed and Survivin was assayed using R&D Systems Human Survivin DuoSet IC ELISA (Catalog #DYC647), according to the recommendation of the manufacture. See FIG. 2B.

Example 12

In Vitro Analysis: Antisense Inhibition of Human Survivin Expression Using Antisense Oligonucleotides In accordance with the present invention, a series of oligonucleotides were designed to target different regions of the human Survivin RNA, using published sequences (GenBank accession number NM_001168). See Table 2—LNA oligonucleotides.

LNA oligonucleotides were evaluated for their potential to knockdown Survivin mRNA in 15PC3 cells. The data are presented as percentage down-regulation relative to mock transfected cells. Transcript steady state was monitored by Real-time PCR and normalised to the GAPDH transcript steady state, see Table 3. Note that all LNA C are 5-methyl-Cytosine.

TABLE 3

| Oligo 4-8-3-1 design | Oligo 4-8-4 design | IC$_{50}$ [nM] | IC$_{75}$ [nM] |
|---|---|---|---|
| | SEQ ID NO. 23 | 2.5 (0.5) | 6.2 (1.6) |
| SEQ ID NO. 2 | | 2.9 (0.4) | 4.8 (0.3) |

Experiments were carried out at least three times. Numbers in brackets are standard deviations.

Example 13

Apoptosis Induction and Proliferation Inhibition by Antisense LNA Oligonucleotides Culturing of cells: 15PC3 was cultured in DMEM (Sigma) containing 10% fetal bovine serum, Glutamax I and gentamicin at 37° C., 95% humidity and 5% CO2. The cervical carcinoma cell line HeLa were cultured in MEM (Sigma) containing 10% fetal bovine serum, Glutamax I and gentamicin at 37° C., 95% humidity and 5% CO2. When reaching 60-70% confluency, the cells were transfected using Lipofectamine 2000 (5 µg/ml).

Measurement of Active Caspase 3/7 Activity

15PC3 cells were seeded to a density of 10000 cells per well in white 96-well plates (Nunc 136101) in DMEM the day prior to transfection. The next day cells were washed once in prewarmed OptiMEM followed by addition of 72 µl OptiMEM containing 5 µg/ml Lipofectamine-2000 (In vitrogen). Cells were incubated for 7 min before adding 18 µl oligonucleotides diluted in OptiMEM. The final oligonucleotide concentration ranged from 0.2 nM to 100 nM. After 4 hours of treatment, cells were washed in OptiMEM and 100 µl DMEM containing serum was added. Following oligonucleotide treatment, cells were allowed to recover for the period indicated before they were removed from the $CO_2$ incubator and equilibrated to room temperature for 15 min. 100 µl of the highly sensitive Caspase 3/7-Glo™ Reagent (Promega) was added directly to the cells, and the plates were incubated for 20 min. Luminescence (luciferase activity) was recorded in a Luminoskan Ascent instrument (Thermo Labsystems). The luciferase activity is measured as Relative Light Units per seconds (RLU/s). The data was analysed using the Ascent software 2.4.2. Graphs of fold induction relative to mock were generated using MS Excel.

Figure 3:
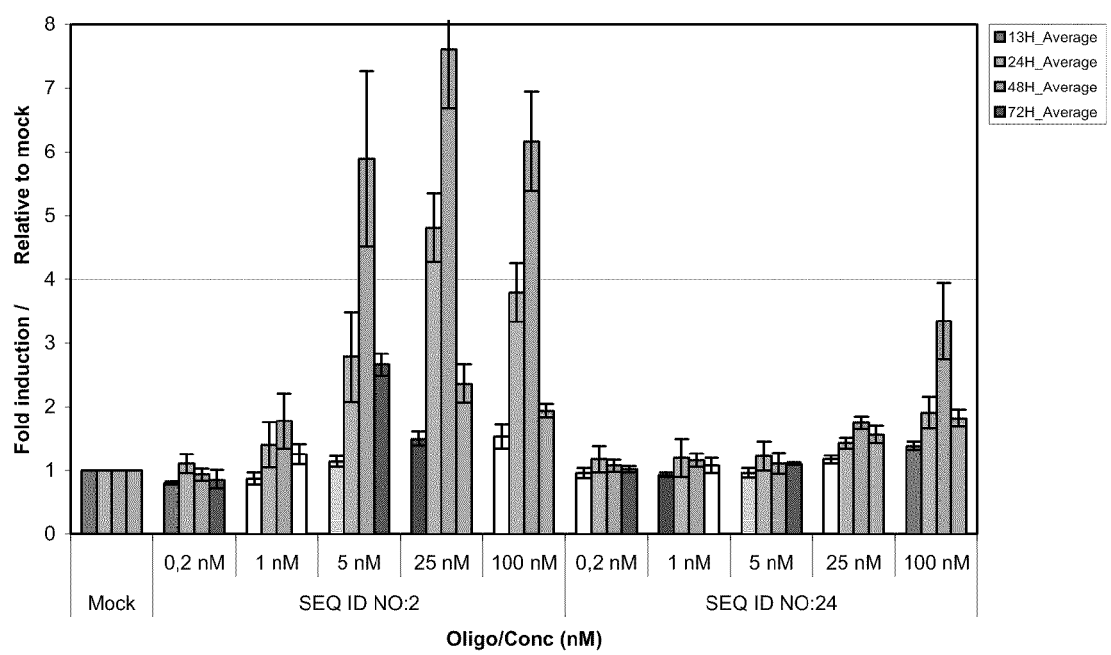
FIG. 3 shows Apoptosis measured as induced Caspase 3/7 activity following 13-72 hours treatment with SEQ ID NO. 2 in 15PC3 cells. 15PC3 cells were transfected with SEQ ID NO. 2 or the negative control, SEQ ID NO. 24, at five concentrations ranging from 0.2-100 nM. Fold induction is presented relative to mock as mean value from three independent experiments. The standard deviation is presented on each bar.
Figure 6A:
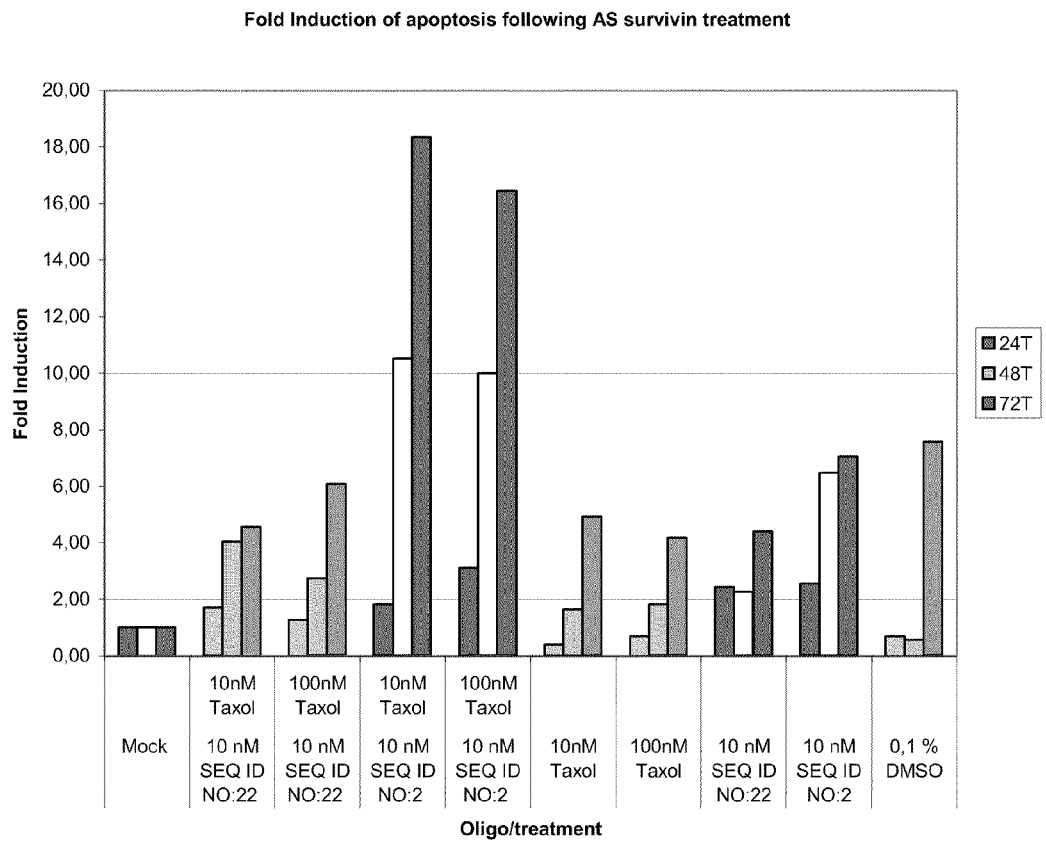
FIG. 6A shows Apoptosis measured as induced Caspase 3/7 activity following 24-72 hours treatment with SEQ ID NO. 22, SEQ ID NO. 2 or Taxol in 15PC3 prostate cancer cells. Cells were treated with either SEQ ID NO. 22 or SEQ ID NO. 2 at 10 nM in combination with Taxol (10 nM or 100 nM), 0.1% DMSO was used as vehicle. Fold induction is presented relative to mock as mean value. The combination of SEQ ID NO. 2 with Taxol shows a clear additive effect on the induction of apoptosis after both 48 hours and 72 hours.
Figure 6B:
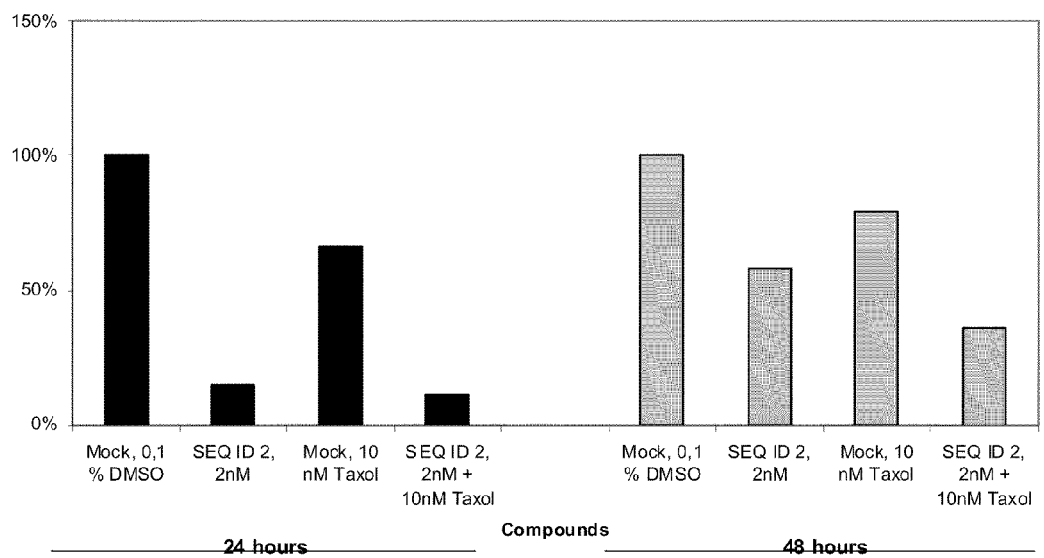
FIG. 6B shows Survivin mRNA expression in 15PC3 cells after 24 hours and 48 hours of treatment with 2 nM SEQ ID NO. 2 or 2 nM SEQ ID NO. 2 combined with 10 nM Taxol. Expression is analysed by qPCR, normalised to the expression of GAPDH and related to the expression level in Mock (0.1% DMSO) treated cells. Survivin mRNA is found to be down-regulated in both treatment schedules and at both time-points
Figure 6C:
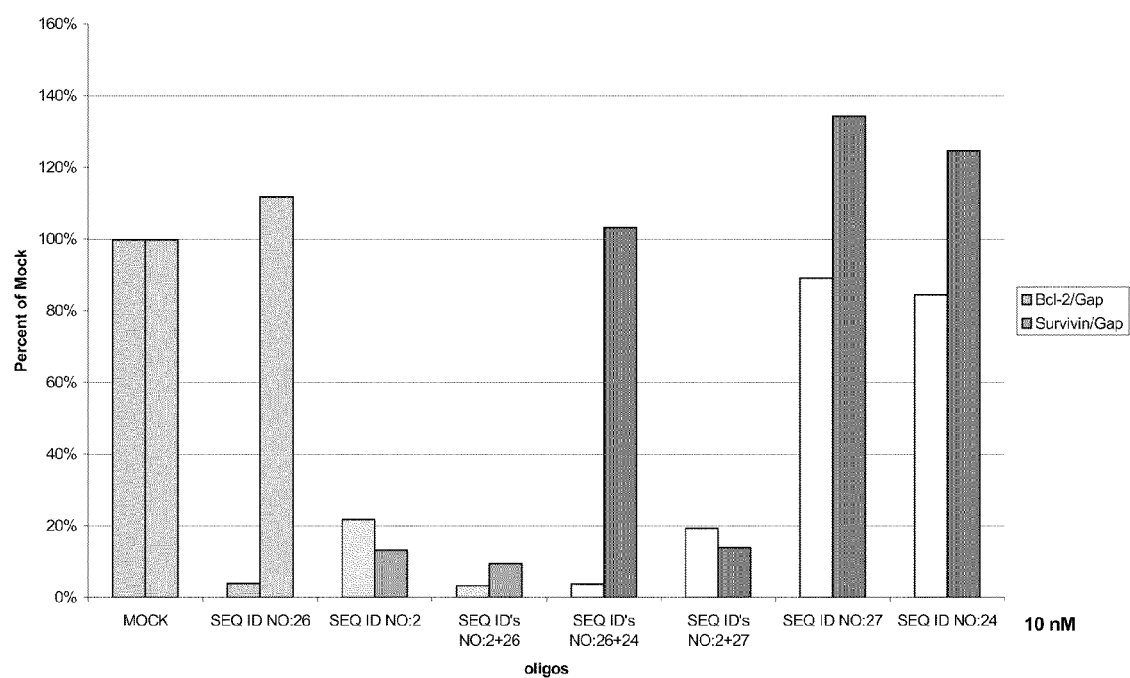
FIG. 6C shows Survivin mRNA and Bcl-2 mRNA expression in 15 PC3 cells after 24 hours of treatment with 10 nM SEQ ID NO. 26 (Bcl-2 specific), 10 nM SEQ ID NO. 2, 10 nM control SEQ ID NO. 24, 10 nM SEQ ID NO. 27 (Negative control to SEQ ID NO. 26) or combinations of 10 nM of each the oligonucleotides. All expression is analysed by qPCR, normalised to the expression GAPDH and related to the expression level in mock treated cells. SEQ ID NO. 26 is Bcl-2 specific and does not have any effect on Survivin, neither as single agent nor in combination with control compounds (SEQ ID NO. 24 or SEQ ID NO. 27). SEQ ID NO. 2 is a strong apoptosis inducer and have effects on Survivin and Bcl-2 expression, either as single agent or in combination with control compounds (SEQ ID NO. 24 or SEQ ID NO. 27).

Caspase 3/7 specificity of the apoptotic response was demonstrated by incubating transfected cells with a caspase 3/7 inhibitor. Staurosporine, Camptothecine or Taxol induced cells served as positive controls (see FIGS. 3, 6A and Table 4 plus Example 21).

TABLE 4

Caspase 3/7 measurement of transfetced cells 24 hours after transfection of 15PC3 cells

| Caspase 3/7 assay | Oligonucleotide | Fold induction of apoptosis |
| --- | --- | --- |
| Fold Induction (24 hours, 5 nM) | SEQ ID NO. 2 | 3.5 x |
| | SEQ ID NO. 24 | 1.5 x |
| Maximum Induction Fold-induction (conc., time) | SEQ ID NO. 2 | 6.9 x (25 nM, 48 hours) |
| | SEQ ID NO. 24 | 3.1 x (100 nM, 48 hours) |

Figure 4:
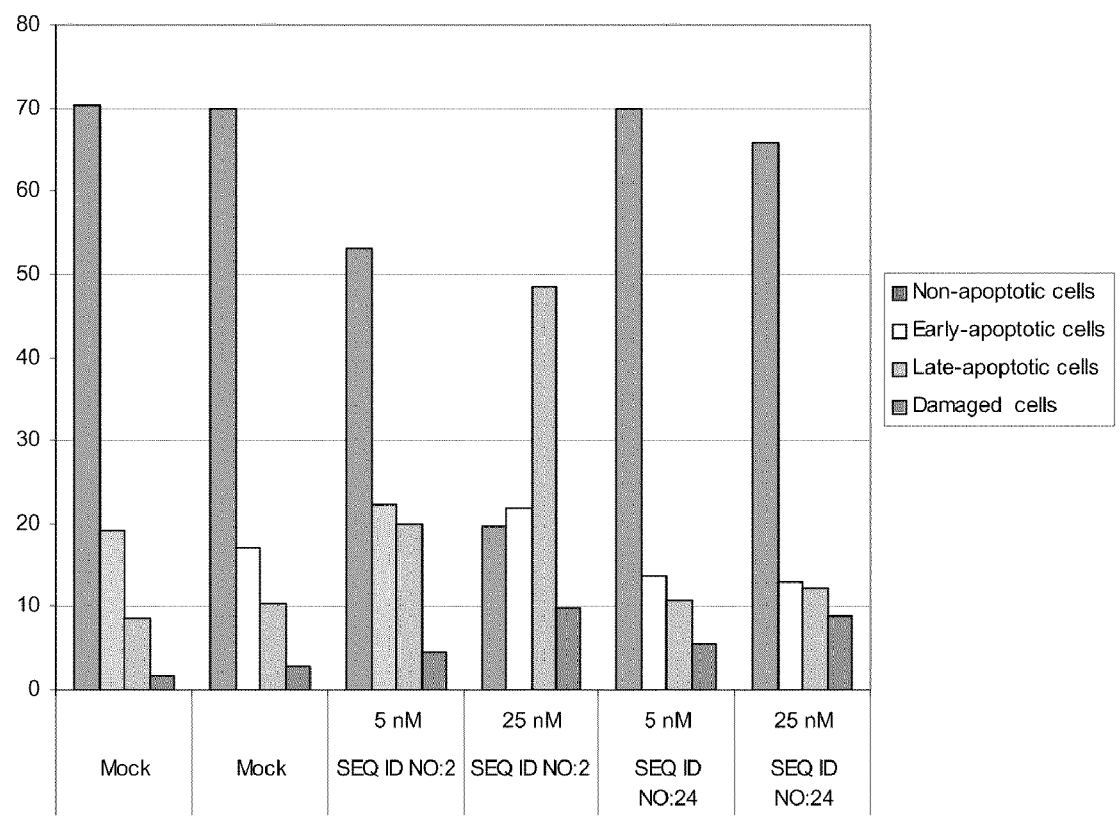
FIG. 4 shows treatment of HeLa cells with 5 nM or 25 nM SEQ ID NO. 2 leads to dose dependent induction of early and late apoptosis measured by Annexin V-FITC/PI staining analysed by flow cytometry. At the same concentrations the negative control oligonucleotide SEQ ID NO. 24 do not induce apoptosis.

Annexin V-FITC Flow Cytometry Analysis $0.4 \times 10^6$ HeLa cells were seeded in T25 flasks one day prior to transfection. On the day of transfection, the cells were washed once in 37° C. OptiMEM followed by addition of 2.8 ml OptiMEM containing 5 µg/ml Lipofectamine-2000 (In vitrogen). Cells were incubated for 7 min before adding 700 µl oligonucleotides diluted in OptiMEM to a final concentration of 5 nM or 25 nM, Mock transfetced cells served as control. After 4 hours of treatment cells were washed in OptiMEM and 3 ml culture medium was added. Following oligonucleotide treatment cells were allowed to recover for 48 hours before they were harvested by scraping and washed twice in PBS. $0.2 \times 10^6$ cells were incubated with 5 µl Annexin V-FITC and 10 µl propidium iodide (PI-10 mg/ml) and incubated for 15 min at room temperature in the dark. Incubation of transfected cells with purified recombinant Annexin V prior to adding Annexin V-FITC were used to demonstrate specificity and selectivity of the staining. Moreover, TRAIL (Apo2L) induced HeLA cells (0.5 µg/ml) were used as positive control. (See FIG. 4)

Measurement of Proliferating Viable Cells Using the MTS Assay

Cells were seeded to a density of 10000 cells per well in clear 96 well plate (Scientific Orange no. 1472030100) in DMEM the day prior to transfection. The next day cells were washed once in prewarmed OptiMEM followed by addition of 72 µl OptiMEM containing 5 µg/ml Lipofectamine 2000 (Invitrogen). Cells were incubated for 7 min before adding 18 µl oligonucleotides diluted in OptiMEM. The final oligonucleotide concentration ranged from 5 nM to 100 nM. After 4 hours of treatment, cells were washed in OptiMEM and 100 µl serum containing DMEM was added. Following oligonucleotide treatment cells were allowed to recover for the period indicated, viable cells were measured by adding 20 µl of the tetrazolium compound [3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate, PES; CellTiter 96® AQueous One Solution Cell Proliferation Assay, Promega). Viable cells were measured at 490 nm and 650 nm in a Powerwave (Biotek Instruments).

Figure 5:
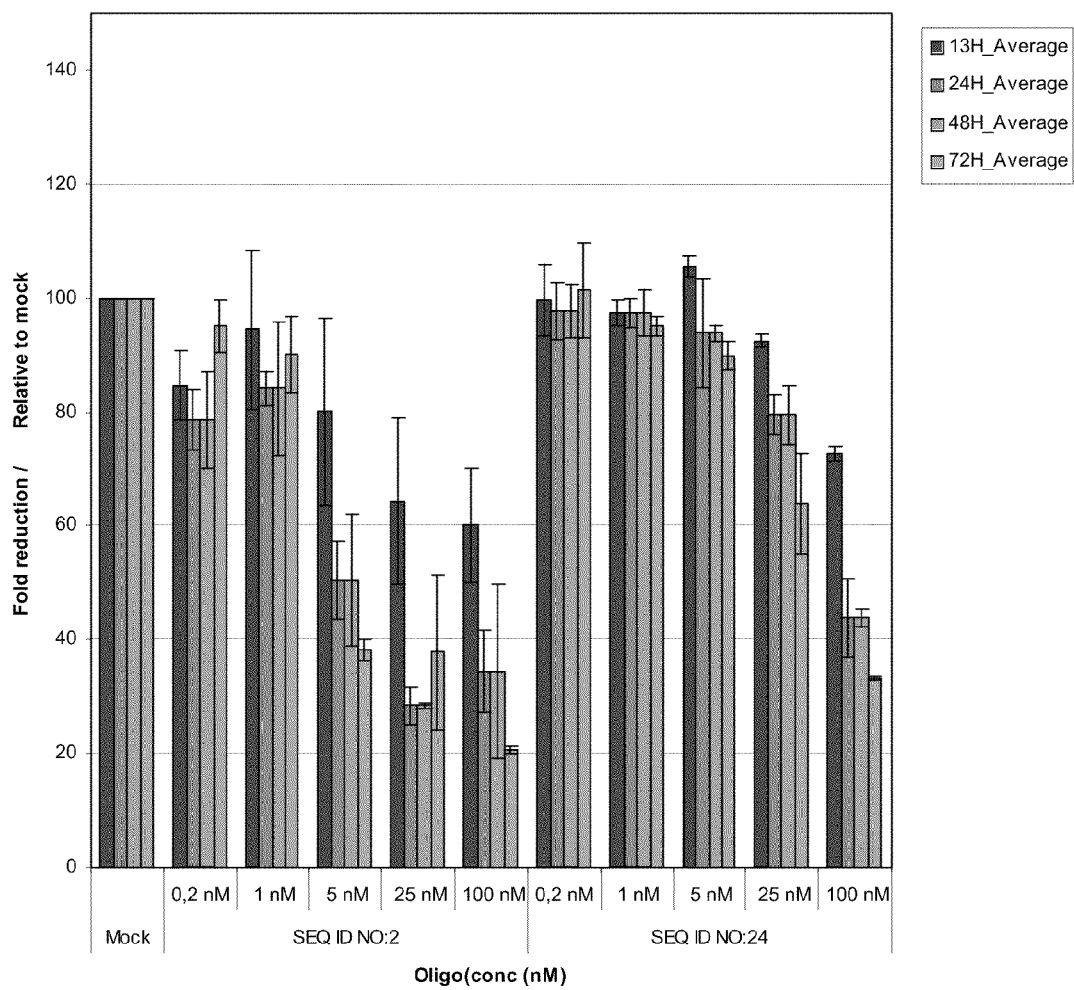
FIG. 5 shows proliferation of 15PC3 prostate cancer cells after treatment with SEQ ID NO. 2 for 13-72 hours after transfection. 15PC3 cells were transfected with SEQ ID NO. 2 or a negative control oligonucleotide, SEQ ID NO. 24 at 0.2, 1, 5, 25 and 100 nM. The relative number of viable cells, compared to untreated mock cells is shown. Data derives from three independent experiments. The standard deviation is presented on each bar. SEQ ID NO. 2 leads to a dose dependent inhibition of proliferation whereas the negative control SEQ ID NO. 24 does not.

The inhibition of growth rate ΔOD (490-650 nm)/h was plotted against the oligonucleotide concentration relative to mock, which was set to 100%. The maximum inhibition of proliferation observed in the MTS assay was 70% (minimum 30%). (Table 5 and FIG. 5)

TABLE 5

Proliferation inhibition of oligonucleotide transfected 15 PC3 cells

| MTS assay | Oligonucleotide | Inhibition of proliferation |
| --- | --- | --- |
| $IC_{50}$ (48 hours) | SEQ ID NO. 2 | 4.9 nM |
| | SEQ ID NO. 24 | 86.9 nM |

Example 14

Apoptosis Induction by SEQ ID NO. 2 in Combination with Taxol

Cell culturing: Human prostate cancer 15PC3 cells (kindly provided by Dr. F Baas, Neurozintuigen Laboratory, AMC, The Netherlands) were seeded to a density of $8 \times 10E5$ cells in T75-flasks and grown for two days at 37° C. and 5% $CO_2$ in DMEM supplemented with 10% FBS, Glutamax and Gentamicin. Two days following seeding cells were transfected with 2-10 nM SEQ ID NO. 2 using Lipofectamine at a final conc. of 7.5 µg/ml. Transfections were carried out as described by Dean et al. (1994, JBC 269 p. 16416 16424). In short cells were incubated with Lipofectamine diluted in OptiMEM for 7-10 min followed by the addition of the oligonucleotide to total volume of 8.7 ml per T75 flask. 4 hours following transfection cells were washed in OptiMEM and grown at 37° C. for 12-96 hours in complete growth medium with or without the addition of 2-100 nM Taxol (Sigma Aldrich). Cells were harvested for either mRNA extraction, Caspase 3/7 assay or fixed, stained with PI and analysed by FACS analysis.

Caspase 3/7 assay: An equal amount of 15PC3 cells ranging from 2500-10000 cells were harvested by centrifugation at the indicated periods and plated in white 96 well plates (Nunc 136101) in DMEM. 100 µl of the highly sensitive Caspase 3/7-Glo™ Reagent (Promega) was added directly to the cells in 96 well and plates were incubated for 1 hour before recording luminescence (luciferase activity) in Luminoskan Ascent instrument from Thermo Labsystems after further 1 min lag period. The luciferase activity is measured as Relative Light Units per seconds (RLU/s). The data was processed in the Ascent software 2.4.2. and graphs of fold induction in relative to mock were drawn in excel. Transfected cells incubated with the caspase 3/7 inhibitor, which block active caspase 3/7 activity were used to demonstrate specificity of the apoptotic response. Moreover, Staurosporine, camptothecine or taxol induced cells served as positive control. See FIG. 6.

Example 15

Cell Cycle Analysis by SEQ 10 NO. 2 in Combination with Taxol

Cell culturing and transfections: As in example 13.
Fixation and PI staining: Cells were washed in PBS, harvested and resuspended in 100 µl in ice cold PBS. 900 µl ice cold 70% was added and fixed cells were kept at −20 until use.

Fixated cells were harvested and resuspended in 700 µl PBS (room temperature). 300 µl Phosphate-Citric acid buffer (0.19 M $Na_2PO_4$, 4 mM Citric acid pH 7.8) was added and the cells were incubated for 5 min at room temperature. The cells were harvested again and incubated for 30 min in PI staining solution (1 mg/ml RNase A, 33 mg/ml propidium iodide, 0.2% (v/v) Triton-X-100 in PBS pH 7.4).

FACS analysis was carried out by using Becton Dickinson FACS Calibur.

Figure 7A:
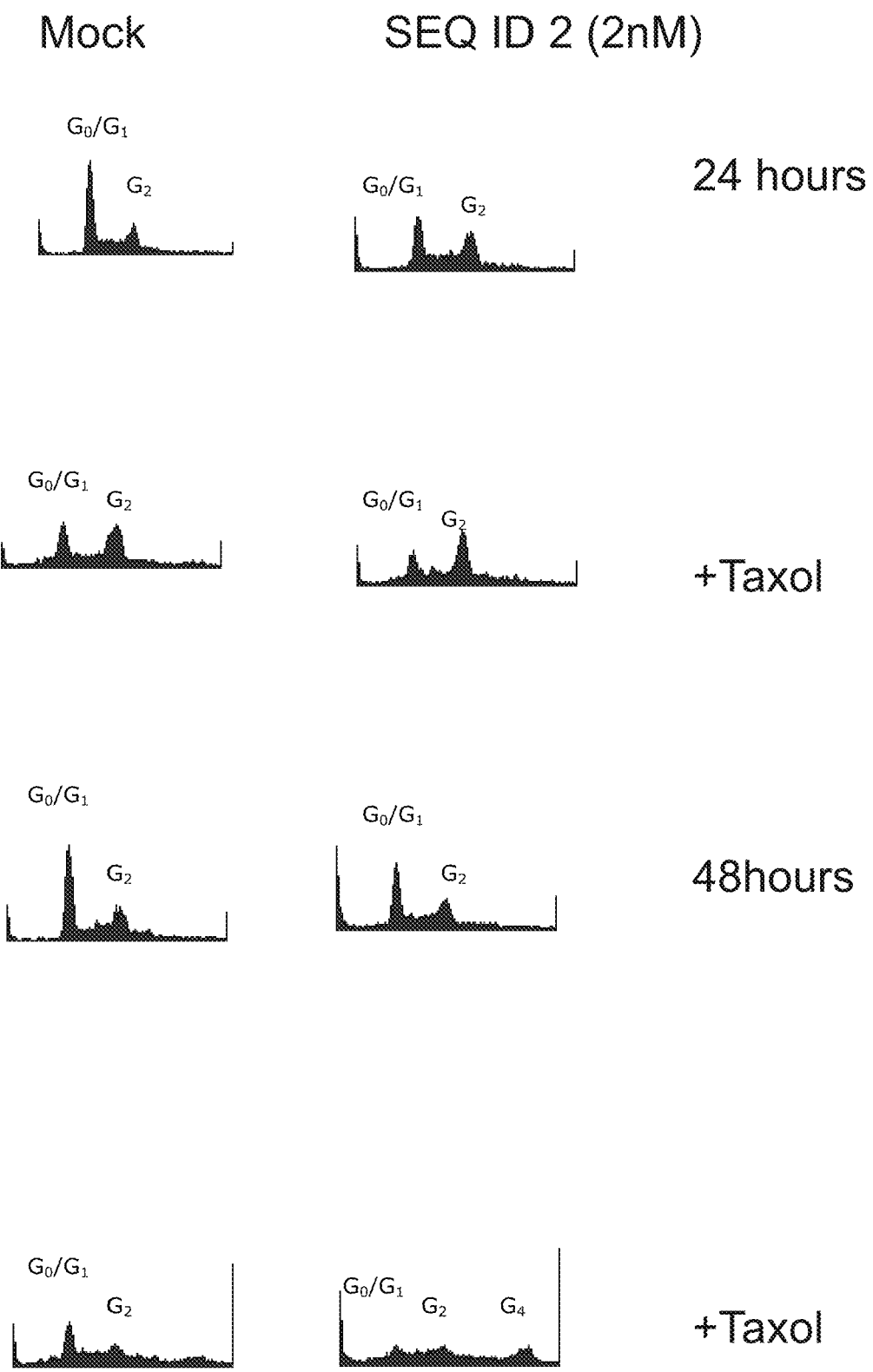
Figure 7B:
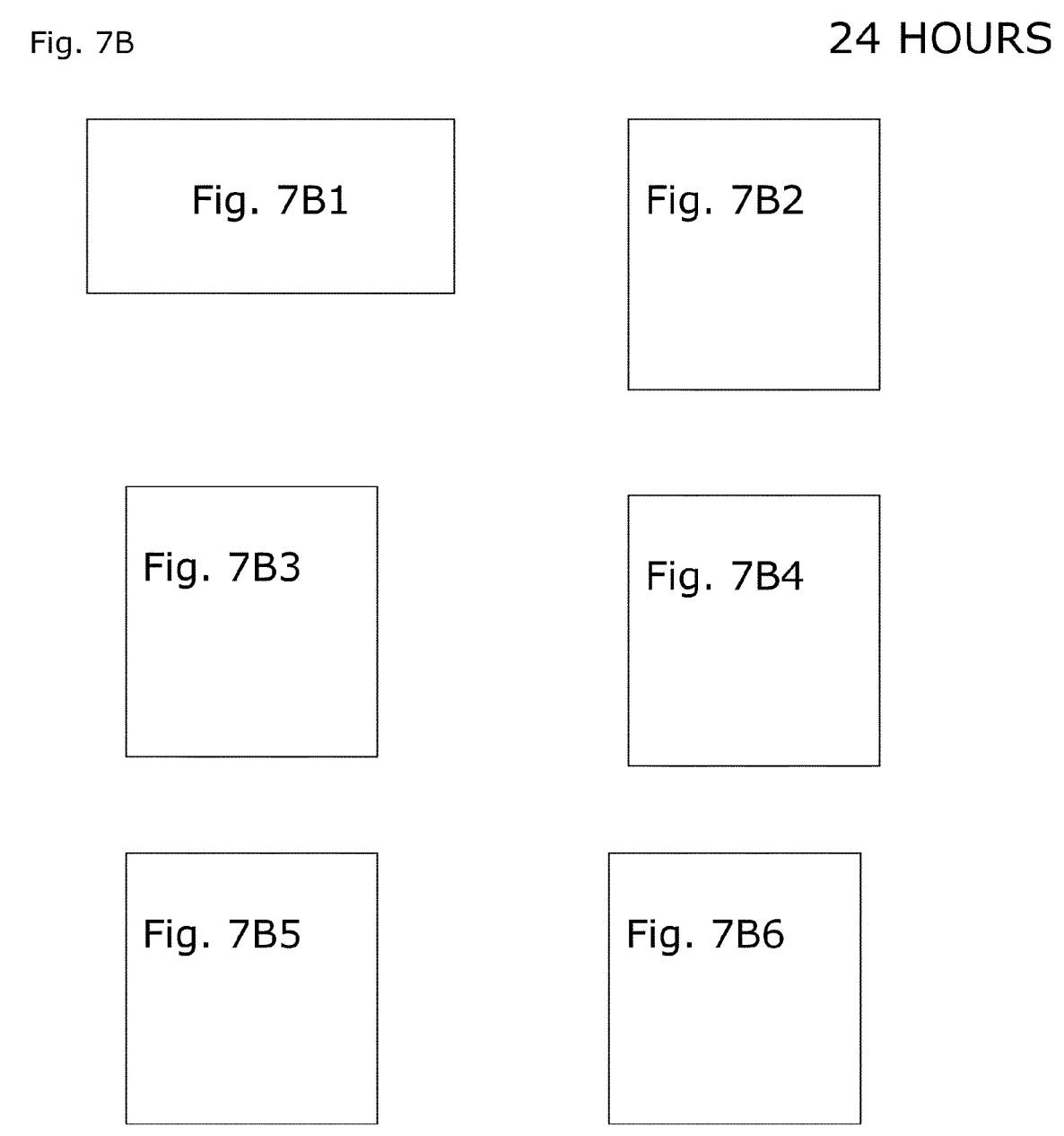

SEQ ID NO. 2 transfected 15PC3 cells were exposed to different concentrations of Taxol and analysed by Propidium Iodide staining and subsequent FACS analysis (FIG. 7a-c). This assay also shows the addition effect of SEQ ID NO. 2 and Taxol by an increasing amount of cells trapped in the G2 or even G4 phase. See FIGS. 7A and 7B plus Example 21.

Example 16

Figure 8:
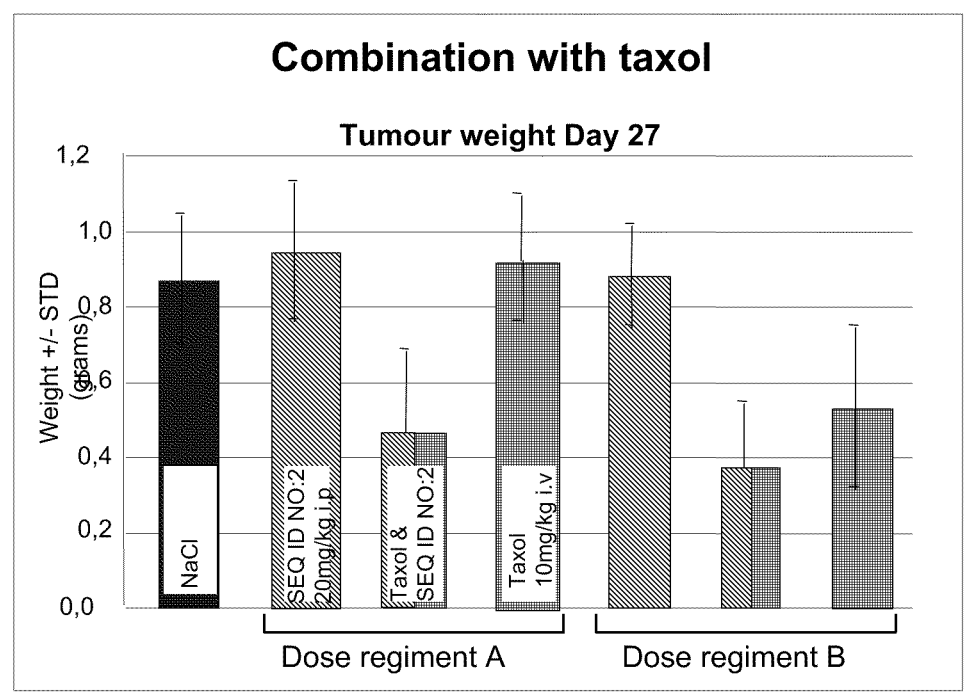
FIG. 8 shows the in vivo properties of SEQ ID NO. 2 and SEQ ID NO. 2 in combination with Taxol. The compounds were given in two different dose schedules (A and B) as outlined in the lower panel of the figure. Tumour weight reduction is seen using both schedules by comparing groups receiving both SEQ ID NO. 2 combined with Taxol after 27 days to those of single agent treatment or saline (mock).
Figure 9:
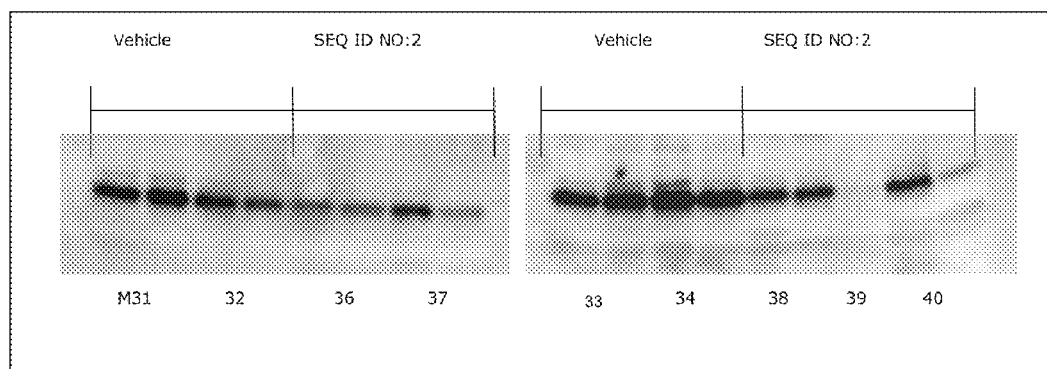
FIG. 9 shows tumour analysis, reduced levels of both mRNA and Survivin protein is shown after intratumoural injections of SEQ ID NO. 2. Saline or 25 mg/kg SEQ ID NO. 2 was given 6 times (50 µl volume) intratumoral over 2 weeks. Sampling was performed 24 hours after last dose.
Figure 9:
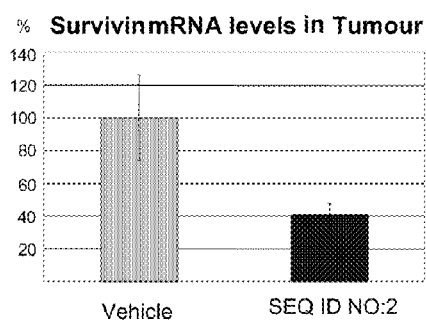

In Vivo Model: Tumour Growth Inhibition of Human Tumour Cells Grown In Vivo by Treatment with Antisense Oligonucleotides Model: PC-3 human prostate cancer cells (ECACC) are mixed with Matrigel and injected s.c. into both flanks of female Balb/cA-nu mice on Day 0.
Dosing: Saline solution of SEQ ID NO. 2 according to schedule, 2 mg/ml working solution, dosing volume 10 ml/kg; Taxol was used in the clinical formulation. The animals were dosed according to the average group weight on Day 0.
Administration: Oligonucleotides i.p. (see FIG. 8) or intratumoural (see FIG. 9), Taxol i.v., all according to schedule
Observations: Mortality (daily), body weight (twice per week),
Tumour volume: During the experiment, tumour volume is measured twice per week and calculated according to the formula $(L \times D^2 \times 0.5)$, where L represents the largest diameter and D the tumour diameter perpendicular to L (mm).
Antitumour activity: Mean tumour weight of treated tumours will be compared with control group.

End of study: The animals will be sacrificed by cervical dislocation. Tumours, livers and spleens will be weighed.
Tumour Analyses
Total RNA isolation: Approximately 20 mg tumour tissue was homogenized in 400 µl RTL buffer (Qiagen) supplemented with 1% mercaptoethanol. Total RNA was isolated using RNeasy mini kit (Qiagen) according to the manufacture's instructions.
cDNA synthesis: First strand synthesis was performed using OmniScript Reverse Transcriptase kit according to the manufacturer's instructions (Qiagen). For each sample, 0.5 µg total RNA was adjusted to 12 µl and mixed with 0.2 µl poly (dT)$_{12-18}$ (0.5 µg/µl) (Life Technologies), 2 µl dNTP mix (5 mM each), 2 µl 10×RT buffer, 0.5 µl RNAguard™ RNase Inhibitor (33 units/ml, Amersham) and 1 µl OmniScript Reverse Transcriptase followed by incubation at 37° C. for 60 min. and heat inactivation at 93° C. for 5 min.
Intratumoral 25 mg/kg SEQ ID NO. 2 or saline was given 6 times (50 µl volume) over 2 weeks. Sampling was performed 24 hours after last dose. Expression level was established with 9 tumours (SEQ ID NO. 2) versus 8 tumours (saline) on mRNA level. Protein levels were analysed on individual tumours by western blotting (see FIG. 9).
Real time PCR analysis: To determine the relative Survivin mRNA level treated and untreated tumours, the generated cDNA was used in quantitative PCR analysis using an iCycler from BioRad. The cDNA was diluted 5-fold and 8 µl was mixed with 52 µl Taqman probe master mix containing 30 µl Platinum Quantitative PCR SuperMix UDG 2×PCR master mix (Invitrogen), 3 µl 20× Taqman probe and primer mix (forward primer: 5'-AAGGACCACCGCATCTCTACA-3' (SEQ ID NO. 29), final 0.9 µM. Reverse primer: 5'-CCAAGTCTGGCTCGTTCTCAGT-3' (SEQ ID NO. 30), final 0.6 µM and taqman probe: FAM-5'-CGAGGCTGGCT-TCATCCACTGCC-TAMRA-3' (SEQ ID NO. 31), final 0.1 µM) and 19 µl $H_2O$. The 60 µl was dispersed in two wells (96 well plates) with 25 µl in each well. The primers and probe were obtained from Proligonucleotide, France. To normalize any variance in sample preparation, the endogenous GAPDH mRNA was quantified using a pre-developed Taqman assay reagent from Applied Biosystems (4310884E) according to manufacture's instructions. 2-fold dilutions of cDNA synthesised from untreated 15PC3 (expressing both Survivin and GAPDH) was used to prepare standard curves for the assays. The PCR program was as follows: 50° C. for 2 min., 95° C. for 10 min. followed by 40 cycles of 95° C. 15 sec., 60° C. 1 min. Relative quantities of Survivin mRNA were determined from the calculated Threshold cycle using the iCycler IQ Real Time Detection System software. See FIG. 9.
Total protein isolation and Western Blotting: Approximately 50 mg tumour tissue was homogenized using a Retsch homogenisator in 50 mM Tris-HCl pH 6.8, 10% glycerol, 2.5% SDS, 5 mM DTT and 6 M urea supplemented with protease inhibitor cocktail (Roche). Total protein concentrations were measured using a BCA protein assay kit (Pierce). 50 µg total protein was run on a 12% Bis-Tris gels in MOPS buffer and blotted onto a PVDF membranes according to manufacture's instructions (Invitrogen). After overnight incubation in blocking buffer (PBS-T supplemented with 5% low fat milk powder), the membranes were incubated overnight with 1:500 dilution of polyclonal anti-Survivin antibody Novus 500-201 followed by one hour incubation with 1:1000 dilution of anti-Bcl (DAKO). Membranes were then incubated with secondary antibodies (either 1:1000 diluted HRP conjugated secondary antibodies from DAKO or AP conjugated antibodies from Invitrogen) and Survivin and Bcl2 were visualized using a chromogenic immunodetection kit (Invitrogen) or a chemiluminescens ECL+ detection kit (Amersham). See FIG. 9.

Example 17

In Vitro Combination of Survivin Antisense Oligonucleotide and Radiation

There is increasing evidence in the scientific literature demonstrating a correlation between overexpression of the apoptosis inhibitor protein (IAP) Survivin and radioresistance. Furthermore, down-regulation of Survivin has been shown to cause radiosensitisation in cancer cell lines in vitro.

Transfection of the melanoma cell lines JR8 and M14 stably transfected with a construct expressing a ribozyme, which targets Survivin, resulted in 50-60% down-regulation of Survivin protein, increased apoptosis measured by Caspase 3 activation and propidium iodide staining, as well as increased sensitivity to γ-irradiation, assessed as changes of viability by the clonogenic assay (Pennati et al., 2003; J. Invest. Dermatol. 120, 648-54).

In colorectal cancer cell lines, a clear correlation between Survivin expression levels and radiosensitivity has been shown (Rödel et al., 2003; Int. J. Radiation Oncology Biol. Phys. 55, 1341-47). SW 480 cells with the lowest radiosensitivity showed the highest spontaneous expression of Survivin. Actually, Survivin protein was even upregulated 48 hours after irradiation in SW 480 cells. Conversely, Survivin expression was low in untreated and not increased after irradiation in the most radiosensitive cell line SW 48.

Pancreatic MIAPaCa-2 cancer cells overexpressing recombinant Survivin are less radiosensitive than untransformed cells. On the contrary, the radioresistant pancreas cancer cell line Panc-1, when transformed with a dominant negative Survivin mutant, augments radiosensitivity and Caspase 3 activity (Asanuma et al., 2002; Jpn. J. Cancer Res. 93, 1057-62).

Treatment of the lung cancer cell line H460 with a Survivin antisense oligonucleotide decreased cell viability of irradiated H460 cells in vitro (Lu et al., 2004; Cancer Research 64, 2840-45). In vivo, delay of tumour growth in H460 xenografts in nude mice treated with a combination of a Survivin antisense oligonucleotide and irradiation was greater than in mice treated with the oligonucleotide or irradiation alone (Cao et al., 2004; Oncogene 23, 7047-52).

These data clearly indicate that Survivin plays an important role in radioresistance and down-regulation of Survivin may result in a therapeutic benefit in the field of radiation treatment of cancer. Sensitisation of cancer cells to radiotherapy may result in reduced radiation doses and thus less severe side effects and even increased efficacy.

Combination of SEQ ID NO. 2 and irradiation will be performed by transfecting various cell lines including U87 and U373 cells (glioblastoma), H460 (NSCLC) and LS 174 T (Colon cancer) cells with the oligonucleotide and subsequently treating them with irradiation. The effect will be related to mock transfected cells receiving the same treatment regimen, which will show the effect of radiation alone. After irradiation, cells will be analysed for viability using the MTT and the clonogenic assay. Apoptosis will be assessed by Caspase 3 activity measurements, TUNEL assay and Hoechst staining.

Example 18

In Vivo Combination of Survivin Antisense Oligonucleotide SEQ Id No. 2 and Fractionated Radiotherapy in Subcutane U87 Glioblastoma Xenografts in Nude Mice $2 \times 10^5$ in vitro grown U87 cells were Injected into the right flank of 6-7 week old male NMRI nu/nu mice. When tumours had reached a mean size of 200 mm³, the animals were treated with SEQ ID NO. 2, the negative control oligonucleotide SEQ ID NO. 24, or 0.9% Nacl (saline) i.p. The oligonucleotides were injected as saline solutions at 20 mg/kg/treatment day.

The following groups, each comprising 8 mice, were included in the study:
1. 0.9% NaCl i.p.
2. SEQ ID NO. 2 i.p.
3. SEQ ID NO. 24 i.p.
4. SEQ ID NO. 2 i.p.+Radiotherapy
5. SEQ ID NO. 24 i.p.+Radiotherapy
6. 0.9% NaCl i.p.+Radiotherapy.

Radiotherapy was given as a single dose of 3 Gy, antero-posteriorily as two opposing lateral fields, in four fractions on four days according to the treatment scheme below. During radiation therapy, the animals were anaesthetised with ketalar and rompun. Animals not receiving radiation therapy were anaesthetised in the same way.

| | Treatment Day | | | | | | | | |
|---|---|---|---|---|---|---|---|---|---|
| | 1 | 2 | 3 | 4 | 5 | 6 | 7 | 8 | 9 |
| i.p. Treatment | X | X | | X | | X | | X | X |
| Radiation therapy | | | X | X | X | X | | | |

Tumour growth was determined by two perpendicular measurements ($d_1$ and $d_2$) using a sliding gauge. Tumour volumes [V(t)] were calculated according to the following formula:

$$V(t) = 0.35(d_1(t) \times d_2(t))^{3/2}$$

Tumour growth was measured until tumours reached a size of 1000 mm³.

Body weight of all animals was determined at the start of treatment, then once per week.

Example 19

Pre Clinical GLP Toxicity Studies with SEQ ID NO. 2 in Rodents and Cynomolgus Monkeys For SEQ ID NO. 2 the following was found among others in preclinical toxicity studies:

In i.v. acute toxicity studies in mice the maximum non-lethal dose was found to be 1000 mg/kg.

In i.v. acute toxicity studies in rats the lowest lethal dose was found to be 1000 mg/kg.

In an i.v. MTD study in cynomolgus monkeys, there were found no notable clinical signs however evidence of liver and kidney toxicity was apparent in all animals. The animals were treated with either a dose escalating design with a maximum dose of 160 mg/kg×3 (total dose of 930 mg/kg) or a 120 mg/kg×5 over 2 weeks.

In an i.v. 4 weeks repeat dose toxicity study in cynomolgus monkeys SEQ ID NO. 2 was administered at doses of 0, 6, 15 and 60 mg/kg/occasion twice weekly for four weeks. In the groups of animals receiving 0, 15 or 60 mg/kg/occasion some animals were followed for a recovery period of 4 weeks without treatment.

Tissues including liver and kidney samples were snap frozen and stored at −70° C. for subsequent analysis.

Example 20

Oligonucleotide Content in Cynomolgus Monkey Tissues

Sample Preparation: Extraction from Liver and Kidney Tissues
Chemicals/Reagents:
Proteinase K (25.1 mg/ml): Sigma P4850.
Phenol-chloroform-isoamyl-alcohol (25:24:1 (v/v/v), saturated with 10 mM Tris, pH: 8.0, 1 mM EDTA: Sigma P2069
Igepal CA-630: Sigma, 18896.
Extraction buffer: 0.5% Igepal CA-630, 25 mM Tris pH 8.0, 25 mM EDTA, 100 mM NaCl, pH 8.0 (adjusted with 1 N NaOH).

1 mg/ml of Proteinase K in extraction buffer: Prepared before each extraction.

Tissues (~100 mg) is weighed off (tissue is kept on dry-ice before and after weighing). 500 µl extraction buffer containing proteinase K (1 mg/ml) is added. The tissue is homogenized mechanically and the homogenate is incubated over night at 37° C.

Reference samples are prepared by dissolving SEQ ID NO. 2 in extraction buffer at the relevant concentration range. Exactly 100 mg liver tissue from un-treated animals is weighed off (kept on dry-ice before and after weighing). Extraction buffer (with proteinase K, 1 mg/ml) containing the reference material is added to the tissue samples to a total volume of 0.5 ml. The tissue is mechanically homogenized and is incubated over night at 37° C. The detection signal of SEQ ID NO. 2 from these samples is used to prepare a standard curve covering the lowest and the highest concentrations found in the treated animals.

Tissue samples are transferred to 2 ml microtubes with screw caps. 1 ml phenol-chloroform-isoamyl-alcohol (25:24:1 (v/v/v)) is added following vigorously shaking for 5 min. Phase separation is achieved by centrifugation at 4000 RPM for 15 min. The aqueous phase (upper-phase) is transferred to a new tube (compatible with the evaporator) and 500 µl Milli-Q-H$_2$O is added to the organic phase (residual from the first extraction). The tubes are stirred vigorously again for 5 min, following centrifugation at 4000 RPM for 15 min (SAN039 in room 115). The aqueous phases (water phases from 1. extraction and wash) are pooled and evaporated to dryness (80° C., under nitrogen). The residual is reconstituted in 200 µl Milli-Q-Water following centrifugation at 4000 RPM for 15 min. The samples are transferred to HPLC-vials for analysis.

Figure 10A:
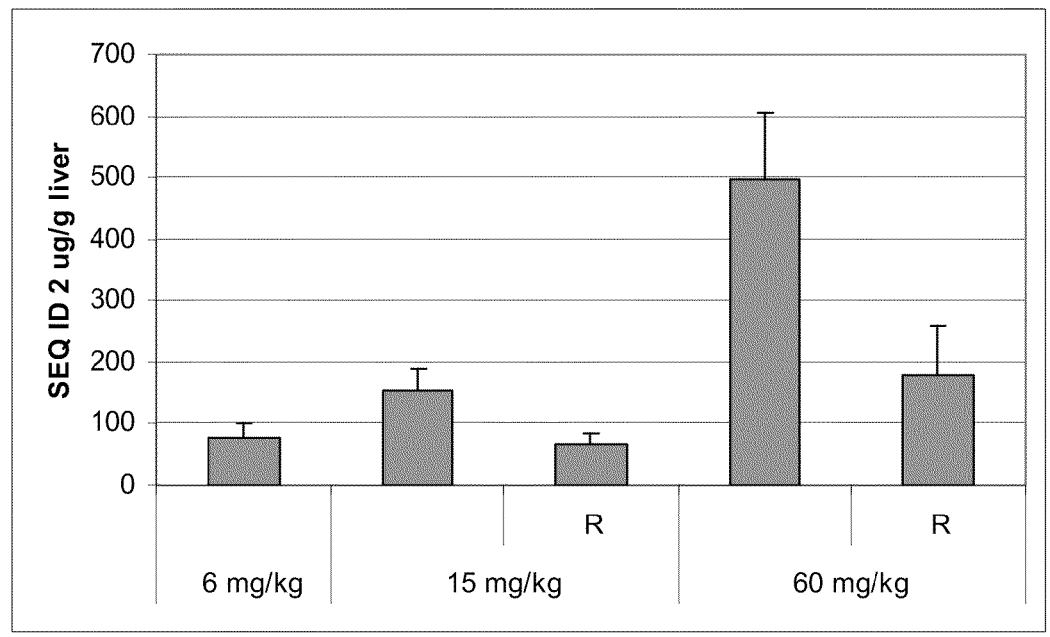
FIG. 10A shows the content of SEQ ID NO. 2 in liver of cynomolgus primates after systemic treatment according to Example 19 with PBS buffered formulations of SEQ ID NO. 2. Recovery animals (R) were left untreated for 4 weeks and show that SEQ ID NO. 2 was detectable after this period in the tissue.
Figure 10B:
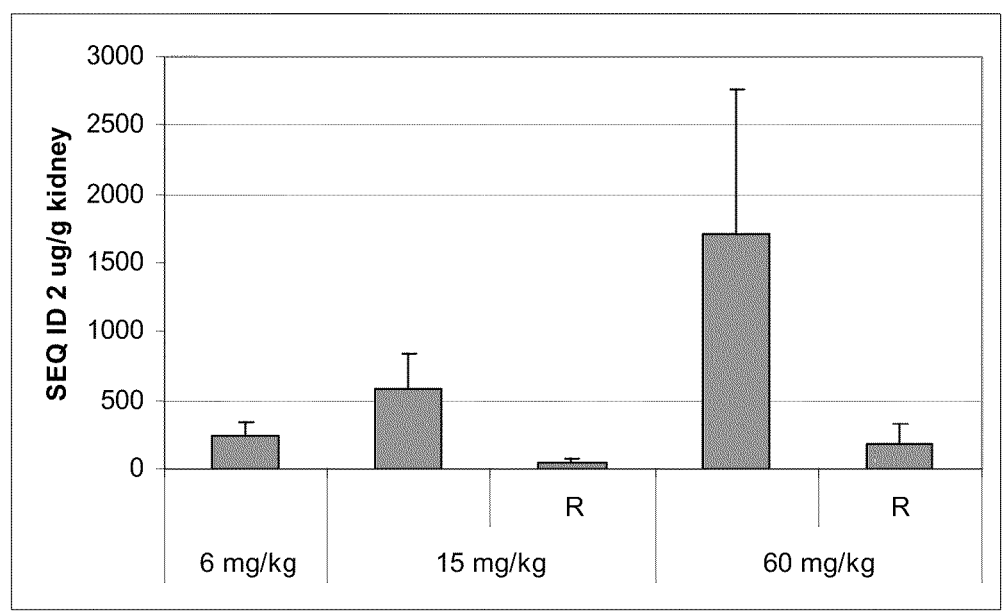
FIG. 10B shows the same as 10A but in kidney instead of liver.

HPLC analysis of oligonucleotide in liver and kidney tissues: Subsequent to the extraction SEQ ID NO. 2 is analysed by ion exchange HPLC:
Column: Dionex, DNA pac PA 100: 2×50 mm (guard), 2×250 mm (analytical).
Column temp: 42° C.
Injection vol.: 50 µl.
Wash-solvent: Milli-Q-H$_2$O.
Purge-solvent: Milli-Q-H$_2$O.
Detection: UV, 260 nm.
Solvents:
Buffer A: 1 mM EDTA, 20 mM TRIS-Cl, 10 mM NaClO$_4$, pH: 7.6 (1 N NaOH)
Buffer B: 1 mM EDTA, 20 mM TRIS-Cl, 1 M NaClO$_4$, pH: 7.6 (1 N NaOH)
See FIGS. 10A and 10B Example 21

Summary of the Results

TABLE 7

|  | SEQ ID NO. 2 | SEQ ID NO. 23 | SEQ ID NO. 22 | SEQ ID NO. 21 |
| --- | --- | --- | --- | --- |
| Size (see Table 2) | 16-mer | 16-mer | 16-mer | 18-mer |
| Design | 4-8-3-1 | 4-8-4 | 4-8-3-1 | 4-10-4 |
| Apoptosis At 5 nM, 24 hours (see FIG. 3) | 3.5-fold | 2-fold | No activity | No activity |
| Max Apoptosis (see FIG. 3) | 6.5-fold (25 nM, 24 hours) | 5.5-fold (25 nM, 48 hours) | 2.5-fold (25 nM, 48 hours) | 2.5-fold (25 nM, 48 hours) |
| Proliferation IC$_{50}$ (48 hours, nM) (see FIG. 5) | 5.0 | n.d. | 25 | 25 |
| Cell cycle arrest G2/M |  | n.d. | n.d. | n.d. |
| G1:G2 (24 hours) | 1:0.25 |  |  |  |
| 0 nM | 1:1 |  |  |  |
| 2 nM | 1:3 |  |  |  |
| 2 nM + 10 nM Taxol (see FIG. 7 A and B) |  |  |  |  |
| Tm (° C.) complementary RNA | 75.3 | n.d. | n.d. | 62.7 |

SEQ ID NO. 2 leads to down-regulation of Bcl-2, which is not found with the negative controls.

The invention claimed is:

1. A method of treating a mammal suffering from cancer, the method comprising the step of administering to the mammal one or more therapeutically effective doses of a pharmaceutical composition comprising (i) taxol; and (ii) an LNA oligonucleotide having the sequence:

(SEQ ID NO: 2)
5'-$^{Me}C_sT_s{}^{Me}C_sA_sa_st_sc_sc_sa_st_sg_sg_s{}^{Me}C_sA_sG_sc$-3' wherein capital letters designate a β-D-oxy-LNA, lower-case letters designate a deoxynucleotide, and the subscript "s" designates a phosphorothioate linkage between adjacent nucleotides/LNA nucleotide analogues, and wherein the weight ratio between the taxol and the LNA oligonucleotide in said composition is in the range of 1:1 to 10:1.

2. The method of claim 1, wherein the cancer is prostate cancer.